(12) United States Patent
Zhong et al.

(10) Patent No.: US 12,371,415 B2
(45) Date of Patent: Jul. 29, 2025

(54) QUINAZOLINE DERIVATIVE SALT CRYSTAL FORM, PREPARATION METHOD AND APPLICATION

(71) Applicant: WEISHANG (SHANGHAI) BIO-PHARMACEUTICAL CO., LTD., Shanghai (CN)

(72) Inventors: Wei Zhong, Shanghai (CN); Jinqiang Zhang, Shanghai (CN)

(73) Assignee: WEISHANG (SHANGHAI) BIO-PHARMACEUTICAL CO., LTD., Shanghai (CN)

( * ) Notice: Subject to any disclaimer, the term of this patent is extended or adjusted under 35 U.S.C. 154(b) by 474 days.

(21) Appl. No.: 17/625,315

(22) PCT Filed: Mar. 21, 2019

(86) PCT No.: PCT/CN2019/079043
§ 371 (c)(1),
(2) Date: Jan. 6, 2022

(87) PCT Pub. No.: WO2019/196619
PCT Pub. Date: Oct. 17, 2019

(65) Prior Publication Data
US 2024/0025874 A1    Jan. 25, 2024

(30) Foreign Application Priority Data

Apr. 8, 2018  (CN) .......................... 201810309035.1
May 4, 2018   (CN) .......................... 201810423951.8

(51) Int. Cl.
*C07D 401/12* (2006.01)
*A61P 35/00* (2006.01)

(52) U.S. Cl.
CPC ............ *C07D 401/12* (2013.01); *A61P 35/00* (2018.01)

(58) Field of Classification Search
CPC ............................... C07D 401/12; A61P 35/00
See application file for complete search history.

(56) References Cited

U.S. PATENT DOCUMENTS

| | | | |
|---|---|---|---|
| 4,992,445 A | 2/1991 | Lawter et al. | |
| 5,001,139 A | 3/1991 | Lawter et al. | |
| 5,023,252 A | 6/1991 | Hseih | |

FOREIGN PATENT DOCUMENTS

| | | | | |
|---|---|---|---|---|
| CN | 101128456 A | 2/2008 | | |
| CN | 102088979 A | 6/2011 | | |
| CN | 105859641 A | 8/2016 | | |
| WO | WO-2009138781 A1 | * 11/2009 | ........... | A61K 31/517 |
| WO | 2015154725 A1 | 10/2015 | | |

OTHER PUBLICATIONS

Qingbei Zeng, et al., Discovery and Evaluation of Clinical Candidate AZD3759, a Potent, Oral Active, Central Nervous System—Penetrant, Epidermal Growth Factor Receptor Tyrosine Kinase Inhibitor, Journal of Medicinal Chemistry, 2015, pp. 8200-8215 vol. 58.

Curtis R Chong, et al., The quest to overcome resistance to EGFR-targeted therapies in cancer, Nature Medicine, 2013, pp. 1389-1400, vol. 19 No. 11.

Fortunato Ciardiello, et al., EGFR Antagonists in Cancer Treatment, The New England Journal of Medicine, 2008, pp. 1160-1174, vol. 358.

Robert Roskoski Jr., The ErbB/HER receptor protein-tyrosine kinases and cancer, Biochemical and Biophysical Research Communications, 2004, pp. 1-11, vol. 319.

Terrance G. Johns, et al., The epidermal growth factor receptor variant III (EGFRvIII): where wild things are altered, The FEBS Journal, 2013, pp. 5350-5370, vol. 280.

Paul S. Mischel, et al., EGFR Mutation Promotes Glioblastoma through Epigenome and Transcription Factor Network Remodeling, Molecular Cell, 2015, pp. 307-318, vol. 60.

Hans Bundgaard, (C) Means to Enhance Penetration, (1) Prodrugs as a means to improve the delivery of peptide drugs, Advanced Drug Delivery Reviews, 1992, pp. 1-38, vol. 8.

(Continued)

*Primary Examiner* — Kortney L. Klinkel
*Assistant Examiner* — Donna M Nestor
(74) *Attorney, Agent, or Firm* — Bayramoglu Law Offices LLC

(57) ABSTRACT

A quinazoline derivative (represented by the formula (I)) salt's crystal form, a preparation method and application are provided; specifically, the hydrochloride crystal form A, B, C, D, F, H, I, Sulphate crystal form A, Maleate crystal form A, Succinate crystal form A, Adipate crystal form A, Glycolate crystal form A, Malate crystal form A, Fumarate Salt crystal form A, besylate crystal form A, B, C, benzoate crystal form A, hippurate crystal form A and oxalate crystal form A of the quinazoline derivative represented by formula (I). The salt crystal form provided by the present invention has good stability, which can be used in the treatment of non-small cell lung cancer brain metastasis, meningeal metastasis, primary brain cancer or glioma, etc., and has good bioavailability, which is of great significance for further research on the efficacy of such solid drugs.

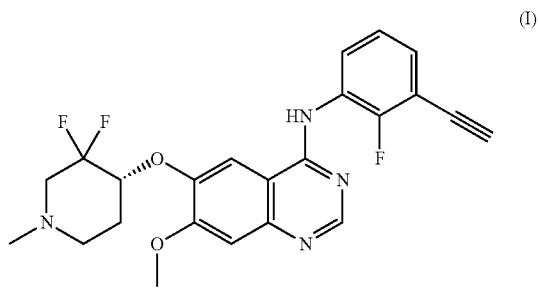

(I)

27 Claims, 13 Drawing Sheets

(56) References Cited

OTHER PUBLICATIONS

Nobuharu Kakeya, et al., Studies on Prodrugs of Cephalosporins. I. Synthesis and Biological Properties of Glycyloxybenzoyloxymethyl and Glycylaminobenzoyloxymethyl Esters of 7β-[2-(2-Aminothiazol-4-yl)-(Z)-2-methoxyiminoacetamido]-3-methyl-3-cephem-4-carboxylic Acid, Chem Pharm Bull, 1984, pp. 692-698, vol. 32 No.2.
Stephen M. Berge, et al., Pharmaceutical Salts, Journal of Pharmaceutical Sciences, 1977, pp. 1-19, vol. 66 No. 1.
Samuel H. Wilen, Strategies in Optical Resolutions, Tetrahedron, 1977, pp. 2725-2736, vol. 33.
Jose Alexander, et al., (Acyloxy)alkyl Carbamates as Novel Bioreversible Prodrugs for Amines: Increased Permeation through Biological Membranes, Journal of Medicinal Chemistry, 1988, pp. 318-322, vol. 31 No.2.
Bundgaard, et al., Communications to the Editor, Journal of Medicinal Chemistry, 1987, pp. 451-454, vol. 30 No. 3.
M. Stern, et al. Overview of monoclonal antibodies in cancer therapy: present and promise, Critical Reviews in Oncology/Hematology, 2005, pp. 11-29, vol. 54.

* cited by examiner

QUINAZOLINE DERIVATIVE SALT CRYSTAL FORM, PREPARATION METHOD AND APPLICATION

CROSS REFERENCE TO THE RELATED APPLICATIONS

This application is the national phase entry of International Application No. PCT/CN2019/079043, filed on Mar. 21, 2019, which is based upon and claims priority to Chinese Patent Application No. 201810309035.1, filed on Apr. 8, 2018, and Chinese Patent Application No. 201810423951.8, filed on May 4, 2018, the entire contents of which are incorporated herein by reference.

TECHNICAL FIELD

The present invention relates to a quinazoline derivative salt form and its crystal form; specifically to (R)-6-[(3,3-difluoro-1-methylpiperidin-4-yl)oxy]-N-(3-Ethynyl-2-fluorophenyl)-7-methoxyquinazolin-4-amine (I) hydrochloride crystal form A, B, C, D, F, H, I, sulfuric acid salt crystal form A, maleate crystal form A, succinate crystal form A, adipate crystal form A, glycolate crystal form A, malate crystal form A, fumarate crystal form A, Besylate crystal forms A, B, C, benzoate crystal form A, hippurate crystal form A and oxalate crystal form A, and preparation methods and applications thereof.

BACKGROUND

Biological signaling refers to the stimulation or inhibition of signaling sent to the cell, through a series of signal transmission, resulting in intracellular biological response. Many studies have been conducted on many signaling pathways and their biological responses. Different defects in the signaling pathways have been found to be responsible for many diseases, including various forms of cancer, metabolic disorders, inflammatory diseases, vascular and neuronal diseases. These defects often occur at the level of genes, such as DNA insertion, deletion or translocation, and result in uncontrolled cancer cells growth.

Signal transduction is often mediated by certain proteins known as kinases. Kinases are usually divided into protein kinases and lipid kinases, and some kinases that exhibit double specificity. Protein kinases are phosphorylated enzymes that catalyze the phosphorylation of other proteins and/or autophosphorylated and can be classified based on their effect on the substrate, for example: tyrosine kinases refer to phosphorylated tyrosine residues (e.g., Kit, EGFR, HFR2, VEGFR, PDGFR, SRC and ABL, etc.), serine/threonine kinases refer to phosphorylated serine and/or threonine residues (e.g., mTORC1, mTORC2, ATM, ATR, Akt, etc.) and the bispecific tyrosine, serine and/or threonine residues that phosphorylates the of the substrate.

Epidermal growth factor receptor (EGFR) belongs to the ErbB receptor family of transmembrane protein tyrosine kinases, including epidermal growth factor receptor EGFR/ERBB1, HER2/ERBB2/NEU, HER3/ERBB3, and HER4/ERBB4. Binding to an epidermal growth factor (EGF) ligand induced an EGFR receptor forms a homodimer with another EGFR receptor or heterodimer with another family member, e.g., HER2/ERBB2/NEU, HER3/ERBB3, or HER4/ERBB4, leading to activation of EGFR tyrosine kinase activity. The activated EGFR then phosphorylates its substrate, resulting in multiple downstream signals within the cell, including the PI3K-AKT-mTOR pathway (involved in cell viability activation), and the RAS-RAF-MEK-ERK pathway (involving cell proliferation). ErbB receptor signaling and its involvement in tumors, see, for example, Chong et al. Nature Med. 2013; 19 (11):1389-1400; N Engl J Med. (2008) Vol. 358, 1160-74 and Biochemical and Biophysical Research Communications (2004) Vol. 319, 11-11.

Glioma is the most common primary brain tumor, accounting for 40-50% of brain tumors. About 60% of patients with glioma have tumor-related EGFR mutations. About 70% of the mutations are the deletion of EGFRV3 (EGFRVIII) in exons 2-7. This mutation increases the kinase activity of EGFR, leading to excessive activation of downstream pro-survival signaling pathways. EGFRV3 (EGFRVIII) is the deletion gene of exons 2-7 of epidermal growth factor EGFR and prevents the mutant receptor from binding to any known ligands. EGFRV3 mutations are expressed in brain cancer, glioma, bladder cancer, breast cancer, colorectal cancer, esophageal cancer, head and neck squamous cell carcinoma, lung cancer, lung squamous cell carcinoma, ovarian cancer, prostate cancer, brain stem tumors, etc. See, Terrance G. Johns et al., FEBS Journal 280 (2013) 5350-5370.

The release of the ErbB family signaling promotes the proliferation, invasion, metastasis, angiogenesis and survival of tumor cells and has been described in many human cancers, including the lung, head and neck and breast, so the ErbB family represents the development of anticancer drug targets. Small molecule drugs targeting EGFR or ErbB2, including gefitinib (Iressa), erlotinib (Tarceva), afatinib, tagrisso, and lapatinib (TYKERB™, TYVERB™) have been clinically approved for non-small cell lung cancer, especially for EGFR mutations such as Exon 19 deletion or exon 21 L858R mutation. Because EGFRVIII is a deletion gene of EGFR exons 2-7 and prevents the mutant receptor from binding to any known ligands, which is completely different from Exon 19 deletion of Exon 21 L858R mutation, current EGFR inhibitors cannot effectively inhibit EGFRVIII, and their biological activity on EGFRVIII is much lower than for EGFR exon 19 deletion or exon 21 L858R mutation. The activity is often reduced by 10 times, or even more than 100 times, see, for example, Paul S. Mischel et al. Molecular Cell, 60, 307-318, 2015. At the same time, due to the existence of the blood-brain barrier (BBB), the currently approved drugs cannot achieve effective intracranial doses. For gliomas, radiotherapy and surgery supplemented with chemotherapy drugs (temozolomide) are still the main treatment methods, but the treatment effect is limited, and the overall survival period is about 10 months.

Therefore, it is particularly useful to develop a drug with high biological activity with EGFR VIII mutations and at the same time with the ability to cross the blood-brain barrier for the treatment or prevention of EGFR-mediated gliomas.

As we all know, there may be significant differences in the stability, solubility, and bioavailability of different crystal forms, salt forms, and salt crystal forms of the same drug, which may affect the efficacy of the drug. Therefore, it is very useful to develop new salt forms and new crystal forms of quinazoline derivatives that are more conducive to drug processing and pharmaceutical compositions, and to provide more qualitative and quantitative information for the efficacy and safety of solid drugs of great significance.

SUMMARY

The problem to be solved by the present invention is to solve the problem that the existing EGFR inhibitors cannot effectively inhibit the EGFR activating mutation EGFRVIII and effectively cross the blood-brain barrier to reach the effective drug concentration in the skull, and the nature of the free base quinazoline derivatives of the present invention (R)-6-[(3,3-Difluoro-1-methylpiperidin-4-yl)oxy]-N-(3-ethynyl-2-fluorophenyl)-7-methoxyquinazolin-4-amine (I) is not conducive to the problem of use in pharmaceutical processing and pharmaceutical compositions, and provide a quinazoline derivative salt crystal form that is more conducive to pharmaceutical processing and pharmaceutical composition. The salt crystal form, preparation method and application provide more qualitative and quantitative information for the study of the efficacy and safety of solid drugs.

The quinazoline derivatives provided by the present invention have biological activity against EGFRVIII activation mutations, and effectively pass through the blood-brain barrier. The quinazoline derivative is represented by formula (I):

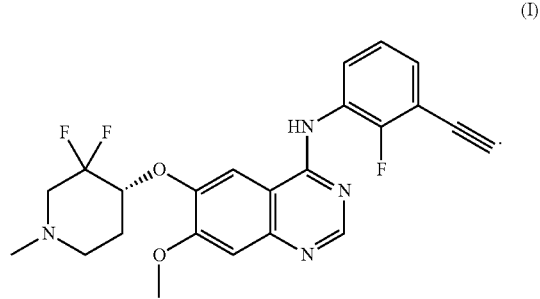 [SMILES: C#Cc1cccc(Nc2ncnc3cc(OC)c(O[C@@H]4CCN(C)CC4(F)F)cc23)c1F]

The purpose of the present invention is achieved through the following technical solutions:

A technical solution adopted by the present invention is to provide a novel quinazoline derivative (I) with a chirality of R.

Preferably, the chiral purity ee>90%, more preferably, the chiral purity ee>97%.

A technical solution adopted by the present invention is to provide a novel quinazoline derivative (I) with a chirality of R that has the biological activity of EGFRVIII activating mutation.

A technical solution adopted by the present invention is to provide a novel quinazoline derivative (I) with a chirality of R, which has the biological activity of EGFRVIII activation mutation and at the same time has a high ability to cross the blood-brain barrier.

The present invention also provides a synthetic method for preparing the quinazoline derivative (I) of the present invention.

A technical solution adopted by the present invention is to provide a quinazoline derivative hydrochloride crystal form A, whose XRPD pattern has peaks at the following 2θ
  Main characteristic peaks: 6.5, 13.1, 9.4
  Secondary characteristic peaks: 7.3, 18.2, 20.0
  The characteristic peaks again: 27.5, 26.6, 21.6
  The error range of the 2θ value is ±0.2.
Preferably, the XRPD pattern of the hydrochloride crystal form A of the quinazoline derivative (I) provided by the present invention is at 2θ=6.48, 7.31, 9.36, 10.26, 13.12, 14.37, 14.98, 16.06, 16.88, 17.48, 18.25, There are derivative peaks at 20.01, 20.83, 21.55, 22.21, 23.35, 25.47, 26.60, 27.46, 28.29, 29.98, 34.07, 34.89, 36.25, 36.47, 36.87, 37.54, and the error range of the above 2θ value is ±0.2.

Another technical solution adopted by the present invention is to provide a quinazoline derivative hydrochloride crystal form B, whose XRPD pattern has peaks at the following 2θ
  Main characteristic peaks: 6.5, 17.7, 19.8
  Secondary characteristic peaks: 7.3, 8.2, 10.5, 13.2
  The error range of the 2θ value is ±0.2.
Preferably, the XRPD pattern of the hydrochloride crystal form B of the quinazoline derivative (I) provided by the present invention is at 2θ=4.32, 5.98, 6.54, 7.28, 8.17, 10.52, 13.20, 15.99, 17.74, 18.48, 19.32, There are derivative peaks at 19.84, 22.56, 23.88, 24.36, 24.87, 30.47, 32.92, 33.55, 34.60, 38.06, 38.34, and the error range of the above 2θ value is ±0.2.

Another technical solution adopted by the present invention is to provide a quinazoline derivative hydrochloride crystal form C, the XRPD pattern has peaks at the following 2θ
  Main characteristic peaks: 7.2, 17.6, 22.0
  Secondary characteristic peaks: 14.0, 13.6, 12.8
  Characteristic peaks again: 24.6, 26.2, 27.3
  The error range of the 2θ value is ±0.2.
Preferably, the XRPD pattern of the hydrochloride crystal form C of the quinazoline derivative (I) provided by the present invention is at 2θ=5.66, 7.16, 8.32, 8.86, 9.52, 10.98, 11.63, 12.80, 13.57, 13.96, 14.81, 15.14, 15.49, 16.55, 16.86, 17.61, 22.04, 22.93, 24.55, 26.19, 27.30, 28.49, 34.12, 34.76, 35.65, 36.68, 37.31, 37.80, 38.20, 38.53.
  The error range of the above 2θ value is ±0.2.

Another technical solution adopted by the present invention is to provide a hydrochloride crystal form D of a quinazoline derivative whose XRPD pattern has peaks at the following 2θ
  Main characteristic peaks: 13.4, 7.1, 25.4
  Secondary characteristic peaks: 6.7, 18.0, 19.8
  The characteristic peaks again: 17.2, 27.3, 24.7
  The error range of the 2θ value is ±0.2.
Preferably, the XRPD pattern of the hydrochloride crystal form D of the quinazoline derivative (I) provided by the present invention is at 2θ=3.43, 6.72, 7.12, 8.47, 9.32, 12.25, 13.44, 14.07, 15.69, 16.87, 17.22, 17.97, 19.77, 20.73, 22.25, 22.82, 23.64, 24.77, 25.40, 27.28, 28.13, 29.69, 31.01, 33.48, 34.87, 35.42, 38.08.
  The error range of the above 2θ value is ±0.2.

Another technical solution adopted by the present invention is to provide a hydrochloride crystal form F of a quinazoline derivative whose XRPD pattern has peaks at the following 2θ
  Main characteristic peaks: 6.8, 20.5, 13.6
  Secondary characteristic peaks: 14.8, 14.3, 17.9, 11.9
  The error range of the 2θ value is ±0.2.
Preferably, the XRPD pattern of the hydrochloride crystal form F of the quinazoline derivative (I) provided by the present invention is at 2θ=4.91, 5.67, 6.51, 6.77, 7.44, 8.58, 9.20, 9.73, 10.40, 10.85, 11.86, 13.58, 14.30, 14.78, 15.57, 15.85, 16.15, 16.41, 16.97, 17.89, 18.96, 19.76, 20.45, 20.79, 21.57, 22.21, 24.17.
  The error range of the above 2θ value is ±0.2.

Another technical solution adopted by the present invention is to provide a quinazoline derivative hydrochloride crystal form H, whose XRPD pattern has peaks at the following 2θ
  Main characteristic peaks: 7.3, 18.0, 14.1
  Secondary characteristic peaks: 6.4, 13.2, 15.8
  Characteristic peak again: 16.8, 14.5, 20.3
  The error range of the 2θ value is ±0.2.

Preferably, the XRPD pattern of the hydrochloride crystal form H of the quinazoline derivative (I) provided by the present invention is at 2θ=5.83, 6.43, 7.26, 8.10, 10.24, 11.93, 13.22, 14.11, 14.45, 14.88, 15.78, 16.80, 17.95, 18.96, 20.25, 21.07, 21.65, 24.16, 24.53, 25.67, 26.37, 27.03, 27.61, and the error range of the above 2θ value is ±0.2.

Another technical solution adopted by the present invention is to provide a hydrochloride crystal form I of a quinazoline derivative, whose XRPD pattern has peaks at the following 2θ

Main characteristic peaks: 18.6, 7.4, 6.9
Secondary characteristic peaks: 13.2, 25.1, 12.3
Characteristic peaks again: 14.7, 28.1, 14.2
The error range of the 2θ value is ±0.2.

Preferably, the XRPD pattern of the hydrochloride crystal form I of the quinazoline derivative (I) provided by the present invention is at 2θ-6.88, 7.42, 8.20, 12.31, 13.20, 13.88, 14.23, 14.66, 15.69, 17.48, 17.90, 18.64, 19.23, 20.24, 20.92, 21.94, 22.88, 23.42, 23.88, 25.12, 25.40, 25.85, 26.64, 28.07, 28.92, 31.19, 33.10, and the error range of the above 2θ value is ±0.2.

Another technical solution adopted by the present invention is to provide a fumarate crystal form A of a quinazoline derivative, whose XRPD pattern has peaks at the following 2θ

Main characteristic peaks: 6.5, 17.8, 9.4
Secondary characteristic peaks: 13.4, 7.5, 19.7
Characteristic peak again: 14.6, 18.5
The error range of the 2θ value is ±0.2.

Preferably, the XRPD pattern of the fumarate crystal form A of the quinazoline derivative (I) provided by the present invention is at 2θ=6.51, 6.74, 7.47, 9.37, 10.82, 13.43, 13.97, 14.61, 17.78, 18.51, 18.80, 19.69, 20.90, 21.36, 21.68, 22.63, 23.76, 24.39, 27.09, 28.73, 29.69, 30.52, 31.07, 35.14, 36.12, 38.33.

The error range of the above 2θ value is ±0.2

Another technical solution adopted by the present invention is to provide a quinazoline derivative succinate crystal form A, whose XRPD pattern has peaks at the following 2θ

Main characteristic peaks: 6.6, 17.8, 7.5
Secondary characteristic peaks: 9.4, 20.3, 18.5
Characteristic peaks again: 21.0, 14.5, 19.5
The error range of the 2θ value is ±0.2.

Preferably, the XRPD pattern of the succinate crystal form A of the quinazoline derivative (I) provided by the present invention is at 2θ=3.92, 4.40, 6.56, 6.74, 7.50, 9.42, 11.92, 12.68, 13.53, 14.50, 14.84, 15.22, 15.68, 16.25, 17.82, 18.55, 19.48, 20.34, 20.99, 22.08, 22.59, 24.14, 24.52, 24.92, 28.07, 30.92, 36.11.

The error range of the above 2θ value is ±0.2.

Another technical solution adopted by the present invention is to provide a quinazoline derivative succinate crystal form A, whose XRPD pattern has peaks at the following 2θ

Main characteristic peaks: 6.6, 17.8, 7.5
Secondary characteristic peaks: 9.4, 20.3, 18.5
Characteristic peaks again: 21.0, 14.5, 19.5
The error range of the 2θ value is ±0.2.

Preferably, the XRPD pattern of the succinate crystal form A of the quinazoline derivative (I) provided by the present invention is at 2θ=3.92, 4.40, 6.56, 6.74, 7.50, 9.42, 11.92, 12.68, 13.53, 14.50, 14.84, 15.22, 15.68, 16.25, 17.82, 18.55, 19.48, 20.34, 20.99, 22.08, 22.59, 24.14, 24.52, 24.92, 28.07, 30.92, 36.11.

The error range of the above 2θ value is ±0.2.

Another technical solution adopted by the present invention is to provide a maleate crystal form A of a quinazoline derivative, whose XRPD pattern has peaks at the following 2θ

Main characteristic peaks: 6.3, 18.8, 16.7
Secondary characteristic peaks: 25.2, 21.2
The error range of the 2θ value is ±0.2.

Preferably, the XRPD pattern of the maleate crystal form A of the quinazoline derivative provided by the present invention is at 28-6.25, 8.44, 8.68, 9.42, 10.41, 14.42, 14.88, 16.65, 17.93, 18.78, 20.58, 21.17, 22.63, 25.16, 31.15, 32.40, 33.66, 34.34, 34.52, 35.82, 36.06, 36.35, 36.91.

The error range of the above 2θ value is ±0.2.

Another technical solution adopted by the present invention is to provide a quinazoline derivative glycolate crystal form A, whose XRPD pattern has peaks at the following 2θ

Main characteristic peaks: 6.6, 7.4, 17.9
Secondary characteristic peak: 13.3
The error range of the 2θ value is ±0.2.

Preferably, the XRPD pattern of the glycolate crystal form A of the quinazoline derivative provided by the present invention is at 2θ=4.53, 5.89, 6.59, 7.35, 10.02, 12.54, 13.26, 15.94, 17.93, 18.67, 19.36, 19.84, 21.06, 24.99, 31.13, 33.48, 34.79, 35.56, 36.17.

The error range of the above 2θ value is ±0.2.

Another technical solution adopted by the present invention is to provide a quinazoline derivative sulfate crystal form A, whose XRPD pattern has peaks at the following 2θ

Main characteristic peaks: 7.3, 18.2, 15.0
The error range of the 2θ value is ±0.2.

Preferably, the XRPD pattern of the sulfuric acid crystal form A of the quinazoline derivative (I) provided by the present invention is at 2θ=7.27, 8.41, 11.88, 14.96, 18.23, 19.68, 20.64, 24.83, 25.82, 27.10, 28.16, 29.79, 30.71, 32.35, 34.12, 35.56, 37.56, and 38.37.

The error range of the above 2θ value is ±0.2.

Another technical solution adopted by the present invention is to provide a quinazoline derivative oxalate crystal form A, whose XRPD pattern has peaks at the following 2θ

Main characteristic peaks: 6.9, 15.1, 13.7
Secondary characteristic peaks: 15.4, 9.6, 19.0
The characteristic peaks again: 20.6, 27.3, 23.4
The error range of the 2θ value is ±0.2.

Preferably, the XRPD pattern of the oxalate crystal form A of the quinazoline derivative (I) provided by the present invention is at 29-5.43, 6.88, 7.38, 9.56, 13.68, 15.10, 15.43, 16.32, 16.88, 17.68, 18.60, 19.02, 20.58, 21.62, 22.33, 22.70, 23.35, 25.68, 27.29, 27.88, 28.53, 29.37, 31.35, 34.89, 37.11, 37.78, 38.17, 38.36, 39.65.

The error range of the above 2θ value is ±0.2.

Another technical solution adopted by the present invention is to provide a malate crystal form A of a quinazoline derivative, whose XRPD pattern has peaks at the following 2θ

Main characteristic peaks: 6.5, 18.8, 19.9
Secondary characteristic peaks: 7.5, 8.4, 9.2
The error range of the 2θ value is ±0.2.

The XRPD pattern of the malate crystal form A of the quinazoline derivative (I) provided by the present invention is at 2θ=5.43, 6.53, 7.49, 8.35, 9.17, 12.10, 13.16, 16.17, 18.77, 19.85, 20.79, 23.14, 23.94, 26.66, 28.25, 29.32, 30.38, 33.24, 33.69, 34.80, 35.97, 36.87, 37.88.

The error range of the above 2θ value is ±0.2.

Another technical solution adopted by the present invention is to provide a quinazoline derivative benzenesulfonate crystal form A, whose XRPD pattern has peaks at the following 2θ

Main characteristic peaks: 6.6, 14.0, 15.3
Secondary characteristic peaks: 7.1, 5.5, 19.7
Characteristic peaks again: 17.8, 16.9, 21.0
The error range of the 2θ value is ±0.2.

The XRPD pattern of the benzenesulfonate crystal form A of the quinazoline derivative provided by the present invention is at 2θ=5.48, 6.56, 7.08, 7.65, 8.14, 8.48, 9.71, 10.55, 11.14, 11.77, 13.32, 13.95, 15.32, 16.46, 16.89, 17.82, 19.15, 19.70, 20.43, 21.02, 21.98, 22.68, 23.23, 25.26, 26.07, 26.59, 28.63, 29.09, 30.45, 31.12, 32.09, 32.55, 33.66, 35.76, 37.86, 38.67, 39.11.

The error range of the above 2θ value is ±0.2.

Another technical solution adopted by the present invention is to provide a quinazoline derivative benzenesulfonate crystal form B, whose XRPD pattern has peaks at the following 2θ

Main characteristic peaks: 8.5, 14.5, 23.4
Secondary characteristic peaks: 18.3, 19.7
The error range of the 2θ value is ±0.2.

The XRPD pattern of the benzenesulfonate crystal form B of the quinazoline derivative provided by the present invention is at 2θ=5.50, 6.32, 7.28, 8.50, 9.74, 10.79, 11.55, 13.22, 14.49, 15.53, 16.26, 16.97, 18.29, 19.71, 21.36, 22.21, 23.44, 24.19, 25.34, 25.87, 27.16.

The error range of the above 2θ value is ±0.2.

Another technical solution adopted by the present invention is to provide a quinazoline derivative benzenesulfonate crystal form C, whose XRPD pattern has peaks at the following 2θ

Main characteristic peaks: 14.0, 14.7, 7.7
Secondary characteristic peaks: 8.3, 21.2, 19.4
Characteristic peak again: 27.5, 24.7
The error range of the 2θ value is ±0.2.

Preferably, the XRPD pattern of the benzenesulfonate crystal form C of the quinazoline derivative (I) provided by the present invention is at 2θ=4.24, 7.07, 7.68, 8.31, 9.92, 12.55, 14.03, 14.74, 18.72, 19.40, 20.36, 21.19, 24.08, 24.73, 26.14, 27.49, 28.28, 31.68, 33.90, 34.82, 35.06, 35.78, 36.54, 37.57, 37.89, 38.36, 39.0.

The error range of the above 2θ value is ±0.2.

Another technical solution adopted by the present invention is to provide a quinazoline derivative benzoate crystal form A, whose XRPD pattern has peaks at the following 2θ

Main characteristic peaks: 7.3, 6.3, 16.8
Secondary characteristic peaks: 13.5, 18.7, 27.0
The error range of the 2θ value is ±0.2.

The XRPD pattern of the benzoate crystal form A of the quinazoline derivative (I) provided by the present invention is at 2θ=4.45, 6.31, 6.65, 7.33, 7.69, 8.01, 11.85, 13.53, 16.02, 16.77, 18.75, 19.95, 21.06, 21.76, 22.56, 23.41, 26.94, 27.44, 27.61, 27.98, 28.55, 29.05, 31.92, 32.29, 32.93, 33.72, 34.61, 35.35, 35.95, 37.08, 38.13, 39.62.

The error range of the above 2θ value It is +0.2.

Another technical solution adopted by the present invention is to provide a hippurate crystal form A of a quinazoline derivative, whose XRPD pattern has peaks at the following 2θ

Main characteristic peaks: 5.6, 6.9, 20.0
Secondary characteristic peaks: 16.0, 7.7, 13.7
Characteristic peak again: 24.3, 26.4
The error range of the 2θ value is ±0.2.

Preferably, the XRPD pattern of hippurate crystal form A of the quinazoline derivative (I) provided by the present invention is at 2θ=4.35, 5.59, 6.85, 7.74, 9.17, 9.95, 13.74, 14.73, 15.96, 16.44, 18.10, 18.63, 19.96, 21.38, 24.25, 25.37, 25.72, 26.39, 27.23, 28.56, 30.25, 30.82, 33.31, 34.58, 35.29, 36.39, 37.24, 37.9.

The error range of the above 2θ value is ±0.2.

Another technical solution adopted by the present invention is to provide a quinazoline derivative oxalate crystal form A, whose XRPD pattern has peaks at the following 2θ

Main characteristic peaks: 6.4, 9.1, 17.5
Secondary characteristic peaks: 12.9, 14.5, 26.4
Characteristic peaks again: 19.4, 18.3, 15.9
The error range of the 2θ value is ±0.2.

Preferably, the XRPD pattern of the oxalate crystal form A of the quinazoline derivative (I) provided by the present invention is at 2θ=4.11, 6.44, 7.15, 8.75, 9.06, 9.88, 11.26, 11.58, 12.92, 14.52, 15.87, 17.47, 18.29, 19.43, 20.14, 20.49, 23.70, 24.34, 26.36, 26.92, 29.75, 31.72, 32.67, 32.99, 34.21, 34.52, 34.86, 36.36, 36.91, 37.91, 39.03.

The error range of the above 2θ value It is 10.2.

Preferably, the hydrochloride crystal form A of the quinazoline derivative of the present invention has an XRPD pattern substantially as shown in FIG. 1.

Preferably, the hydrochloride crystal form B of the quinazoline derivative of the present invention has an XRPD pattern substantially as shown in FIG. 2.

Preferably, the hydrochloride crystal form C of the quinazoline derivative of the present invention has an XRPD pattern substantially as shown in FIG. 10.

Preferably, the hydrochloride crystal form D of the quinazoline derivative of the present invention has an XRPD pattern substantially as shown in FIG. 11.

Preferably, the hydrochloride crystal for F of the quinazoline derivative of the present invention has an XRPD pattern substantially as shown in FIG. 9.

Preferably, the hydrochloride crystal form H of the quinazoline derivative of the present invention has an XRPD pattern substantially as shown in FIG. 3.

Preferably, the hydrochloride crystal form I of the quinazoline derivative of the present invention has an XRPD pattern substantially as shown in FIG. 4.

Preferably, the fumarate crystal form A of the quinazoline derivative of the present invention has an XRPD pattern substantially as shown in FIG. 5.

Preferably, the succinate crystal form A of the quinazoline derivative of the present invention has an XRPD pattern substantially as shown in FIG. 6.

Preferably, the maleate crystal form A of the quinazoline derivative of the present invention has an XRPD pattern substantially as shown in FIG. 7.

Preferably, the glycolate crystal form A of the quinazoline derivative of the present invention has an XRPD pattern substantially as shown in FIG. 8.

Preferably, the sulfate crystal form A of the quinazoline derivative of the present invention has an XRPD pattern substantially as shown in FIG. 12.

Preferably, the oxalate crystal form A of the quinazoline derivative of the present invention has an XRPD pattern substantially as shown in FIG. 13.

Preferably, the malate crystal form A of the quinazoline derivative of the present invention has an XRPD pattern substantially as shown in FIG. 14.

Preferably, the benzenesulfonate crystal form A of the quinazoline derivative of the present invention has an XRPD pattern substantially as shown in FIG. 15.

Preferably, the benzenesulfonate crystal form B of the quinazoline derivative of the present invention has an XRPD pattern substantially as shown in FIG. 16.

Preferably, the benzenesulfonate crystal form C of the quinazoline derivative of the present invention has an XRPD pattern substantially as shown in FIG. 17.

Preferably, the benzoate crystal form A of the quinazoline derivative of the present invention has an XRPD pattern substantially as shown in FIG. 18.

Preferably, the hippurate crystal form A of the quinazoline derivative of the present invention has an XRPD pattern substantially as shown in FIG. 19.

Preferably, the oxalate crystal form I of the quinazoline derivative of the present invention has an XRPD pattern substantially as shown in FIG. 20.

The present invention also provides a method for preparing the hydrochloride crystal form A of the quinazoline derivative (I) of the present invention, which comprises the following steps: adding 0.8 to 1.2 equivalents of an organic solvent and hydrochloric acid to the formula (I) of the quinazoline derivative sample, stir at 22-28 degrees Celsius, and the lower solid is separated by centrifugation to obtain crystal form A; wherein, 10 to 200 mg of the quinazoline derivative represented by formula (I) is added per milliliter of organic solvent.

The present invention also provides a method for preparing the hydrochloride crystal form B of the quinazoline derivative (I) of the present invention, which comprises the following steps: adding the quinazoline derivative represented by formula (I) to an organic solvent, and then adding 0.8-1.2 equivalent of hydrochloric acid to the suspension, stir at 22-28 degrees Celsius, centrifuge to separate the wet solid of the lower layer to obtain crystal form B; wherein, per milliliter of organic solvent is added the quinazoline derivative of formula (I) 10~200 mg.

The present invention also provides a method for preparing the hydrochloride crystal form C of the quinazoline derivative (I) of the present invention, which comprises the following steps: adding a sample of the quinazoline derivative represented by formula (I) to an organic solvent and 2-2.5 equivalents of hydrochloric acid, stir at 22-28 degrees Celsius, and centrifuge to separate the lower wet sample solid to obtain the dihydrochloride crystal form C; wherein, per milliliter of organic solvent is added the quinazoline derivative represented by formula (I) 10~200 mg.

The present invention also provides a method for preparing the hydrochloride crystal form D of the quinazoline derivative (I) of the present invention, which comprises the following steps: heating the hydrochloride crystal form C sample to a high temperature and then cooling it to 22-28 degrees Celsius, crystal form D of the dihydrochloride salt was obtained.

The present invention also provides a method for preparing the hydrochloride crystal form F of the quinazoline derivative (I) of the present invention, which comprises the following steps: Adding alcohol and ester organic solvents to hydrochloride crystalline form B of the quinazoline derivative represented by formula (I), and diffuse gas-liquid at 22-28 degrees Celsius until a solid is precipitated to obtain crystalline form F; wherein per milliliter of organic solvent is added the hydrochloride crystal form B represented by formula (I) 10~200 mg.

The present invention also provides a method for preparing the hydrochloride crystal form H of the quinazoline derivative (I) of the present invention. The crystal form H is volatilized at −28 degrees Celsius (rapidly open); among them, 10 to 200 mg of the hydrochloride crystal form B represented by formula (I) is added to each milliliter of organic solvent.

The present invention also provides a method for preparing the hydrochloride crystal form I of the quinazoline derivative (I) of the present invention, which comprises the following steps: heating the hydrochloride crystal form H sample to a high temperature and then cooling to 22-28 Celsius.

The present invention also provides a method for preparing the fumarate crystal form A of the quinazoline derivative (I) of the present invention, which comprises the following steps: the quinazoline derivative represented by formula (I) and 0.4-0.6 equivalent of fumaric acid are added to the organic solvent, the mixture is stirred at 22-28 degrees Celsius, and the solid is collected by centrifugation; wherein, 10 to 200 mg of the quinazoline derivative represented by formula (I) is added to each milliliter of organic solvent.

The present invention also provides a method for preparing the succinate crystal form A of the quinazoline derivative (I) of the present invention, which comprises the following steps: the quinazoline derivative represented by formula (I) and 0.8-1.2 equivalent amount of succinic acid are added to the organic solvent, stirring at 22-28 degrees Celsius, centrifugation to collect the solid to obtain the crystal form; wherein, 10 to 200 mg of the quinazoline derivative represented by formula (I) is added to each milliliter of organic solvent.

The present invention also provides a method for preparing the maleate crystal form A of the quinazoline derivative (I) of the present invention, including the following steps: the quinazoline derivative represented by formula (I) and the maleate acid are added to the organic solvent, the mixture is stirred at 22-28 degrees Celsius, and the solid is collected by centrifugation to obtain the crystal form; wherein, 10 to 200 mg of the quinazoline derivative represented by formula (I) is added to each milliliter of organic solvent.

The present invention also provides a method for preparing the glycolate crystal form A of the quinazoline derivative (I) of the present invention, which comprises the following steps: the quinazoline derivative represented by formula (I) and 0.8-1.2 equivalent amount of glycolic acid are added to the organic solvent, stir at room temperature and centrifuge to collect the solid.

The present invention also provides a method for preparing the sulfate crystal form A of the quinazoline derivative (I) of the present invention, which comprises the following steps: adding a sample of the quinazoline derivative represented by formula (I) to an organic solvent and 0.8-1.2 equivalent sulfuric acid aqueous solution, stir at 22-28 degrees Celsius, and the solid is collected by centrifugation to obtain the crystal form; wherein, 10 to 200 mg of the quinazoline derivative represented by formula (I) is added to each milliliter of organic solvent.

The present invention also provides a method for preparing the oxalate crystal form A of the quinazoline derivative (I) of the present invention, which comprises the following steps: adding a sample of the quinazoline derivative represented by formula (I) to organic solvent and 0.8-1.2 equivalent of oxalic acid, stir at 22-28 degrees Celsius, and the solid is collected by centrifugation to obtain the crystal form: wherein, 10 to 200 mg of the quinazoline derivative represented by formula (I) is added to each milliliter of organic solvent.

The present invention also provides a method for preparing the malate crystal form A of the quinazoline derivative (I) of the present invention, which comprises the following steps: adding a sample of the quinazoline derivative represented by formula (I) to an organic solvent and 0.8-1.2 equivalents of malic acid under stirring at 22-28 degrees Celsius, and centrifugation to collect the solid to obtain the crystal form: wherein, 10 to 200 mg of the quinazoline derivative represented by formula (I) is added to each milliliter of organic solvent.

The present invention also provides a method for preparing the benzenesulfonate crystal form A of the quinazoline derivative (I) of the present invention, which comprises the following steps: adding a sample of the quinazoline derivative represented by formula (I) to the organic solvent and 0.8-1.2 equivalent of benzenesulfonic acid, stir at 22-28 degrees Celsius, and the solid is collected by centrifugation to obtain the crystal form; wherein, 10 to 200 mg of the quinazoline derivative represented by formula (I) is added to each milliliter of organic solvent.

The present invention also provides a method for preparing the benzenesulfonate crystal form B of the quinazoline derivative (I) of the present invention, which comprises the following steps: adding a sample of the quinazoline derivative represented by formula (I) to the organic solvent and 0.8-1.2 equivalent of benzenesulfonic acid, stir at 22-28 degrees Celsius, and the solid is collected by centrifugation to obtain the crystal form; wherein, 10 to 200 mg of the quinazoline derivative represented by formula (I) is added to each milliliter of organic solvent.

The present invention also provides a method for preparing the benzenesulfonate crystal form C of the quinazoline derivative (I) of the present invention, which comprises the following steps: adding a sample of the quinazoline derivative represented by formula (I) to an organic solvent and 0.8-1.2 equivalent of benzenesulfonic acid, stir at 22-28 degrees Celsius, and the solid is collected by centrifugation to obtain the crystal form: wherein, 10 to 200 mg of the quinazoline derivative represented by formula (I) is added to each milliliter of organic solvent.

The present invention also provides a method for preparing the benzoate crystal form A of the quinazoline derivative (I) of the present invention, which comprises the following steps: adding a sample of the quinazoline derivative represented by formula (I) to an organic solvent and 0.8-1.2 equivalent of benzoic acid, stir at 22-28 degrees Celsius, and the solid is collected by centrifugation to obtain the crystal form; wherein, 10 to 200 mg of the quinazoline derivative represented by formula (I) is added to each milliliter of organic solvent.

The present invention also provides a method for preparing the hippurate crystal form A of the quinazoline derivative (I) of the present invention, which comprises the following steps: adding a sample of the quinazoline derivative represented by formula (I) to organic solvent and 0.8-1.2 equivalent hippuric acid, stir at 22-28 degrees Celsius, and the solid is collected by centrifugation to obtain the crystal form; wherein, 10 to 200 mg of the quinazoline derivative represented by formula (I) is added to each milliliter of organic solvent.

The present invention also provides a method for preparing the oxalate crystal form A of the quinazoline derivative (I) of the present invention, which comprises the following steps: adding a sample of the quinazoline derivative represented by formula (I) to an organic solvent and 0.8-1.2 equivalent of oxalic acid under stirring at 22-28 degrees Celsius, centrifugation to collect the solid to obtain the crystal form; wherein, 10 to 200 mg of the quinazoline derivative represented by formula (I) is added to each ml of organic solvent.

In the above method, preferably, the organic solvent is one or more of alcohols, ethers, esters, aliphatic hydrocarbons, and aromatic hydrocarbons.

More preferably, the alcoholic organic solvent is one or more of methanol, ethanol, isopropanol, n-propanol, isobutanol, and n-butanol.

More preferably, the ether organic solvent is diethyl ether, isopropyl ether or methyl tert-butyl ether.

More preferably, the ester organic solvent is ethyl acetate, butyl acetate or isopropyl acetate.

More preferably, the ketone organic solvent is acetone, methyl ethyl ketone or 4-methyl-2-pentanone.

More preferably, the aliphatic hydrocarbon organic solvent is n-heptane or acetonitrile.

More preferably, the aromatic hydrocarbon organic solvent is toluene.

Further preferably, in the preparation method of the hydrochloride crystal form A of the quinazoline derivative (I), preferably the organic solvent is methanol.

In the preparation method of the hydrochloride crystal form B of the quinazoline derivative (I), the organic solvent is preferably acetonitrile, ethyl acetate or tetrahydrofuran/water (15-20/1, v/v).

In the preparation method of the hydrochloride crystal form C of the quinazoline derivative (I), the organic solvent is preferably acetone.

The method for preparing the hydrochloride crystal form D of the quinazoline derivative (I) preferably has a high temperature range of 120-160 degrees Celsius.

In the preparation method of the hydrochloride crystal form F of the quinazoline derivative (I), preferably, the alcohol is methanol and the ester is isopropyl acetate. More preferably, the weight ratio of methanol to ethyl acetate is 1:1.

In the preparation method of the hydrochloride crystal form H of the quinazoline derivative (I), the organic solvent is preferably ethanol.

The method for preparing the hydrochloride crystal form I of the quinazoline derivative (I) preferably has a high temperature of 120-130 degrees Celsius.

In the preparation method of the fumarate crystal form A of the quinazoline derivative (I), preferably, the organic solvent is methanol, acetone, ethyl acetate or a tetrahydrofuran/water mixture with a volume ratio of 15-20:1.

In the preparation method of the succinate crystal form A of the quinazoline derivative (I), preferably, the organic solvent is methanol or acetone.

In the method for preparing maleate crystal form A of the quinazoline derivative (I), preferably, the organic solvent is acetone.

In the preparation method of the glycolate crystal form A of the quinazoline derivative (I), the organic solvent is preferably methanol, acetonitrile or ethyl acetate.

In the preparation method of the sulfate salt crystal form A of the quinazoline derivative (I), the organic solvent is preferably methanol, acetonitrile, acetone, ethyl acetate or a tetrahydrofuran/water mixture with a volume ratio of 15-20:1.

In the preparation method of the oxalate crystal form A of the quinazoline derivative (I), preferably, the organic solvent is methanol or ethyl acetate.

In the preparation method of the malate crystal form A of the quinazoline derivative (I), preferably, the organic solvent is methanol, ethyl acetate or a tetrahydrofuran/water mixture with a volume ratio of 15-20:1.

In the method for preparing the benzenesulfonate crystal form A of the quinazoline derivative (I), preferably, the organic solvent is methanol.

In the preparation method of the benzenesulfonate crystal form B of the quinazoline derivative (I), the organic solvent is preferably acetonitrile.

In the preparation method of the benzenesulfonate crystal form C of the quinazoline derivative (I), the organic solvent is preferably a mixed solvent of tetrahydrofuran and water (volume ratio is 15-20:1, more preferably 19:1).

In the preparation method of the benzoate crystal form A of the quinazoline derivative (I), the organic solvent is preferably methanol, acetonitrile, acetone or a tetrahydrofuran/water mixture with a volume ratio of 15-20:1.

In the preparation method of hippurate crystal form A of the quinazoline derivative (I), preferably, the organic solvent is methanol.

In the preparation method of the oxalate crystal form A of the quinazoline derivative (I), preferably, the organic solvent is methanol.

The present invention also provides a pharmaceutical composition comprising the hydrochloride crystal form A, B, C, D. F. H. I, sulfate of the quinazoline derivative represented by formula (I) Form A. Maleate Form A, Succinate Form A. Adipate Form A, Glycolate Form A, Malate Form A. Fumarate Form A, Benzene Sulfonate crystal forms A, B. C, benzoate crystal form A, hippurate crystal form A and oxalate crystal form A or their combination, and pharmaceutically acceptable excipients or auxiliary components.

Preferably, the adjuvants or auxiliary components include carriers, excipients, diluents, vehicles, and adjuvants.

The present invention also provides a hydrochloride crystal form A, B, C, D, F, H, I, sulfate crystal form A, maleate crystal form of the quinazoline derivative represented by formula (I) Form A, Succinate Form A. Adipate Form A. Glycolate Form A. Malate Form A, Fumarate Form A, Besylate Form A. B. C, Benzoate crystal form A, hippurate crystal form A and oxalate crystal form A or the abovementioned pharmaceutical composition in the preparation of a medicine for the treatment or prevention of diseases mediated by the epidermal growth factor receptor EGFR protein the use of.

Preferably, the drug is a drug for the treatment or prevention of diseases mediated by the epidermal growth factor receptor EGFR protein and caused by EGFRVIII activation mutations.

The drug is a drug for the treatment or prevention of diseases that are mediated by the epidermal growth factor receptor EGFR protein and are caused by EGFR Del19 and/or EGFR L858R activation mutations.

More preferably, the medication is prepared for the treatment or prevention of non-small cell lung cancer brain metastasis, meningeal metastasis, head and neck squamous cell carcinoma, squamous cell carcinoma, brain stem tumor, primary brain cancer or glioma.

A person of ordinary skill in the art can adjust the dosage and method of the reagents used in the present invention based on their knowledge and experience, including scaling up or down the amount of raw materials or solvents, and these adjustment schemes are also included in the method of the present invention. Compared with the prior art, the present invention has the following beneficial effects: 1) The novel chiral R quinazoline derivative (I) and its pharmaceutical salt of the present invention have unexpected ability to cross the blood-brain barrier and can be used as protein kinase inhibitors, especially for medical conditions mediated by certain forms of activating mutations of the epidermal growth factor receptor (for example, activating mutants with deletion of exons 2-7 of the epidermal growth receptor EGFR), for example, gliomas with EGFRVIII mutations, and can be used to treat or prevent disorders related to abnormal protein kinase activity, such as cancer, cancer with brain metastasis, cancer with meningeal metastasis, and central nervous system diseases. 2) The quinazoline derivative (I) and its pharmaceutical salt of the present invention have a low efflux rate, are not a P-glycoprotein efflux enzyme substrate, or a breast cancer drug-resistant efflux enzyme substrate, and can reduce the efflux resulting resistance. 3) The quinazoline derivative and its pharmaceutical salt of the present invention have good pharmacokinetics and high biological activity, which can reduce the patient's tablet intake burden and improve the patient's tablet intake compliance. 4) The hydrochloride crystal form A, B, C, D, F, H, I, sulfate crystal form A, maleate crystal form A of the quinazoline derivative (I) of the present invention provided by the present invention, Succinate crystal form A, adipate crystal form A, glycolate crystal form A, malate crystal form A, fumarate crystal form A, besylate crystal form A, B, C, benzene Formate crystal form A, hippurate crystal form A and oxalate crystal form A have good stability and water solubility, which are beneficial to use in pharmaceutical processing and pharmaceutical compositions, and can treat EGFR activating mutations (such as, EGFRVIII. EGFR del19 or EGFR L858R) mediated cancer, for example, non-small cell lung cancer brain metastasis, meningeal metastasis, head and neck squamous cell carcinoma, squamous cell carcinoma, brain stem tumor, primary brain cancer or gliomas, etc., and has good bioavailability, while providing qualitative and quantitative information on efficacy and safety, is of great significance for further research on the efficacy of such solid drugs.

BRIEF DESCRIPTION OF THE DRAWINGS

By reading the detailed description of the non-limiting embodiments with reference to the following drawings, other features, purposes and advantages of the present invention will become more apparent:

FIG. 23A and FIG. 23B are the TGA and DSC spectra of the quinazoline derivative fumarate salt of the present invention; wherein FIG. 23A is the TGA spectra without significant weight loss; FIG. 23B is the DSC spectra, the crystal form is stable during heating, and the crystal form has not changed, The melting point is 240 degrees Celsius;

DETAILED DESCRIPTION OF THE EMBODIMENTS

Figure 1:
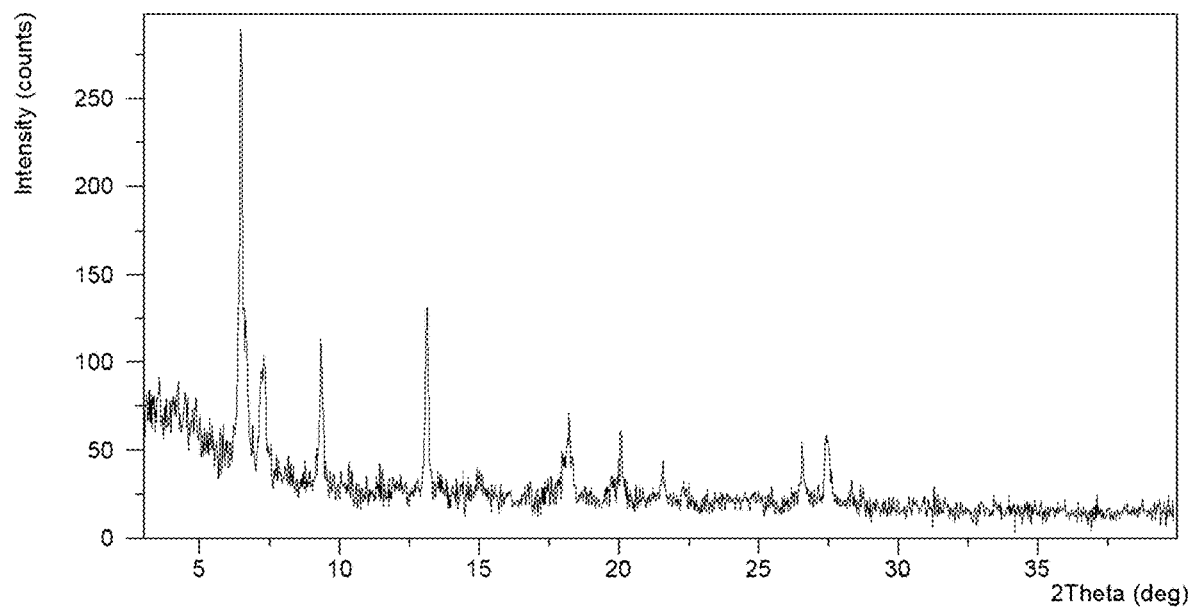
FIG. 1 is the XRPD pattern of the hydrochloride crystal form A of the quinazoline derivative of the present invention.

The terms of the present invention are explained as follows:

The terms "improving" and "treating" are used interchangeably to mean reducing, inhibiting, preventing or stabilizing the occurrence or progression of a disease (e.g., the disease or disorder described herein), in addition to, but not limited to, therapeutic benefits and/or prophylactic benefits.

"Disease" refers to any disorder or disorder that damages or interferes with the normal functioning of a cell, organ or tissue.

"marker" refers to any alteration associated with a disease or disorder. For example, any protein or polynucleic acid that has altered the expression level or activity associated with the disease or disorder.

In this context, "including". "containing" and "possessed" and similar terms have the meanings given to them in the patent law; "substantially consisting" or "essentially" has the same meaning as given in the patent law, and the term is open, allowing the presence of objects other than the cited object as long as the basis or new feature of the referenced object does not change due to the presence of an object other than the cited object, but does not include the implementation of the prior art. The terms "antagonists" and "inhibitors" as used herein are used interchangeably and refer to the ability of a compound or agent to inhibit the biological function of a target protein or polypeptide, for example by inhibiting the activity or expression of a protein or polypeptide. Although some of the antagonists herein interact with specific target proteins or polypeptides (e.g., bind to EGFR), the compounds also inhibit the biological activity of the target protein or polypeptide by interacting with other members of the signal transduction pathway that targets the protein or polypeptide Including within the definition, those that inhibit the development of tumors that develop, grow, or diffuse, or that are associated with unwanted immune responses exhibited by autoimmune diseases.

The term "anti-cancer agent". "antineoplastic agent" or "chemotherapeutic agent" as used herein refers to any agent useful in the treatment of a tumor disorder. A class of anticancer agents includes chemotherapeutic agents. "Chemotherapy" refers to one or more chemotherapeutic agents and/or other agents administered in a variety of ways, including intravenous, oral, subcutaneous, intramuscular, intraperitoneal, intravesical, transdermal, buccal, or inhaled way.

As used herein, the term "cell proliferation" refers to an increase in the number of cells as a result of cell division, as well as cell growth (e.g., increased size) that is consistent with the proliferation signal by the cell morphology.

As used herein, the term "co-administration" refers to the use of two or more drugs at the same time, as well as compositions that are present at the same time using two or more agents, as well as at different times administering or administering two or more drugs and/or their metabolites alone.

As used herein, the term "effective amount" or "effective therapeutic amount" means that the amount of the compound or pharmaceutical composition described herein is sufficient to achieve the intended use, including, but not limited to, treating the disease. In some embodiments, the amount is detected to be effective for killing or inhibiting the growth or spread of cancer cells; the size or number of tumors; or the severity level, stage and progression of cancer. The amount of effective treatment may vary depending on the intended application, such as in vitro or in vivo, condition and severity of the disease, subject age, weight, or mode of administration. The term also applies to dosages that will induce target cells, for example, to reduce cell migration by a specific response. The specific dosage will depend on, for example, the particular compound selected, the subject species and their age/existing health status or health status, the route of administration, the severity of the disease, the combination with other agents, The administration time, the tissue to which it is administered, and the administration device.

The term "therapeutic effect" as used herein includes therapeutic benefits and/or prophylactic benefits. The prophylactic effect includes delaying or eliminating the onset of a disease or condition, delaying or eliminating the onset of symptoms or disorders of the disease, slowing, stopping or reversing a disease or condition, or any combination thereof.

As used herein, the term "signal transduction" is the process by which a stimulus of suppression signal is sent to the cell to initiate an intracellular response. The "modulator" of the signal transduction pathway means that the compound modulates one or more activity of cellular proteins that are mediated by specific signal transduction pathways. The "modulator" may increase (agonist) the activity of the signaling molecules or inhibit (antagonist) signaling molecules.

The term "selective inhibition" as used herein refers to the ability of a compound to selectively reduce the target signaling activity compared to the target activity for off-target, by direct interaction or indirect interaction. For example, the activity of a compound to selectively inhibit mutant EGFR is at least about 2 times, about 3 times, about 5 times, about 10 times, about 20 times, about 50 times, about 100 times or more for the activity of wild type EGFR.

As used herein, the term "radiation therapy" refers to a subject that is exposed to a radiation emitter, such as, but not limited to, alpha-particles emitting radioactive nuclear elements (e.g., actinium and thorium radioactive nuclear elements) (e.g., beta emitters), conversion electron emitters (e.g., strontium-89 and samarium 153-EDTMP), or high energy radiation including, but not limited to, X-rays, gamma rays, and neutrons.

The term "subject" as used herein includes, but is not limited to, humans (e.g., any age group, e.g., a male or female (e.g., infant, child, adolescent) or adult subject (e.g., young adult, middle-aged adult or senior adult)) and/or other primates (e.g., cynomolgus monkeys, rhesus monkeys); mammals, including commercial-related mammals such as cattle, sheep, goats, pigs, horses, cats and/or dogs; and/or birds, including commercial-related birds such as chickens, geese, quails, ducks and/or turkeys.

As used herein, the term "in vivo" refers to an activity occurring within the subject body. Incident in rodents, such as rats, mice, guinea pigs, and the like, are also included in the body.

As used herein, the term "in vitro" refers to an event that occurs outside a body. For example, in vitro test involves any detection that occurs outside the body. In vitro assays include cell determination based on live or dead cells, as well as cell-free assays that are used in cells that are not intact.

The term "compound" as used herein is also intended to include salts, prodrugs and prodrugs of the compounds of the general formula herein. The term also includes any solvate, hydrate and polymorph of any of the foregoing. In certain aspects of the invention described in this application, specific references to "prodrugs". "prednisone", "solvate", "hydrate" or "polymorph" should not be construed. In other aspects of the invention that use the term "compound" without reference to these other forms, it is not intended to exclude such forms.

The salts of the compounds of the present invention are formed between the acid and the basic group of the compound, for example, the amino functional group. According to another preferred embodiment, the compound is a pharmaceutically acceptable acid addition salt.

The salts of the compounds of the present invention are formed between the base and the acidic groups of the compound, for example, the carboxyl functional groups. According to another preferred embodiment, the compound is a pharmaceutically acceptable base addition salt.

As used herein and unless otherwise indicated, the term "prodrug" refers to a derivative of a compound that can be hydrolyzed, oxidized or otherwise reacted under biological conditions (in vitro or in vivo) to provide the compounds of the present invention. The prodrug may become active only after such a reaction under biological conditions or may be active in its unreacted form. Examples of prodrugs of the invention include, but are not limited to, analogs or derivatives of any of the compounds of the general formula disclosed herein, as well as biologically hydrolyzable moieties such as amides and ester analogs.

The prodrug salt is a compound formed between an acid group of an acid and a prodrug, such as an amino functional group, or an acidic group of a base with a prodrug, such as a carboxyl functional group. In one embodiment, the prodrug salt is a pharmaceutically acceptable salt Particularly preferred prodrugs and prodrug salts are those that increase the bioavailability of the compounds of the present invention when such compounds are used in mammals or humans (e.g., by more easily being absorbed by oral administration of the compound) or relative to the parent species Promoting the delivery of compounds to biological chambers (e.g., the brain or central nervous system). Preferred prodrugs include derivatives wherein the groups that will increase water solubility or increase the active transport through the intestinal membrane are added to the general structure described herein. See, for example, H. Bundgaard. Advanced Drug Delivery Reviews, 8, 1-38 (1992); and N. Kakeya, et al., Chem Pharm Bull. 32, 692 (1984).

The term "pharmaceutically acceptable" as used herein refers to a pharmaceutical composition that is suitable for use in contact with humans and other mammalian tissues without reasonable toxicity, irritation, allergic reactions, etc., and has reasonable interest/risk than the components. "Pharmaceutically acceptable salt" refers to any non-toxic salt that, upon administration to a recipient, can provide the prodrug of a compound or compound of the invention, either directly or indirectly.

The acids commonly used to form pharmaceutically acceptable salts include inorganic acids such as hydrochloric acid, hydrobromic acid, sulfuric acid, hydroiodic acid and phosphoric acid, and organic acids such as trifluoroacetic acid, citric acid, maleic acid, oxalic acid, picric acid Acetic acid, adipic acid, alginic acid, aspartic acid, sulfuric acid, boric acid, butyric acid, valeric acid, camphoric acid, camphorsyl thiocyanate, digluconic acid, dodecyl sulfate, pivalic acid, formic acid, fumaric acid, hydroiodic acid, benzoic acid, 2-hydroxy-ethanesulfonic acid, fumaric acid, stearic acid, lactobionic acid, propionic acid lauric acid, oleic acid, nicotinic acid, lactic acid cinnamic acid, amber acid, mandelic acid, malic acid, tartaric acid, tartaric acid, lactic acid, pyruvic acid, pectic acid, methanesulfonic acid, pamoate, benzenesulfonic acid, persulfuric acid, palmitic acid, malonic acid, glycerophosphoric acid, 2-naphthalenesulfonic acid, P-toluenesulfonic acid, salicylic acid, ascorbic acid, 3-phenylpropionic acid, gluconic acid, glucuronic acid, phosphoric acid, glutamic acid, ethanesulfonic acid, p-bromobenzenesulfonic acid and carbonic acid, and related inorganic and organic acid. Alkalides commonly used to form pharmaceutically acceptable salts include alkali metals, alkaline earth metals, ammonium salts, $N^+(C1-4\ alkyl)_4$ salts, and related inorganic and organic bases. Examples of the alkali metal and alkaline earth metals such as sodium, lithium, potassium, calcium, magnesium, iron, copper, manganese, zinc, aluminum and the like, and salts of organic bases include, for example, primary, secondary and tertiary amines, naturally occurring substituted amines, cyclic amines, basic ion exchange resins, and the like, such as isopropylamine, trimethylamine, diethylamine, triethylamine, tripropylamine and ethanolamine. In some embodiments, the pharmaceutically acceptable base addition salts may be selected from ammonium, potassium, sodium, calcium and magnesium salts. See, e.g., Berge et al. J. Pharmaceutical Sciences (1977) 66:1-19.

As used herein, the term "hydrate" refers to a compound that includes stoichiometric or non-stoichiometric amounts of water bound by noncovalent intermolecular forces. The term "solvate" as used herein refers to a compound comprising a stoichiometric or non-stoichiometric amount of a solvent that is bound by non-covalent intermolecular forces such as water, dichloromethane, 2-propanol, acetone, methanol, ethanol or the like. Pharmaceutically acceptable solvates and hydrates are complexes that may include, for example, I to about 100, or 1 to about 10, or 1 to about 4, about 3, or about 2, a solvent or water molecule. It is to be understood that the term "compound" as used herein includes solvates, hydrates, and mixtures thereof of the compounds and compounds described.

The term "polymorph" as used herein refers to a solid crystalline form of a compound or a complex thereof. Different polymorphs of the same compound can exhibit different physical, chemical and/or spectral properties. Different physical properties include, but are not limited to, stability (e.g., heat, light or moisture), density, hygroscopicity, solubility, compressibility and dissolution rate.

The term "isomer" as used herein is a different compound having the same molecular formula. "Stereoisomers" are isomers only in the arrangement of atoms in different ways. The term "isomer" as used herein includes any and all geometric isomers and stereoisomers. For example. "isomers" include geometrical double bonds of cis and trans isomers, also known as E- and Z-isomers; R- and S-enantiomers; diastereomers, (D) Isomers and (L) isomers, their racemic mixtures, and other mixtures thereof, are disclosed herein.

The double bond around the carbon-carbon substituent is designated as the "Z" or "E" configuration, where the terms "Z" and "E" are used according to the IUPAC standard. Unless otherwise indicated, the structure depicts both the "E" and "Z" isomers.

The substitutable substituents surrounding the carbon-carbon double bonds may be referred to as "cis" or "trans", where "cis" means substituents on the same side of the double bond, and "trans" represents substituents on both sides. The arrangement of the surrounding carbon rings of the substituents may also be designated as "cis" or "trans". The term "cis" means the same side substituents in the ring plane, and the term "trans" means the substituents on both sides of the ring plane. Wherein the mixture of substituents on the same and opposite side of the plane of the two rings is represented as "cis/trans".

The term "enantiomer" as used herein is a stereoisomer of a pair of non-overlapping mirrors that are mutually overlapping. A mixture of enantiomers in any proportion may be referred to as a "racemic" mixture. The term "(+)" is used to specify the racemic mixture as appropriate. "Diastereomer" refers to a mirror image having at least two asymmetric atoms but whose stereoisomers are not each other. Absolute stereochemistry is specified according to the Cahn-Ingold-Prelog R-S system. When the compound is enantiomer, the stereochemistry of each chiral carbon can be specified by R or S. The absolute configuration of the compound is unknown and can be specified (+) or (−), depending on their direction of rotation of the polarized light in the wavelength of the sodium D line (right or left). Some of the materials described herein contain one or more asymmetric centers, and thus can produce enantiomers, diastereomers, and other stereoisomeric forms can be defined, in absolute stereologies for each asymmetric atom (R)- or (S)-, the pharmaceutical compositions and methods include all of these possible isomers, including racemic mixtures, optically pure forms and intermediate mixtures. The optically active (R)- and (S)- may also be prepared using chiral synthetic methods or chiral reagents, or by conventional techniques.

The term "enantiomeric excess" or "enantiomeric excess" as used herein can be calculated using the formula shown below. In the examples shown below, the composition contains 90% of one enantiomer, for example, the S enantiomer, and contains 10% of the other enantiomer, for example, the R enantiomer.

$$ee \text{ value} = (90-10)/100 = 80\%.$$

Thus, a composition containing 90% of one enantiomer and 10% of the other enantiomer is said to have an enantiomeric excess of 80%. Some of the compositions described herein contain at least about 50% enantiomeric excess, about 75%, about 90%, about 95%, or about 99% of the S enantiomer. In other words, the composition comprises an enantiomeric excess of the S enantiomer in the R enantiomer. In other embodiments, some of the compositions described herein contain at least about 50% enantiomeric excess, about 75%, about 90%, about 95%, or about 99% of the R enantiomer. In other words, the composition comprises an enantiomeric excess of the R enantiomer in the S enantiomer. For example, an isomer/enantiomer may, in some embodiments, provide the ee value of the corresponding enantiomer, and may also be referred to as "optical enrichment", "enantiomerically enriched", "enantiomerically pure" and "non-racemic", which are used interchangeably herein. These terms mean that the weight percentage of one of the enantiomers is greater than the amount of the control mixture of the composition than the racemic composition in one enantiomer (e.g., greater than 1:1 by weight). For example, the enantiomerically enantiomer of the S enantiomer is present at about 75% by weight of the enantiomer of the enantiomer, e.g., greater than about 50% by weight of the compound, at least about 80% by weight. In some embodiments, the enrichment is greater than about 80% by weight, providing a "substantially enantiomerically enriched", "substantially enantiomerically pure" or "substantially non racial" Means that the weight of the enantiomer has at least 85% of the composition, such as at least about 90% by weight of the formulation, and further, for example, at least about 95% by weight, relative to one of the other enantiomers. In certain embodiments, the compounds provided herein may be present in an amount of from about 90% by weight of at least one enantiomer. In other embodiments, the compound may be present in an amount of at least about 95%, about 98%, or about 100% by weight of an enantiomer. In some embodiments, the compounds are (S)- and (R)-racemic mixtures. In other embodiments, there is provided a process wherein the individual compound(S) of the mixture is predominantly a mixture of compounds or (R)- is a mixture of predominantly present compounds. For example, the compound mixture has greater than about 55%, about 60%, about 65%, about 70%, about 75%, about 80%, about 85%, about 90%, about 95%, about 96%, about 97%, about 98%, about 99%, about 99.5%, or more. In other embodiments, the mixture of compounds has a(S)-enantiomeric excess of greater than about 55% to about 99.5%, greater than about 60% to about 99.5%, greater than about 65% to about 99.5%, greater than about 70% To about 99.5%, greater than about 75% to about 99.5%, greater than about 80% to about 99.5%, greater than about 85% to about 99.5% Greater than about 96% to about 99.5%, greater than about 97% to about 99.5%, greater than about 98% to greater than about 99.5%, greater than about 99% to about 99.5%, or greater. In other embodiments, the compound mixture (R)-enomer purity has greater than about 55%, about 60%, about 65%, about 70%, about 75%, about 80%, about 85%, about 90% About 95%, about 96%, about 97%, about 98%, about 99%, about 99.5% or more. In other embodiments, the mixture of compounds has an (R)-enantiomeric excess of greater than about 55% to about 99.5%, greater than about 60% to about 99.5%, greater than about 65% to about 99.5%, greater than about 70% To about 99.5%, greater than about 75% to about 99.5%, greater than about 95% to about 99.5%, greater than about 85% to about 99.5% Greater than about 96% to about 99.5%, greater than about 97% to about 99.5%, greater than about 98% to greater than about 99.5%, greater than about 99% to about 99.5% or more.

In other embodiments, the compound mixture comprises, in addition to their stereochemical orientation, i.e., (S)- or (R)- the same chemical entity. For example, if there is a —CH(R)— unit in the compound, and R is not hydrogen, then —CH(R)— is the same chemical entity as the(S)- or (R)-stereochemistry orientation. In some embodiments, the (S)-isomer in the mixture of the same chemical entities is present in an(S)-enantiomeric excess of greater than about 55% to about 99.5%, greater than about 60% to about 99.5%, greater than about 65% to about 99.5%, greater than about 90% to about 99.5%, greater than about 90% to about 99.5%, greater than about 90% to about 99.5% % To about 99.5%, greater than about 95% to about 99.5%, greater than about 96% to about 99.5%, greater than about 97% to about 99.5%, greater than about 98% to greater than about 99.5%, greater than about 99% to about 99.5% or more.

In another embodiment, the (R)-isomer is present in the same chemical entity (except for its stereochemical orientation) relative to the (S)-isomer, at about 55%, about 60%, about 65 About 90%, about 95%, about 85%, about 90%, about 95%, about 96%, about 97%, about 98%, about 99%, about 99.5% or greater. In some embodiments, the (R)-enantiomeric excess in the mixture of the same chemical entity (except its stereochemically oriented) of greater than about 55% to about 99.5%, greater than about 60% to about 99.5%, greater than about 75% to about 99.5%, greater than about 75% to about 99.5%, greater than about 75% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than 99% to about 99.5%, or more.

Enantiomers can be isolated from racemic mixtures by any method known to those skilled in the art, including chiral high performance liquid chromatography (HPLC), chiral salt formation and crystallization, or non-synthetic synthesis. See, for example, Wilen et al., Tetrahedron 33:2725 (1977).

The optical isomers can also be obtained by cleaving the racemic mixture in a conventional manner with an optically active acid or base, for example, by forming a diastereomeric salt. Examples of suitable acids include, but are not limited to, tartaric acid, diacetyl, dibenzoyl, dimethoyltartaric acid and camphorsulfonic acid. Separation of isomers from the mixture of optically active bases of these salts can be achieved by diastereomeric crystallization. Alternatively, the reaction of the open compound with the optically pure acid or optically pure isocyanate of the activated form involves the synthesis of covalent diastereomeric molecules. The synthetic enantiomers can be isolated by conventional methods such as chromatography, distillation, crystallization or sublimation, followed by hydrolysis to provide enantiomerically enriched compounds. The optically active compound can also be obtained by using an active material. In some embodiments, these isomers may be in the form of free acids, free bases, esters or salts.

In certain embodiments, the pharmaceutically acceptable form is a tautomer. As used herein, the term "tautomer" is a type of isomer that includes at least one form of migration and alteration of two or more interconverted compounds derived from hydrogen atoms and covalent bonds (e.g. a single bond to a double bond, a triple bond to a single bond, or vice versa). "Tautomerism" includes proton or proton migration tautomerism, which is considered a subset of acid-base chemistry. "Proton transfer tautomerism" involves proton migration accompanied by a bond change. The exact proportion of tautomers depends on several factors, including temperature, solvent and pH. Among them, tautomerism is possible (for example, in solution), and the chemical equilibrium of the tautomer can be reached. Tautomerism (i.e., the reaction to provide a tautomer pair) can be catalyzed by an acid or base, or presence or absence of an external agent can occur. Such as tautomeric additions include, but are not limited to, ketones to enol; amides to imides; enamines to imines; and one form of enamines to different enamines. Specific examples of ketone to enol tautomer are pentane-2,4-dione and 4-hydroxypent-3-en-2-one tautomers. Another example of tautomerism is phenol and ketone tautomerism. Specific examples of phenol and ketone tautomers are pyridine 4-phenols and pyridine-4-(1H)-one tautomers.

Unless otherwise indicated, it is meant that the structures described herein include compounds that exist only in one or more isotopically enriched atoms. For example, the compound has a structure in which one hydrogen is replaced by deuterium or tritium, or the carbon 13 or carbon 14 within the disclosed range is enriched.

The present disclosure also includes those "isotopically labeled derivatives" which are pharmaceutically acceptable forms of those compounds recited herein, except that one or more atoms are of a different atomic mass generally found in nature. Examples of isotopes that can be incorporated into the disclosed compounds include isotopes of hydrogen, carbon, nitrogen, oxygen, phosphorus, fluorine and chlorine, such as $^2H$, $^3H$, $^{33}C$, $^{14}C$, $^{15}N$, $^{18}O$, $^{17}O$, $^{18}F$, and $^{36}Cl$. Certain isotopically labeled disclosed compounds (e.g., those labeled $^3H$ and $^{14}C$) are useful for the determination of compounds and/or substrate tissue distribution. Tritium (i.e., $^3H$) and carbon 14 (i.e., $^{14}C$) isotopes can be readily prepared and tested. In addition, substitutions with heavier isotopes such as deuterium (i.e., $^2H$ or D) may provide certain therapeutic advantages resulting from greater metabolic stability (e.g., increasing the half-life or reduced dose requirements in vivo). Isotope-labeled disclosed compounds can generally be prepared by replacing an isotopically labeled reagent with a non-isotope-labeled reagent. In some embodiments, provided herein may also contain one or more non-natural atomic isotopes to form such compounds. All isotopic variants of the disclosed compounds are used herein, whether radioactive or not, within the scope of this disclosure. In some embodiments, the radiolabeled compound may be used to study the metabolic and tissue distribution of the compound to alter the metabolic pathway, or rate or other biological function.

The term "CDCl$_3$" refers to deuterated chloroform.

The term "DMSO-d$_6$" refers to deuterated dimethylsulfoxide

The term "LC-MS: (ESI)" refers to electrospray ionization liquid chromatography mass spectrometry The term "alteration" as used herein is defined as a change in the relative physiological state. Exemplary changes include mutations, deletions, fusion with other proteins, overexpression or low expression.

The compounds of the present invention:
In one aspect, the present invention provides compounds of formula (I)

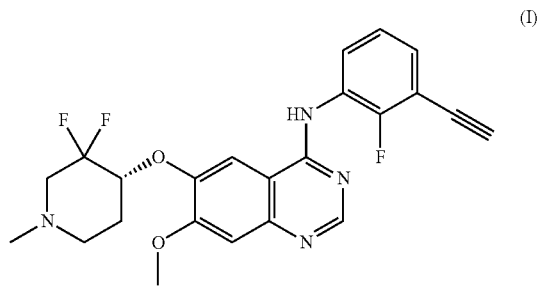 [SMILES: C#Cc1cccc(Nc2ncnc3cc(OC)c(O[C@@H]4CCN(C)CC4(F)F)cc23)c1F]

or a salt thereof; or a prodrug thereof of, or prodrug salt thereof, or a hydrate, solvate or polymorph thereof.

The synthesis of the novel quinazoline derivative (I) with the chirality of R in the present invention can be easily achieved by ordinary synthetic chemists. For example, related methods and intermediates disclosed herein. Every patent, patent application and publication mentioned in this article, regardless of whether it is in a traditional magazine or only available through the Internet, is incorporated herein in its entirety for reference.

Other ways of synthesizing the compound (I) described herein can be easily modified from the references cited herein. Variations of these programs and their optimization are within the abilities of ordinary technicians.

The present invention also provides a composition comprising an effective amount of the compound described herein, or if applicable, a pharmaceutically acceptable salt, solvate, hydrate, polymorph or prodrug of the compound; and acceptable a. Preferably, the composition of the present invention is formulated for pharmaceutical use ("pharmaceutical composition"), wherein the carrier is a pharmaceutically acceptable carrier. In consideration of compatibility with the other ingredients of the formulation, and in the case of a pharmaceutically acceptable carrier, the carrier must be "acceptable" and not harm its recipient in the amount typically used in medicine.

"Pharmaceutically acceptable carrier"; or "pharmaceutically acceptable excipient" includes any and all solvents, dispersion media, coatings, antibacterial and antifungal agents, isotonic and absorption delay agents, and the like. Pharmaceutically acceptable carriers or excipients do not disrupt the pharmacological activity of the disclosed compounds and are non-toxic when administered at a dosage of the amount of the compound sufficient to deliver. The use of such media and reagents for pharmaceutically active substances is well known in the art. Unless any conventional medium or reagent is incompatible with the active ingredient, the use of the therapeutic composition as disclosed herein is contemplated. Examples and excipients of pharmaceutically acceptable carriers include, but are not limited to, sugars such as lactose, sucrose and glucose; starches such as potato starch and corn starch; cellulose and derivatives thereof, such as carboxymethylcellulose sodium, cellulose acetate and ethyl cellulose; gelatin; tragacanth powder; talc; malt; cocoa butter and suppository waxes; oils such as peanut oil, safflower oil, cottonseed oil, olive oil, sesame oil, corn oil and soybean oil: diols such as polyethylene glycol and propylene glycol; esters such as ethyl oleate and ethyl laurate; agar; buffers such as magnesium hydroxide and aluminum hydroxide: alginic acid; aldehyde; phosphate; phosphate buffer: non-toxic compatible lubricants, for example, sodium lauryl sulfate and magnesium stearate: colorants: coating agents; release agents; sweeteners, flavoring agents and fragrances: (SEDDS) such as vitamin E polyethylene glycol 1000 succinate; surfactants for pharmaceutical dosage forms, for example, Tweens or other similar polymer delivery matrix; serum protein, for example, human serum albumin; glycine; sorbic acid; potassium sorbate; partial glyceride mixture of saturated vegetable fatty acids; water, salt or electrolytes such as protamine sulfate, potassium hydrogen phosphate, disodium hydrogen phosphate, sodium chloride And zinc salts; colloidal silica; magnesium trisilicate; polyvinylpyrrolidone; cellulose based materials; polyacrylates; waxes; and polyethylene-polyoxypropylene-block polymers. Cyclodextrins, for example, alpha, beta and gamma-cyclodextrins, or chemically modified derivatives, for example, hydroxyalkyl cyclodextrins including 2- and 3-hydroxypropyl cyclodextrins or other solubilized derivatives to improve the delivery of compounds.

The pharmaceutical compositions of the present invention may be administered in solid or liquid form, including oral administration, for example, irrigation (aqueous or non-aqueous solutions or suspensions), tablets (e.g., those for oral subcutaneous and systemic absorption), hard or soft capsules, pills, syrups, powders, granules, pastes applied to the tongue, duodenal route; parenteral administration, including intravenous, intraarterial, subcutaneous, intramuscular, for example, as a cream, ointment, gelling agent, aqueous or oily solution or suspension, for example, as a cream, ointment, gelling agent, or vaginal suppositories, creams or scaffolds; sublingual; administered locally via catheters or stents; intrathecally, or nasally. (For example, as a fine powder) or by inhalation (e.g., as a fine powder or a liquid aerosol).

Examples of suitable aqueous and nonaqueous carriers in pharmaceutical compositions include water, ethanol, polyols (e.g., glycerol, propylene glycol, polyethylene glycol, etc.), and suitable mixtures thereof, vegetable oils such as olive oil, and organic esters, such as ethyl oleate, are injected. By using a coating material, for example, lecithin, by maintaining the desired particle size of the dispersion, and by using the surfactant to maintain proper fluidity. These compositions may also contain adjuvants such as preservatives, wetting agents, emulsifiers, dispersants, lubricants, and/or antioxidants. The action of the compounds described herein to prevent microbes can be ensured by the inclusion of different antimicrobial and antifungal agents, for example, p-hydroxybenzoates, chlorobutanol, phenol sorbic acid and the like. It may also be in compositions comprising isotonic agents such as sugars, sodium chloride and the like. In addition, prolonged absorption of the injectable drug form may be achieved by comprising a delayed absorbent, such as aluminum monostearate and gelatin.

Methods of making such formulations or compositions include the compounds described herein and/or the steps associated with a chemotherapeutic vehicle and optionally one or more accessory ingredients. In general, the formulation is formed by uniformly and structuring the compound disclosed herein with a liquid carrier, or a finely divided solid carrier or both, and then, if necessary, the product is shaped. The preparation of such pharmaceutical compositions is well known in the art. Unless any conventional excipient medium is incompatible with the compounds provided herein, for example by interacting with any other component of a pharmaceutically acceptable composition to produce any undesirable biological effects or deleterious effects, excipients are also intended to be within the scope of the present disclosure.

In some embodiments, the concentration of one or more of the disclosed compounds may be less than about 100%, about 90%, about 80%, about 70%, about 60%, about 50%, about 40%, about 14%, about 13%, about 12%, about 11%, about 10%, about 10%, about 5%, about 4%, about 3%, about 2%, about 1%, about 0.5%, about 0.4%, about 0.3%, about 0.2% About 0.09%, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, about 0.0009%, about 0.0008%, about 0.0007%, about 0.0006%, about 0.0005%, about 0.0004% 0.0003% 0.0002% or about 0.0001% weight/weight ratio, weight/volume ratio, or volume/volume ratio.

In some embodiments, the concentration of one or more of the compounds disclosed herein may be greater than about 90%, about 80%, about 70%, about 60%, about 50%, about 40%, about 30%, about 20%, about 18.5%, about 18.25%, about 17.5%, about 17.25%, about 17%, about 16.5%, about 16.25%, about 16, about 15.5%, about 15.25%, about 15%, about 14.5%, about 14.25%, about 14%, about 13.5%, about 13.25%, about 13%, about 12.5%, about 12.25%, about 12%, about 11.5%, about 11.25%, about 11%, about 10.75%, about 10.5%, about 10%, about 9.75%, about 9.5%, about 9.25%, about 9%, about 8.75%, about 8.5%, about 8.25%, about 8%, about 7.75%, about 7.5%, about 7.25%, about 7%, about 6.75%, about 6.5%, about 6.25%, about 6%, about 5.75%, about 5.5%, about 5.25%, about 5%, About 4.75%, about 4.5%, about 4.25%, about 4%, about 3.75%, about 3.5%, about 3%, about 2.75%, about 2.50%, about 2.25%, about 2%, about 1.75%, about 1.50%, about 1.25%, about 1%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, about 0.0009%, about 0.0008%, about 0.0007%, about 0.0006%, about 0.0005%, about 0.0004%, about 0.0003%, about 0.0002%, or about 0.0001% weight/weight ratio, weight/volume ratio, or volume/volume ratio. In some embodiments, the concentrations of one or more compounds disclosed herein may range from about 0.0001% to about 50%, from about 0.001% to about 40%, from about 0.01% to about 30%, from about 0.02% to about 20%, about 0.09% to about 24%, about 0.08% to about 23%, about 0.07% to about 22%, about 0.06% to about 24%, about 0.2% to about 20%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12%, about 1% to about 10% weight/weight ratio, weight/volume ratio or volume/volume ratio. In some embodiments, the concentration of one or more of the compounds disclosed herein may range from about 0.001% to about 10%, from about 0.01% to about 5%, from about 0.02% to about 4.5%, from about 0.03% To about 4%, from about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% weight/ weight ratio, weight/volume ratio or volume/volume ratio.

In some embodiments, the amount of one or more compounds disclosed herein may be equal to or less than about 10 g, about 9.5 grams, about 9.0 grams, about 8.5 grams, about 8.0 grams, about 7.5 grams, about 7.0 grams, about 6.5 grams, about 6 grams, about 5.5 grams, about 5 grams, about 4.5 grams, about 4 grams, about 3.5 grams, about 3 grams, about 2.5 grams, about 2.0 grams, about 1.5 grams, about 1.0 grams, about 0.95, about 0.9 grams, about 0.85 grams, about 0.8 g, about 0.75 g, about 0.7 g, about 0.65 g, about 0.6 g, about 0.55 g, about 0.5 g, about 0.45 g, about 0.4 g, about 0.35 g, about 0.3 g, about 0.25 g, about 0.2 g, about 0.15 g, about 0.1 g. about 0.09 g, about 0.08 g, about 0.07 g, about 0.06 g, about 0.05 g, about 0.04 g, about 0.03 grams, about 0.02 grams, about 0.01 grams, about 0.009 grams, about 0.008 grams, about 0.007 grams, about 0.006 grams, about 0.005 grams, about 0.004 grams, about 0.003 grams, about 0.002 grams, about 0.001 grams, about 0.0009 grams, 0.0008 grams, about 0.0007 grams, about 0.0006 grams, about 0.0005 grams, about 0.0004 grams, about 0.0003 grams, about 0.0002 grams, or about 0.0001 grams. In some embodiments, the amount of one or more of the compounds disclosed herein may be in excess of about 0.0001 g, about 0.0002 g, 0.0003 g, about 0.0004 g, about 0.0005 g, about 0.0006 g, about 0.0007 g, about 0.0008 g, about 0.0009 grams, about 0.001 grams, 0.0015 grams, about 0.002 grams, about 0.0025 grams, about 0.003 grams, about 0.0035 grams, about 0.004 g, about 0.0045 g, about 0.005 g, about 0.0055 g, about 0.006 g. about 0.0065 g, about 0.007 g, about 0.0075 g, about 0.008 g, about 0.0085 g, about 0.009 g, about 0.0095 g, about 0.01 grams, about 0.015 grams, about 0.02 grams, about 0.025 grams, about 0.03 grams, about 0.035 grans, about 0.04 grams, about 0.045 grams, about 0.05 grams, about 0.055 grams, about 0.06 grams, about 0.065 grams, about 0.07 grams, about 0.075 grams, about 0.08 grams, about 0.085 grams, about 0.09 grams, about 0.095 grams, about 0.1 grams, about 0.15 grams, about 0.2 grams, about 0.25 grams, about 0.3 grams, about 0.35 grams, about 0.4 grams, about 0.45 grams, about 0.5 grams, about 0.55 grams, about 0.6 grams, about 0.65 grams, about 0.7 grams, about 0.75 grams, about 0.8 grams, about 0.85 grams, about 0.9 grams, about 0.95 grams, about 1 grams, about 1.5 grams, about 2 grams, about 2.5 grams, about 3 grams, about 3.5 grams, about 4 grams, about 4.5 grams, about 5 grams, about 5.5 grams, about 6 grams, about 6.5 grams, about 7 grams, about 7.5 grams, about 8 grams, about 8.5 grams, about 9 grams, about 9.5 grams, or about 10 g.

In some embodiments, the amount of one or more compounds disclosed herein may range from about 0.0001 grams to about 10 grams, from about 0.0005 grams to about 9 grams, from about 0.001 grams to about 0.5 grams, from about 0.001 grams to about 8 grams, from about 0.005 g to about 7 g, from 0.01 g to about 6 g, about 0.05 g to about 5 g, from about 0.1 g to about 4 g, from about 0.5 g to about 4 g, or from about 1 g to about 3 g.

In certain preferred embodiments, a pharmaceutical composition comprising an oral administration of a compound as disclosed herein, and a pharmaceutical excipient suitable for oral administration. In some embodiments, there is provided herein a pharmaceutical composition for oral administration: (1) optionally an effective amount of a disclosed compound; (2) an effective amount of one or more second agents; and (3) One or more pharmaceutically acceptable excipients for oral administration. In some embodiments, the pharmaceutical composition further comprises: (4) an effective amount of a third reagent.

In some embodiments, the pharmaceutical composition may be a liquid pharmaceutical composition suitable for oral administration. Pharmaceutical compositions suitable for oral administration may be used as discrete dosage forms, such as capsules, cachets, or tablets, or liquids, solutions, aerosol sprays or suspensions of a predetermined amount of active ingredient containing powder or granules, water or non-aqueous liquid, the liquid emulsion in water or water in the liquid emulsion. Such dosage forms may be prepared by any pharmaceutical method, but all methods include the step of preparing the composition by uniformly and intimately associating the active ingredient with a liquid carrier, a liposome or a finely divided solid carrier, or both. In general, the pharmaceutical composition is formed by mixing the active ingredient homogeneously and intimately with a liquid carrier or a finely divided solid carrier or both, and if necessary, shaping the product into the desired form. For example, the tablet may be one or more components that may be pressed or molded. The tablet may be formed by mixing the free-flowing form such as the active ingredient of the powder or granule, optionally with an excipient such as, but not limited to, a binder, a lubricant, an inert diluent and/or a surfactant or dispersant mix, press in the right machine. The molded tablets may be prepared by molding a mixture of powdered compounds moistened with an inert liquid diluent in a suitable machine. The tablets may optionally be uncoated, coated or nicked and may be formulated to provide a slow or controlled release of the active ingredient therein, thereby providing a sustained effect over a longer period of time, such as, for example, glyceryl monostearate or glyceryl distearate. Formulations for oral use may also be hard gelatin capsules in which the active ingredient may be mixed with an inert solid diluent, for example, calcium carbonate, calcium phosphate or kaolin, or as a soft gelatin capsule in which the active ingredient may be mixed with water or an oil medium, for example, peanut oil, liquid paraffin or olive oil is mixed.

The active ingredient can be tightly combined with a pharmaceutically acceptable carrier by conventional drug mixing techniques. The carrier may take a variety of forms depending on the form of the desired formulation administration. In the preparation of pharmaceutical compositions for oral dosage forms, any of the usual pharmaceutical media can be used as carriers, for example, water, glycols, oils, ethanol, flavoring agents, preservatives, colorants, and oral liquid preparations (e.g., liquids, solutions, and elixirs) or aerosols, or carriers such as starch, sugar, microcrystalline cellulose, diluents, granules, lubricants, binders, and disintegrants can be used in oral solid preparations. The lactose is not used in some embodiments. In some embodiments, the compound may be mixed with lactose, sucrose, starch powder, cellulose ester of alkanoic acid, cellulose alkyl ester, talc, stearic acid, magnesium stearate, magnesium oxide, calcium phosphate, sodium phosphate, calcium sulfate, sodium sulfate, gelatin, gum arabic, sodium alginate, polyvinylpyrrolidone and/or polyvinyl alcohol for further formulation. For example, the preparation of solid oral preparations, suitable carriers also include powders, capsules and tablets. In some embodiments, the tablet may be coated by standard aqueous or non-aqueous techniques.

Suitable for use in pharmaceutical compositions and dosage forms, including, but not limited to, corn starch, potato starch, or other starches, gelatin, natural binders and synthetic gums such as gum arabic, sodium alginate, alginic acid, other alginic acid salts, powdered tragacanth, guar gum, cellulose and derivatives thereof (e.g., ethylcellulose, cellulose acetate, carboxymethylcellulose calcium, sodium carboxymethyl cellulose), polyvinylpyrrolidone, cellulose, pregelatinized starch, hydroxypropylmethyl cellulose, microcrystalline cellulose, and mixtures thereof.

Examples of suitable fillers for use in pharmaceutical compositions and dosage forms include, but are not limited to, talc, calcium carbonate (e.g., granules or powders), microcrystalline cellulose, powdered cellulose, glucose binders, kaolin, mannitol, silicic acid, sorbitol, starch, pregelatinized starch, and mixtures thereof.

The disintegrant may be used in a pharmaceutical composition as provided herein to provide a tablet that disintegrates when exposed to a water environment. Too much disintegrant can cause the tablet to disintegrate in the bottle. Too little may not be sufficient to disintegrate, and thus can change the release rate and extent of the active ingredient of the dosage form. Thus, the disintegrant should be sufficient, neither too little nor too much to detrimentally release the active ingredient. The amount of disintegrant will depend on the formulation and mode of administration, and may be readily implemented by one of ordinary skill in the art. About 0.5 to about 15% by weight of a disintegrant, or about 1 to about 5% by weight of a disintegrant, may be used in a pharmaceutical composition. To form disintegrants and dosage forms for pharmaceutical compositions including, but not limited to, agar, alginic acid, calcium carbonate, microcrystalline cellulose, croscarmellose, crospovidone, sodium acetate, potato or tapioca starch, other starches, preformed starch, clay, other algae, other cellulose, gums or mixtures thereof.

Lubricants may be used to form pharmaceutical compositions including, but not limited to, calcium stearate, magnesium stearate, mineral oil, light mineral oil, glycerol, sorbitol, mannitol, polyethylene glycol, other diols, stearic acid, sodium lauryl sulfate, talc, hydrogenated vegetable oils (e.g., peanut oil, cottonseed oil, sunflower oil, sesame oil, olive oil, corn oil and soybean oil), zinc stearate, ethyl oleate, Ethyl laurate, agar or mixtures thereof. Lubricants also include, for example, silica gel, coagulated aerosols, or mixtures thereof. The lubricant may optionally be added in an amount of less than about 1% by weight of the pharmaceutical composition.

When aqueous suspensions and/or elixirs are used for oral administration, the active ingredient may be combined with various sweetening or flavoring agents, coloring agents or dyes, for example, emulsifiers and/or suspending agents, diluents, for example, water, ethanol, propylene glycol, glycerol, and combinations thereof.

Surfactants that may be used to form pharmaceutical compositions and dosage forms include, but are not limited to, hydrophilic surfactants, lipophilic surfactants, and mixtures thereof. Suitable hydrophilic surfactants may generally have an HLB value of at least about 10, and suitable lipophilic surfactants may generally have an HLB value of less than about 10. The empirical parameter used to characterize the relative hydrophilicity and hydrophobicity is the hydrophilic lipophilic balance value HLB ("HLB" value). The lower HLB value of the surfactant is more lipophilic or hydrophobic and has a greater solubility in the oil while the active agent with a higher HLB value is more hydrophilic and has a greater aqueous solution of the solubility. Hydrophilic surfactants are generally considered to be those having HLB values greater than about 10, however, anions, cations or zwitterionic compounds, HLB scales are generally not applicable. Similarly, lipophilic (i.e., hydrophobic) surfactants are those having an HLB value equal to or less than about 10. However, the HLB value of the surfactant is only a rough guide for general use in industrial, pharmaceutical and cosmetic emulsions.

The hydrophilic surfactant may be ionic or nonionic. Suitable ionic surfactants include, but are not limited to, alkylammonium salts: fusidic acid salts; fatty acid derivatives of amino acids, oligopeptides and polypeptides; derivatives of amino acids, oligopeptides and glycerol esters of polypeptides; lecithin and Phospholipid and its derivatives: carnitine fatty acid ester salts; alkyl sulphates; fatty acid salts; docetyl sodium; acyl lactic acid salts; mono- and diacetylated mono- and diglycerides of tartaric acid esters; succinylated mono- and diglycerides; citrate esters of mono- and di-glycerides; and mixtures thereof. Ionic surfactants include, but are not limited to, for example, lecithin, lysolecithin, phospholipids, lysophospholipids and derivatives thereof; carnitine fatty acid ester salts; alkyl sulfates; fatty acid salts; acyl lactylates; diacylated tartaric acid esters of mono- and mono- and di- and diglycerides; succinylated mono- and diglycerides; citrate esters of mono- and di-glycerides; and mixtures thereof. Hydrophilic nonionic surfactants include, but are not limited to, alkyl glycosides; alkyl maltose; alkyl thiosides; lauroyl polyglycol glycerides; polyoxyalkylene alkyl ethers such as polyethylene glycol polyoxyalkylene alkyl phenols, for example, polyethylene glycol alkylphenols; polyoxyalkylene alkylphenol fatty acid esters such as polyethylene glycol fatty acid monoester and polyethylene glycol fatty acid diester; diol glycerol fatty acid esters; polyglycerol fatty acid esters; polyoxyalkylene sorbitan fatty acid esters, for example, polyethylene glycol sorbitol fatty acid esters; and glycerol esters, vegetable oils, hydrogenated vegetable oils, fatty acids and sterols polyoxyethylene sterols, derivatives thereof, and the like: polyoxyethylenated vitamins and derivatives thereof; polyoxyethylene-polyoxypropylene block copolymers; and mixtures thereof; hydrophilic transesterification products of polyethylene glycol sorbitan fatty acid esters and polyols of at least one triglyceride, vegetable oil and hydrogenated vegetable oil. The polyol may be glycerol, ethylene glycol, polyethylene glycol, sorbitol, propylene glycol, pentaerythritol or carbohydrates. Other hydrophilic nonionic surfactants include, but are not limited to, PEG-10 lauric acid, PEG-12 lauric acid, PEG-20 lauric acid, PEG-32 lauric acid, PEG-32 dilaurate, PEG-12 oleate, PEG-15 oleate, PEG-20 oleate, PEG-20 dioleate, PEG-32 oleate, PEG-200 oleate, PEG-40 oleate, PEG-15 stearate, PEG-32 diester lactone, PEG-40 stearate, PEG-100 stearate, PEG-20 dilaurate, PEG-25 glycerol trioleate, PEG-32 dioleate, PEG-20 glyceryl laurel Lactone, PEG-30 glyceryl laurate, PEG-20 glyceate, PEG-20 glyceryl oleate, PEG-30 glycerol, PEG-30 glyce, PEG-40 castor oil, PEG-40 castor oil, PEG-40 castor oil, PEG-40 castor oil, PEG-40 castor oil, PEG-40 castor oil, PEG-40 castor oil, PEG-40 castor oil, PEG-40 castor oil, PEG-Hydrogenated castor oil, PEG-60 corn oil, PEG-6 glyceryl/capric acid glyceride, PEG-8 caprate/capillate glyceride, polyglyce 1 to 10 laureate, PEG-30 cholesterol, PEG-25 plant sterol, PEG-30 soybean sterol, PEG-20 trioleate, PEG-40 sorbitol oleate, PEG-80 sorbitan laurate, polysorbate 20, polysorbate 80, POE-9 dodecyl ether, POE-23 lauryl ether, POE-10 oleyl ether, POE-20 oleyl ether, POE-20 stearin, PEG-100 tocopherol succinate, PEG-24 cholesterol, Tween 40, Tween 60, sucrose monostearate, sucrose monolaurate, sucrose monopalmitate, PEG 10-100 nonylphenol series, PEG 15-100 octylphenol series and poloxamer. Suitable lipophilic surfactants include, but are not limited to, for example, fatty alcohols; glycerol fatty acid esters; acetylated glycerol fatty acid esters; lower alcohol fatty acid esters; propylene glycol fatty acid esters; sorbitol fatty acid esters; diol sorbitan fatty acid esters; sterols and sterol derivatives; polyoxyethylenated sterols and sterol derivatives; polyethylene glycol alkyl ethers; sugar esters; sugar ethers; lactic acid derivatives of mono- and diglycerides.

The pharmaceutical composition may include a solubilizing agent to ensure good solubilization and/or dissolution of the compound and to minimize the precipitation of the compound. This may be particularly useful for non-oral use, for example, pharmaceutical compositions for pharmaceutical compositions for injection. The solubilizing agent may also be added to increase the solubility of the hydrophilic drug and/or other components, such as the surfactant, or the maintenance of the pharmaceutical composition as a stable or homogeneous solution or dispersion. Examples of suitable solubilizing agents include, but are not limited to, for example, alcohols and polyols such as ethanol, isopropanol, butanol, benzyl alcohol, ethylene glycol, propylene glycol, butylene glycol and isomers thereof, glycerol, pentaerythritol Sorbitol, mannitol, dimethyl isosorbide, polyethylene glycol, polypropylene glycol, polyvinyl alcohol, and other cellulose derivatives, cyclodextrins and cyclodextrin derivatives; ethers of polyethylene glycol, having a molecular weight of about 200 to about 6000, such as tetrahydrofurfuryl alcohol PEG ether (tetrahydrofuran polyglycol ether) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidine, N-alkyl caprolactam, dimethylacetamide and polyvinylpyrrolidone; esters such as ethyl propionate, ester, acetyl triethyl citrate, triethyl citrate, triethyl citrate, ethyl oleate, ethyl octanoate, ethyl butyrate, glycerol triacetate, propylene glycol monoacetate, propylene glycol diacetate, ε-caprolactone and their isomers, delta-valine esters and their isomers, butyrolactones and their isomers; and other known solubilizing agents such as dimethylacetamide, dimethylisosorbide, N-methylpyrrolidone, diethylene glycol monoethyl ether and water. Mixtures of solubilizers may also be used.

The amount of the given solubilizing agent may be limited to a biologically acceptable amount, which can be readily determined by one of skill in the art. The solubilizing agent may be in a weight ratio of about 10%, about 25%, about 50%, about 100%, or at most about 200% by weight, based on the total weight of the drug, and other excipients. A small amount of solubilizing agent may also be used, if desired, such as about 5%, 2%, 1% or less. Typically, the solubilizing agent may be present in about 1% to about 100%, typically from about 5% to about 25% by weight.

The pharmaceutical compositions described may also include one or more pharmaceutically acceptable additives and excipients, flavoring agents, coloring agents, suspending agents, binders, fillers, plasticizers, lubricants, and mixtures thereof. Preservatives may include, but are not limited to, for example, antioxidants, chelating agents, antimicrobial preservatives, antifungal preservatives, alcohol preservatives, acid preservatives and other preservatives. Antioxidants include, but are not limited to, alpha-tocopherol, ascorbic acid, butylated hydroxyanisole, butylhydroxytoluene, monothioglycerol, potassium pyrosulfite, propionic acid, propyl gallate, sodium ascorbate, sodium bisulfate, and sodium sulfite. Chelating agents include, but are not limited to, for example, ethylenediaminetetraacetic acid (EDTA), citrate monohydrate, disodium ethylenediamine tetraacetate, dipotassium ethylenediamine tetraacetate, edetic acid, fumaric acid, malic acid, phosphoric acid, sodium edetate, tartaric acid, and triethylenediamine tetraethyl citrate. Antimicrobial preservatives include, but are not limited to, for example, benzalkonium chloride, benzethonium chloride, benzyl alcohol, bromonitropylene glycol, cetrimonium bromide, cetylpyridinium chloride, chlorocresol, cresol, Ethanol, glycerol, heptacidine, imidazolidine, phenol, phenoxyethanol, phenylethyl alcohol, phenylmercuric nitrate, and propylene glycol. Antifungal agents include, but are not limited to, for example, butyl p-hydroxybenzoate, methyl p-hydroxybenzoate, ethyl p-hydroxybenzoate, propyl p-hydroxybenzoate, benzoic acid, hydroxybenzoic acid, potassium benzoate, potassium sorbate, sodium benzoate, sodium propionate and sorbic acid. Preservatives include, but are not limited to, for example, ethanol, polyethylene glycol, phenol, phenol compounds, bisphenols, chlorobutanol, hydroxybenzoate, and phenylethanol. Acid preservatives include, but are not limited to, for example, vitamin A, vitamin C, vitamin E, beta-carotene, citric acid, acetic acid, dehydroacetic acid, ascorbic acid, sorbic acid and phytic acid. Other preservatives include, but are not limited to, for example, tocopherol acetate, cetrimonium bromide, butylated hydroxyanisole (BHA), butylhydroxytoluene (BHT), ethylenediamine, sodium lauryl sulfate (SLS), Sodium lauryl ether sulfate (SLES), sodium bisulfate, sodium metabisulfite, potassium sulfite, potassium pyrosulfite, methyl p-hydroxybenzoate. In certain embodiments, the preservative may be an antioxidant. In other embodiments, the preservative may be a chelating agent.

In some embodiments, provided herein are pharmaceutical compositions for parenteral administration: (1) an effective amount of a disclosed compound; optionally (2) an effective amount of one or more second reagent; (3) one or more pharmaceutical excipients suitable for parenteral administration and (4) an effective amount of a third reagent.

Wherein the pharmaceutical composition may be administered in the form of an aqueous or oily suspension, or an emulsion, sesame oil, corn oil, cottonseed oil, or peanut oil, and elixirs, mannitol, dextrose, or sterile aqueous solutions, similar drug carrier. Aqueous saline solution is also commonly used for injection. Ethanol, glycerol, propylene glycol, liquid polyethylene glycol, benzyl alcohol, etc. (and mixtures thereof suitable), cyclodextrin derivatives, sodium chloride, tragacanth, buffers, and vegetable oils may also be used. Proper fluidity can be maintained by using a coating, for example, lecithin, or in the case of a dispersion, by maintaining the desired particle size using a surfactant. The prevention of microbial action can be achieved by various antibacterial and antifungal agents, for example, p-hydroxybenzoic acid esters, chlorobutanol, phenol, sorbic acid, thimerosal and the like. The pharmaceutical compositions may also be injected by suitable carriers, including saline, glucose or water, or solubilized with cyclodextrins, co-solvents (e.g., propylene glycol) or micelles (e.g., Tween 80).

The sterile injectable solution may be prepared by filtration and sterilization by the desired amount of the compound disclosed herein with a suitable solvent for the various other ingredients described above. Typically, the dispersion is prepared by incorporating the various sterilized active ingredients into a sterile carrier containing the basal dispersion medium and the appropriate other components listed above. A sterile injectable solution is prepared with a sterile powder, and some of the methods of preparation are carried out by vacuum drying and freeze drying techniques to produce the active ingredient and any other sterile filtered ingredients described above. The sterile injectable preparation may also be prepared by a solution of a non-toxic parenterally acceptable diluent or solvent, for example, a solution in 1,3-butanediol or a sterile injectable solution. Acceptable carriers and solvents that may be used include, but are not limited to, for example, water, Ringer's solution and isotonic sodium chloride solution. In addition, sterile, non-volatile oils are commonly used as solvents or suspending media, including, but not limited to, for example, synthetic mono- or diglycerides. In addition, fatty acids, for example, oleic acid, can also be used in the preparation of injections. The injectable preparation may be sterilized by, for example, a bacterial retention filter, or by adding a sterilizing agent incorporated into a sterile solid composition which may be dissolved or dispersed in sterile water or other sterile injectable medium. The injectable composition may be present in about 0.1 to about 5% by weight of the compounds disclosed herein.

In some embodiments, provided herein are compounds (or transdermal) containing pharmaceutical preparations containing one or more pharmaceutical excipients, such as those disclosed herein, suitable for topical administration. In some embodiments, there is provided a drug-containing composition for topical administration: (1) an effective amount of a disclosed compound; optionally (2) an effective amount of one or more second agents; (3) one or more pharmaceutical excipients suitable for topical administration and (4) an effective amount of a third agent.

The pharmaceutical compositions provided herein may be formulated in a solid, semi-solid of liquid form suitable for local or topical application such as gelling agents, water-soluble gels, liniments, creams, lotions, suspensions, foams, Powders, ointments, ointments, solutions, oils, pastes, suppositories, sprays, emulsions, saline solutions, dimethylsulfoxide (DMSO) based solutions. In general, a carrier having a higher density can provide a region having a long-term exposure to the active ingredient. In contrast, the solution formulation may provide a more direct contact of the region selected by the active ingredient. For example, the ointment formulation may have paraffin or water miscibility. Alternatively, the active ingredient may be formulated as a cream with the cream base of the oil in water. The aqueous phase of the cream matrix may comprise, for example, at least about 30% by weight of polyols such as propylene glycol, butane-1,3-diol, mannitol, sorbitol, glycerol, polyethylene glycol and mixtures thereof. The pharmaceutical compositions described above may also contain suitable solid or gel phase carriers or excipients that may increase penetration or assist in delivery of the compound through the skin barrier layer of the stratum corneum. Examples, such as, urea (e.g., urea), (e.g., menthol), amines, amides, alkanes, alkanols, water, and the like, such as isopropyl myristate and sodium sulphate, pyrrolidone, glycerol monolaurate, sulfoxide, calcium carbonate, calcium phosphate, various sugars, starches, cellulose derivatives, gelatin and polymers such as polyethylene glycol.

Another exemplary formulation used in the disclosed method uses transdermal administration ("patch"). Such transdermal patches can be used to provide a controlled or discontinuous pharmaceutical composition in a continuous or discontinuous manner. If the active agent is absorbed by the skin, the controlled and scheduled flow of the active agent can be administered to the subject. In the case of microcapsules, the encapsulant may also be used as a film. The use of transdermal patches is well known in the art. See, for example, U.S. Pat. Nos. 5,023,252, 4,992,445 and 5,001,139.

The pharmaceutical compositions of the present invention may be administered in the form of suppositories for rectal administration. These compositions may be prepared by mixing the compounds of the present invention with a suitable non-irritating excipient which is solid at room temperature but is liquid at the rectal temperature and will melt in the rectum to release active ingredient. Such materials include, but are not limited to, for example, polyethylene glycol, beeswax and cocoa butter.

The pharmaceutical compositions of the present invention may be administered by nasal aerosols or inhalants. Such a composition is prepared according to techniques known in the pharmaceutical preparation art and can be prepared as a solution of brine and can be used with benzyl alcohol or other suitable preservatives to increase the bioavailability of absorption enhancers, fluorocarbons, and other solubilizing or dispersing agents known in the art.

Particularly advantageous derivatives and prodrugs are those that increase the bioavailability of the compounds of the present invention when administered to a mammal (e.g., by allowing oral administration of the compound to be more easily absorbed) maternal species that enhance the delivery of compounds to the parent biopsy (e.g., the brain or central nervous system). Preferred prodrugs include derivatives wherein the groups that enhance water-soluble or parenteral transport are attached to the general structure described herein. See, for example, Alexander et al., Journal of Medicinal Chemistry 1988, 31, 318-322; Bundgaard et al., Journal of Medicinal Chemistry 1987, 30, 451-454.

The application of the subject therapeutic agent may be localized to be administered at the target site. Various techniques may be used to provide a host composition at a target site, such as injection, use of a catheter, gel, stent, trocar, propellant, drug release polymer, or other device for providing internal access.

According to another embodiment, the present invention provides an implantable medical device comprising a compound of the invention or a composition comprising a compound of the invention such that the compound is a therapeutically active.

According to another embodiment, the present invention provides a method of injecting an implantable drug delivery device comprising the step of contacting said drug delivery device with a compound or composition of the invention. Implantable drug delivery devices include, but are not limited to, biodegradable polymeric capsules or pills, non-degradable, dispersible polymer capsules and biodegradable polymer flakes.

In another embodiment, the compositions of the present invention further comprise a second therapeutic agent. The second therapeutic agent includes any compound or therapeutic agent which, when administered alone or in combination with any of the compounds of the general formula herein, is known to have or is of a favorable nature. Drugs that may be usefully combined with these compounds include other kinase inhibitors and/or other chemotherapeutic agents for the treatment of diseases and disorders discussed above. Such agents are described in detail in the art. Preferably, the second therapeutic agent is an agent that can be used for the treatment or prophylaxis of a disease or condition selected from cancer.

In another embodiment, the present invention provides an independent dosage form of a compound of the invention and a second therapeutic agent associated with each other. As used herein, the term "associated with each other" means that the individual dosage forms are packaged together or otherwise connected to each other so that the individual dosage forms are expected to be sold or administered together (less than 24 hours Inside, continuously or simultaneously).

In the pharmaceutical compositions of the present invention, the compounds of the present invention are present in an effective amount. As used herein, the term "effective amount" refers to the severity, duration, or development of a disorder that is sufficient to reduce or ameliorate the disorder to be treated when administered with a suitable dosing regimen, to prevent progression of the disorder, the disruption of the treatment disorder, or the enhancement or improvement of the prophylactic or therapeutic effect of another therapy.

The body surface area can be roughly determined according to the height and weight of the patient. The effective amount of the compound of the present invention may range from about 0.001 to 1 mg/kg to about 500 mg/kg, from about 0.01 mg/kg to about 50 mg/kg, from about 0.1 mg/kg to about 2.5 mg/kg. Effective dosages may also vary, as will be appreciated by those skilled in the art, depending on the disease being treated, the severity of the disease, the route of administration, the age, sex and general health of the patient, excipient usage, and other treatments method for common use (e.g., the use of other agents), and the judgment of the treatment physician.

For a pharmaceutical composition comprising a second therapeutic agent, the effective amount of the second therapeutic agent is between about 20% and 100% of the dose normally used in a single treatment regimen using only the agent. Preferably, the effective amount is between about 70% and 100% of the normal single therapeutic dose. The normal single therapeutic doses of these second therapeutic agents are well known in the art.

It is expected that some of the second therapeutic agents mentioned herein will act synergistically with the compounds of the present invention. When present, it will allow the effective dose of the second therapeutic agent and/or the compound of the invention to be less than the dosage required for single therapy. This has the advantage that the secondary side effects of the second therapeutic agent or the compound of the present invention are minimized, improved efficacy, improved ease of administration or use, and/or reduced overall cost of the compound preparation or formulation.

The treatment is as follows:

According to another embodiment, the present invention provides a method of treating a subject suffering from or susceptible to a disease or disorder or a symptom thereof (e.g., those described herein) comprising administering to said subject an effective amount of the inventive compounds or compositions are administered in a step. These diseases are well known in the art and are also disclosed herein.

The treatment involves the treatment of disorders mediated by protein kinases such as EGFR.

In another aspect, the present invention provides a method of treating a disease in a subject comprising administering to a subject a composition comprising any compound of the general formula herein.

In certain embodiments, the disease is mediated by an EGFR kinase.

In another embodiment, the disease is a cancer or a proliferative disease.

In another embodiment, as an inhibitor against the EGFR Exon 2-7 deletion EGFRVIII activating mutant, the compound of formula (I), and the pharmaceutically acceptable salt, is expected to be present in the activity of the EGFRVIII mutant or partially mediated, such as the treatment of cancer or medical conditions. This may use the type of cancer treated with the compound of formula (I), or a pharmaceutically acceptable salt, including, but not limited to, ovarian cancer, cervical cancer, colorectal cancer, breast cancer, pancreatic cancer, glioma, glioblastoma, melanoma, prostate cancer, leukemia, lymphoma, non-Hodgkin's lymphoma, gastric cancer, lung cancer, liver cancer, bone cancer, gastrointestinal stromal tumors (GIST), thyroid cancer, cholangiocarcinoma, uterus Endometrial cancer, renal cell carcinoma, anaplastic large cell lymphoma, acute myeloid leukemia (AML), multiple myeloma, melanoma, mesothelioma, brain cancer, adenocarcinoma, skin cancer or head and neck squamous cell carcinoma.

In another embodiment, as an inhibitor against the EGFR Exon 21 L858R and Exon 19 deletion activating mutant, the compound of formula (I), and the pharmaceutically acceptable salt, is expected to be present in the activity of the EGFR mutant or partially mediated, such as the treatment of cancer or medical conditions. This may use the type of cancer treated with the compound of formula (I), or a pharmaceutically acceptable salt, including, but not limited to, ovarian cancer, cervical cancer, colorectal cancer, breast cancer, pancreatic cancer, glioma, glioblastoma, melanoma, prostate cancer, leukemia, lymphoma, non-Hodgkin's lymphoma, gastric cancer, lung cancer, liver cancer, bone cancer, gastrointestinal stromal tumors (GIST), thyroid cancer, cholangiocarcinoma, uterus Endometrial cancer, renal cell carcinoma, anaplastic large cell lymphoma, acute myeloid leukemia (AML), multiple myeloma, melanoma, mesothelioma, brain cancer, adenocarcinoma, skin cancer or head and neck squamous cell carcinoma.

In another embodiment, the disease is glioma.

In another embodiment, the disease is non-small cell lung cancer (NSCLC) with central nervous system metastases.

In another embodiment, the disease is central nervous disease.

In one embodiment, the method of the invention is used to treat a subject suffering from or susceptible to a disease or condition. These diseases, disorders or their symptoms include, for example, those regulated by protein kinases (e.g., EGFR protein kinases). The disease or disease symptoms may be, for example, cancer or proliferative diseases or disorders. The disease or disease symptoms may be ovarian cancer, cervical cancer, colorectal cancer, breast cancer, pancreatic cancer, glioma, glioblastoma, melanoma, prostate cancer, leukemia, lymphoma (GIST), thyroid cancer, cholangiocarcinoma, endometrial cancer, kidney cancer, anaplastic large cell lymphoma, acute myeloid leukemia (GIST), gastric cancer, lung cancer, liver cancer, AML), multiple myeloma, melanoma, mesothelioma, brain cancer, membranous adenocarcinoma, skin cancer or squamous cell carcinoma of the head and neck. The methods described herein include those subjects in which the subject is identified as requiring treatment that is specifically described. The identification of the subject requires that the treatment be within the judgment of the subject or health care specialist and may be subjective (e.g., opinion) or objective (e.g., measurable by test or diagnostic method).

In another embodiment, the compounds of the general formula (and compositions thereof) herein are useful for the treatment of diseases or disorders that have been treated with other therapeutic agents (e.g., anticancer agents, neurotrophic agents, psychotropic agents, a cardiovascular disease agent, an anti-obesity or diabetes agent) and to form a resistant subject. In one aspect, the methods herein include administering to a subject in which treatment is resistant (or identified as having resistance to treatment with gefitinib, erlotinib) in which the compound of formula (or its composition) of those methods. In other aspects, the subject is therefore responsive to the treatment, so that the disorder is regulated or improved prior to treatment with the compound of the present formula.

In another embodiment, the present invention provides a method of modulating the activity of a protein kinase in a cell (e.g., a protein kinase kinase, a kinase as enumerated herein) comprising contacting the cell with one or more compounds of the general formula herein contact.

The anti-cancer treatment described above can be administered as a monotherapy or with conventional compounds or radiotherapy or chemotherapy or immunotherapy with the compounds of the present invention. Such chemotherapy may be co-administered, simultaneously, sequentially or separately, with the compounds of the present invention and may include, but are not limited to, one or more of the following categories of antineoplastic agents: for example, antiproliferative/antineoplastic agents, alkylation (e.g., cisplatin, oxaliplatin, carboplatin, cyclophosphamide, nitrogen mustard, melphalan, chlorambucil, busulfan, temozolomide and nitrosourea), antimetabolites (e.g., gemcitabine and antifungal acids such as 5-fluorouracil and tegafur, raltitrexed, methotrexate, cytarabine, and hydroxyurea); antitumor antibiotics (e.g., anthracycline drugs such as doxorubicin, bleomycin, adriamycin, daunorubicin, epirubicin, idarubicin, mitomycin C, gentamicin and gliramycin); antimitotic agents (e.g., vinca alkaloids such as vincristine, alkaloids such as paclitaxel and tacrolimus and polokinase inhibitors); and topoisomerase inhibitors (e.g., epipodophyllotoxin etoposide and dipyridine) glycosides, an acridine, topotecan and camptothecin): cell growth inhibitors such as anti-Hormones (e.g., tamoxifen, fulvestrant, toremifene, raloxifene, droloxifene and zifoxifene), antiandrogens (e.g., amylamine, flutamide, nilutamide acetate and cyclopropanone), LHRH antagonists or LHRH agonists (e.g., goserelin, leuprolide and bucorin, progesterone (e.g., megestrol acetate, Aromatase inhibitors (e.g., anastrozole, letrozole, buoxazole, and exemestane) and inhibitors of 5a reductase such as finasteride; anti-invasive agents (e.g., c-Src kinase family inhibition agents such as cetatinib; dasatinib and bosutinib and bosutiphene, and inhibitors of metalloproteinases such as equine, inhibitors of urokinase plasminogen activator receptor or antibody heparinase. Inhibitors of growth factor function: for example, such inhibitors include growth factor antibodies and growth factor receptor antibodies (e.g., anti-erbB2 antibody trastuzumab [Herceptin™], anti-EGFR antibody panitumumab, and anti-ErbB antibody cetuximab (erbatide, C225) and by Stem et al. Critical reviews in oncology/haematology disclosed a growth factor receptor or a growth factor receptor antibodies, 2005, Vol. 54, 11-29. Such inhibitors also include tyrosine kinase inhibitors such as epidermal growth factor family inhibitors (e.g., EGFR family inhibitors such as gefitinib, erlotinib, icotinib, afatinib, dacomitinib and Tagrisso, erbB2 tyrosine kinase inhibitors, such as lapatinib, neratinib); hepatocyte growth factor family Inhibitors; the platelet-derived growth factor family such as imatinib and/or nilotinib; inhibitors of serine/threonine kinases (e.g., RAS/RAF signaling Inhibitors such as feniyltransferase inhibitors such as sorafenib, tipifanib and lonafanib, by MEK and/or AKT kinase cell signaling inhibitors, c-kit inhibitors, abl fusion kinase inhibitors, PI3 kinase inhibitors, PLT3 kinase inhibitors, CSF-1R kinase inhibitors, IGF receptors (insulin-like growth factor) kinase inhibitors; aurora kinase inhibitors and cyclin-dependent kinase inhibitors such as CDK2 and/or CDK4 inhibitors; antiangiogenic agent, such as those that inhibit the effects of vascular endothelial growth factors, antibodies bevacizumab (Avastin™) and, for example, VEGF receptor tyrosine kinase inhibitors such as vandetanib. Vatalanib, sunitinib, axitinib, pazopanib and cediranib, compounds that work through other mechanisms (e.g., tricarboxyaminoquinoline, integrin αV3 functional inhibitors and angiogenesis inhibitors); antisense (nucleic acid) therapy, including, for example, the replacement of abnormal genes such as abnormal p53 or aberrant BRCA1 or BRCA2, as described above, such as ISIS 2503, anti-ras gene antisense (nucleic acid) (e.g., Olaparnib, Niraparib, Rucaparib, Talazoparib), GDEPT (gene-directed prodrug therapy) methods such as enzymes using cytosine deaminase, thymidine kinase or bacterial nitro reductase, and those that increase patient resistant chemotherapeutic or radiotherapy such as multidrug resistance gene therapy immunotherapy, including, for example, increasing the inununogenicity of tumor cells of a patient, e.g., using cytokines such as interleukin 2, 4 or granulocyte-macrophage stimulating factor transfection of the immunogenicity of the T cells to reduce the nonresponsiveness of the method using transfected immune cells such as cytokine transfected dendritic cells, cytokine transfection anti-idiotypic antibody to reduce the function of inununosuppressive cells such as regulatory T cells, medullary inhibitory cells or IDO, TDO, and the use of antibodies derived from tumor-associated antigens such as NY-ES0-1, MAGE-3, WTI or HER2/neu derived protein or peptide or any other agent (e.g., antiemetic agent, antianemia agent, etc.) that is generally used as a base agent or adjuvant in a cancer treatment regimen.

As used herein, the term "co-administered" means that the second therapeutic agent may be administered in combination with a compound of the invention as a single dosage form (e.g., a composition comprising a compound of the invention and a second therapeutic agent as described above) in part or as an independent, multi-dose form. Alternatively, additional reagents may be administered prior to, or in connection with, or after the administration of the compounds of the invention. In such combination therapy, the compounds of the present invention and the second therapeutic agents are administered by conventional methods. The administration of the compositions of the invention comprising the compounds of the invention and the second therapeutic agent to the subject does not exclude the same therapeutic agent, any other second therapeutic agent or any of the compounds of the invention at other times during the course of treatment Independent administration of the subject. Wherein the continuous or separate administration, or delaying administration of the second component, should not lose the advantage of the effect produced from the use of the combination.

The effective amount of the second therapeutic agent is well known to those skilled in the art. However, determining the optimal effective amount of the second therapeutic agent is within the capabilities of those skilled in the art.

In one embodiment of the invention, when the second therapeutic agent is administered to the subject, the effective amount of the compound of the invention is lower than the effective amount of the second therapeutic agent when no second therapeutic agent is administered. In another embodiment, the effective amount of the second therapeutic agent is less than the effective amount of the second therapeutic agent when the compound of the invention is not administered. In this way, undesirable side effects associated with any of the high doses of the agent can be minimized. The potential advantages for those skilled in the art will be apparent (including, but not limited to, for example, improving the dosing regimen and/or reducing the cost of the drug).

In another aspect, the invention provides the use of any of the compounds of the general formula herein, either alone or in combination with one or more of the second therapeutic agents described herein, in the manufacture of a medicament as a single composition or as a separate dosage form, a medicament for the treatment or prevention of a disease, disorder or symptom listed herein in a subject. Another aspect of the invention is the use of a compound of the general formula herein for the treatment or prevention of a disease, disorder or symptom described herein in a subject.

In other aspects, the methods herein include further comprising those methods of monitoring the response of the subject to therapeutic administration. Such monitoring may include periodic sampling of subject tissue, body fluids, cerebrospinal fluid, samples, cells, proteins, chemical markers, genetic material, etc. as a marker or indicator of a therapeutic regimen. In other methods, by assessing the adaptability of the relevant marker or indicator to such treatment, the subject is pre-screened or identified as requiring such treatment.

In one embodiment, the present invention provides a method of monitoring the progression of therapy. The method comprises determining a diagnostic marker (marker) in a subject suffering from or susceptible to disorders or symptoms described herein (e.g., any target or cell type described herein regulated by the compounds herein) or diagnosed (e.g., screening, assay), wherein the subject has been administered a compound of the present invention sufficient to treat the therapeutic amount of the disease or its symptoms. The level of the marker determined in the method may be compared to a well known level in a healthy normal control or other diseased patient to establish a disease condition of the subject. In a preferred embodiment, the second level of the marker in the subject is measured at a time point later than the first level of measurement and the two levels are compared to monitor the efficacy of the progression or therapy of the disease. In certain preferred embodiments, the level of the marker prior to treatment in the subject is measured prior to initiation of treatment according to the present invention; the pre-treatment level of the marker may be the same as the marker in the subject after treatment initiation Level to determine the effectiveness of treatment.

In certain method embodiments, the level of marker or marker activity in the subject is determined at least once. The marker level is compared with another measured value, for example, from the same patient, another patient, or another subject that was previously or subsequently acquired by the subject, to determine whether the therapy according to the present invention has the desired effect, and thus allow the dose level to be adjusted as appropriate. The determination of the level of the marker can be carried out using any suitable sampling/expression assay method known in the art or described herein. Preferably, the tissue or liquid sample is first removed from the subject. Examples of suitable samples include blood, urine, cerebrospinal fluid, tissue, mouth or buccal cells, and hair samples containing roots. Other suitable samples are known to those skilled in the art. The determination of protein levels, ctDNA, cfDNA and/or mRNA levels (e.g., marker levels) in the sample can take advantage of any suitable technique known in the art including, but not limited to, enzyme immunoassays, ELISA, radioactive labeling techniques, western blot/chemiluminescence, real-time PCR, electrochemical signals, and the like.

The present invention also provides a kit for the treatment of diseases, disorders or symptoms of those described herein. Such kits include: 1) a pharmaceutical composition comprising any of the compounds of the general formula herein or salts thereof; or a prodrug thereof, or a salt thereof; or a pharmaceutical composition of a hydrate, solvate or polymorph thereof, in a container; and 2) describes a description of the use of the pharmaceutical composition for the treatment of a method comprising a disease, disorder or symptom described herein. The container may be any container or other sealed or sealable device capable of containing the pharmaceutical composition. Examples include a bottle, a separate or multi-chamber reservoir bottle, wherein each partition or compartment comprises a single dose of the composition: a separated foil package, wherein each partition comprises a single dose of the composition, which dispenses a single dose of said composition. The container may be any conventional shape or form known in the art and is made of a pharmaceutically acceptable material such as paper or cardboard boxes, glass or plastic bottles or cans, resealable bags (e.g., The "refill" of the tablet is used to be placed in a different container), or a single dose of blister pack is used to extrude the package from the treatment schedule. The containers used may depend on the exact dosage form involved, for example, conventional cardboard boxes will generally not be used to contain liquid suspensions. It is possible that more than one container can be used together in a single package to market a single dosage form. For example, the tablet may be contained in a bottle, which is then accommodated in the box. Preferably, the container is a blister pack.

The kit may additionally include information and/or instructions from a physician, pharmacist or subject. These memory aids include numbers printed on each compartment or partition containing the agent, which corresponds to the number of days the program or capsule should be ingested, or printed on each compartment or partition week number of days, or cards containing the same type of information.

In the use of the present invention with EGFRVIII activating mutations, the enantiomeric purity of the quinazoline derivative (I) of the present invention is greater than about 55% to about 99.5%, greater than about 60% to about 99.5%, Greater than about 65% to about 99.5%, greater than about 70% to about 99.5%, greater than about 75% to about 99.5%, greater than about 80% to about 99.5%, greater than about 85% to about 99.5%, greater than about 90% to About 99.5%, greater than about 95% to about 99.5%, greater than about 96% to about 99.5%, greater than about 97% to about 99.5%, greater than about 98% to greater than about 99.5%, greater than about 99% to about 99.5%, Or higher.

The compounds described herein can be evaluated for their biological activity using protocols known in the art, including, for example, those described herein. Some of the compounds herein demonstrated unexpectedly excellent properties (for example, metabolic stability, high selectivity, low efflux rate, high permeability, non-P glycoprotein efflux substrate, etc.), making them excellent as potential therapeutic agents candidates.

All references cited herein, whether electronic, printed, computer-readable, or otherwise, are expressly incorporated herein by reference in their entirety, including, but not limited to, abstracts, articles, journals, publications, textbooks, papers, technical data sheets, internet sites, databases, patents, patent applications, and patent publications.

The present invention will now be described in detail with reference to the following examples. The following examples will aid the person skilled in the art in further understanding the present invention without limiting the invention in any way. It should be noted that many modifications and improvements may be made by those skilled in the art without departing from the spirit of the invention. All of which are within the scope of the present invention.

Example 1. Preparation of Quinazoline Derivative (I)

1.1 Intermediate 5-fluoro-4-methoxy-2-nitrobenzonitrile A6 was Synthesized as Follows

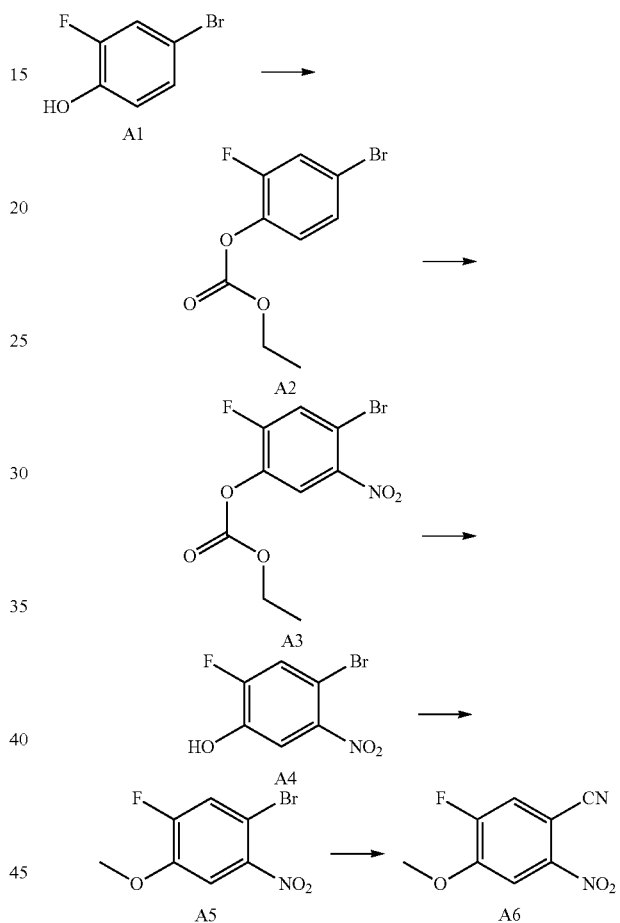

Step 1: To a solution of A1 (2.0 g, 10.5 mmol) and triethylamine (1.3 g, 12.6 mmol) in dichloromethane (10 mL) at 0° C. was added dropwise to a solution of methylene chloride ester (1.4 g, 12.6 mmol). The reaction mixture was stirred at 0° C. for 1 hour and allowed to reach room temperature. The reaction mixture was then washed twice with water. The organic layer was dried over magnesium sulfate and evaporated in vacuo to give product A2 (2.7 g, yield 100%) as a colorless oil.

Step 2: To a solution of A2 (2.7 g, 10.3 mmol) in concentrated sulfuric acid (4.6 mL) was added dropwise to nitric acid (0.73 mL, 15.5 mmol) at 10° C. After 1 hour, the reaction mixture was poured into ice/water and extracted twice with ethyl acetate. The combined organic layers were washed with water, sodium bicarbonate and brine, dried over sodium sulfate and evaporated in vacuo to give a residue which was purified on a silica gel column (n-hexane/ethyl acetate=20/1) to give a yellow oil product A3 (3.0 g, yield 94.6%).

Step 3: A solution of A3 (3.0 g, 9.8 mmol) in methanol (17 mL) was added sodium bicarbonate (1.6 g, 19.6 mmol). The reaction mixture was stirred at 60° C. for 3 hours. Methanol was evaporated under vacuum. Water (15 ml) was added to the residue and the aqueous layer was acidified to pH=5 by the addition of 5 moles of hydrogen chloride. The aqueous layer was extracted twice with ethyl acetate. The combined organic layers were dried over magnesium sulfate and evaporated in vacuo to give the product A4 (2.3 g, yield 100%) as a yellow solid.

Step 4: Potassium carbonate (2.7 g, 19.6 mmol) and methyl iodide (1.22 mL, 19.6 mmol) were added to a solution of A4 (2.31 g, 9.8 mmol) in nitrogen, nitrogen-dimethylformamide (18.5 mL). The reaction mixture was stirred at 60° C. for 3 hours. The resulting mixture was separated between water and ethyl acetate. The organic layer was dried over sodium sulfate and evaporated in vacuo to give product A5 as a yellow solid (2.35 g, 97% yield).

Step 5: After stirring in a solution of A5 (5.17 g, 20.7 mmol) and zinc cyanide (1.46 g, 12.4 mmol) in N, N-dimethylacetamide (104 mL) and the air was vented with nitrogen. Palladium catalyst, Pd$_2$(dba)$_3$ (1.90 g, 2.07 mmol), and ligand, 2-dicyclohexylphosphino-2'-(N, N-dimethylamine)-biphenyl (815 mg, 2.07 mmol) were added and the reaction mixture was stirred at 110° C. for 5 hours. It was then cooled to room temperature, diluted with ethyl acetate and filtered through celite. The organic solution was washed with brine, dried over sodium sulfate, concentrated in vacuo and purified by silica gel column (ethyl acetate/n-hexane=1:50 to 1:10) to give the product as a pale yellow solid A6 (3.47 g, yield 85.7%). $^1$HNMR: (400 MHz, DMSO-d$_6$) δppm: 8.28 (d, J=10.7 Hz, 1H), 8.13 (d, J=7.5 Hz, 1H), 4.08 (s, 1H). LC-MS: (ESI) m/z=197 (M+H)$^+$ 1.2 Preparation of intermediate
3,3-difluoro-1-methylpiperidin-4-ol B8

Synthetic route is as below:

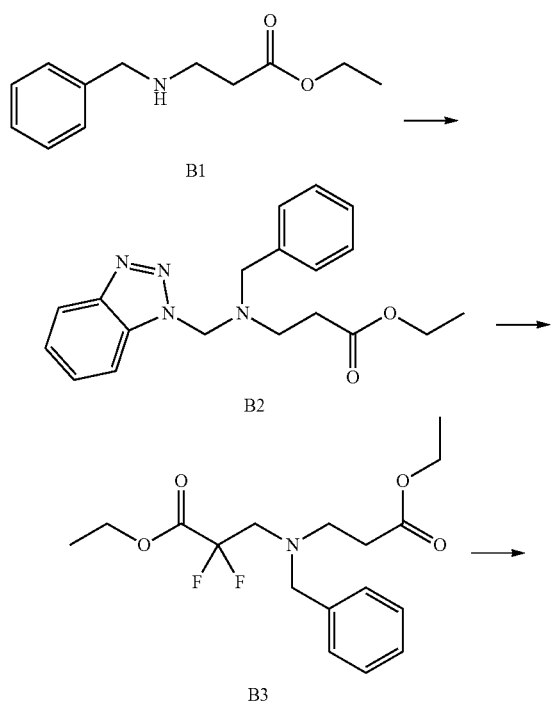

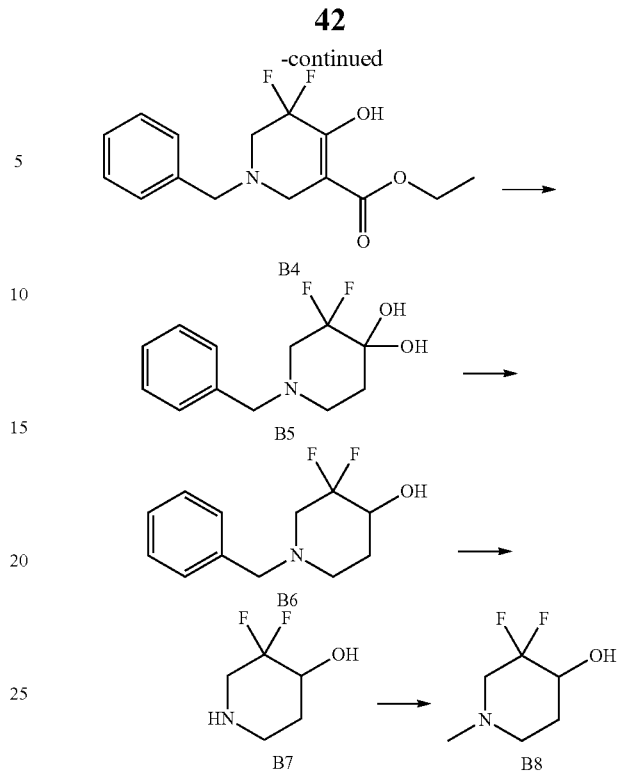

Step 1: To a solution of benzotriazole (47 g, 394.5 mmol) in methanol (300 mL) was added B1 (81.7 g, 394.5 mmol) and 37% formaldehyde (37.9 mL, 512.9 mmol) and the resulting mixture was stirred at room temperature for 16 hours. The mixture was removed in vacuo and the residue was poured into water (500 ml), extracted with ethyl acetate (500 ml×3), dried over sodium sulfate, filtered and concentrated to give product B2 as a yellow oil (132 g, Yield 98.8%).

Step 2: Trimethylsilyl chloride (49 g, 452 mmol) was added to a solution of zinc dust (56 g, 862 mmol) in tetrahydrofuran (500 mL) at room temperature. The resulting suspension was stirred at room temperature for 15 minutes and then ethyl difluorobromoacetate (96 g, 474 mmol) was added dropwise and the mixture was stirred for 15 min. A solution of B2 (146 g, 431 mmol) in tetrahydrofuran (500 mL) was then added at room temperature and stirred overnight. The mixture was poured into a saturated aqueous solution of sodium bicarbonate (2.5 L), extracted with ethyl acetate (500 ml), filtered through celite, separated, the organic phase was dried over sodium sulfate, filtered and concentrated to give the residue. Purification by silica gel column (ethyl acetate/n-hexane=1/50 to 1/20) gave the product B3 (90 g, yield 60.8%) as a yellow oil.

Step 3: To a solution of diisopropylamine (63.0 g, 629 mmol) in tetrahydrofuran (500 mL) was added dropwise n-butyllithium (2.5 M hexane, 231.5 mL, 576 mmol) at −70° C. and the resulting mixture was warmed to −10° C. and reacted for 30 minutes. The system was then cooled to −70° C. and a solution of B3 (90 g, 262 mmol) in tetrahydrofuran (500 L) was added dropwise. The mixture was stirred for 30 minutes and gradually warmed to room temperature and stirred for an additional hour. The mixture was poured into saturated aqueous ammonium chloride (500 ml) and extracted with ethyl acetate (500 L×3). The organic phase was dried over sodium sulfate, filtered and concentrated to give product B4 (90.7 g) as a yellow oil. The crude product is used directly in the next step without purification.

Step 4: B4 (90 g, 302 mmol) was added to a solution of 6N hydrochloric acid (900 ml) and the mixture was heated to reflux for 3 hours. After cooling to room temperature, the mixture was slowly poured into 8N of sodium hydroxide (1 L), extracted with ethyl acetate (1 L) three times, the organic phase was concentrated to 4-5 L, n-hexane (600 ml) was added, stirred for 1 hour and filtered to give the product B5 as a white solid (34 g, 46.5% in two steps).

Step 5: To a solution of B5 (34 g, 139 mmol) in methanol (730 mL) was added sodium borohydride (7.9 g, 209 mmol) in portions at 0-5° C. After stirring at 0-5° C. for an additional 15 minutes, an aqueous solution of sodium bicarbonate (0.1 mole, 54 mL) was added and the mixture was stirred for 5 minutes. The mixture was dried over sodium sulfate, concentrated and purified by silica gel column ethyl acetate/n-hexane=1/20 to 1/10) to give product B6 as a colorless oil (30 g, yield 97.1%).

Step 6: To a solution of B6 (30 g, 134 mmol) in ethanol (600 mL) was added palladium hydroxide/activated charcoal (10%, 3.0 g) and the mixture was stirred under a hydrogen balloon for 4 hours. The mixture was filtered and concentrated to give the product B7 as a white solid (15.8 g, 85.8% yield). $^1$HNMR: (400 MHZ, DMSO-$d_6$) δppm, 5.43 (d, J=5.1 Hz, 1H), 3.71 (m, 1H.), 2.98 (m, 1H), 2.84-2.57 (m, 2H), 2.23 (s, 1H), 1.85-1.64 (m, 1H), 1.60-1.34 (m, 1H). LC-MS: (ESI) m/z=138.0 (M+H)+

Step 7: A solution of 37-40% formaldehyde (584 mg, 7.2 mmol) was added to 88% formic acid solution (941 mg, 18.0 mmol) of B7 (500 mg, 3.6 mmol) at room temperature. The solution was stirred at 78° C. for 30 minutes. The mixture was washed with aqueous sodium hydroxide to adjust the pH to 9 to 10. The mixture was extracted with ethyl acetate (30 mL×3). The organic phase was dried over sodium sulfate and concentrated to give the product B8 as a white solid (340 mg, yield 62.5%). 1H NMR (400 MHZ, DMSO-$d_6$) δppm: 5.48 (d, J=5.4 Hz, 1H), 3.79-3.48 (m, 1H), 2.74 (dd, J=22.1, 12.2 Hz, 1H), 2.46-2.34 (m, 1H), 2.20 (s, 4H), 1.90-1.69 (m, 1H), 1.69-1.47 (m, 1H). LC-MS: (ESI) m/z=152 [M+H]$^+$ 1.3 Synthesis of intermediate tert-butyl (Z)-4-(5-cyano-4-(((dimethylamino) methylene) amino)-2-methoxyphenoxy)-3,3-difluoropiperidine-1-carboxylate A9, the Synthetic Route is as Follows

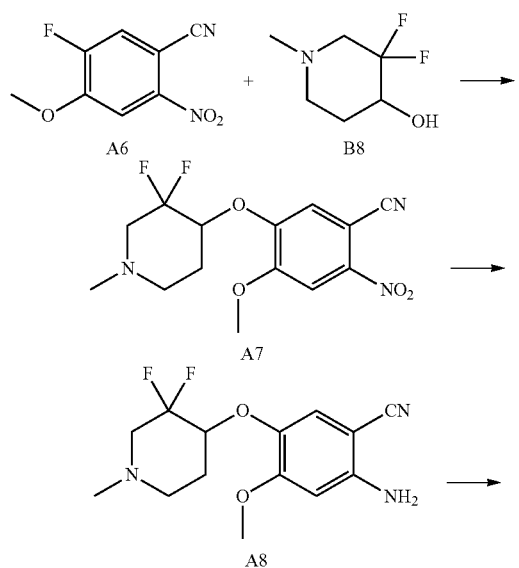

Step 1: Add A6 (10 g, 51 mmol) and B8 (7.71 g, 51 mmol) in N,N-Dimethylacetamide (30 ml) solution to a solution of sodium hydride (4.85 g, 102 mmol) in N,N-dimethylacetamide (10 ml) under nitrogen protection at 50 degrees Celsius. Stir at 0 degrees Celsius for 1 hour. The mixture was poured into a saturated solution of ammonium chloride, and extracted with ethyl acetate. The organic phase was washed with brine, dried over sodium sulfate, concentrated in vacuo and purified by silica gel column (ethyl acetate/n-hexane=1:3 to 1:1) to obtain the product A7 as a yellow solid (12 g, yield 71%). 1HNMR: (400 MHZ, CDCl3-d6) δ ppm: 7.85 (s, 1H), 7.39 (s, 1H), 4.56 (td, J=9.7, 4.9 Hz, 1H), 4.06 (s, 3H), 2.96-2.86 (m, 1H), 2.79 (dd, J=19.9, 12.3 Hz, 1H), 2.57 (dd, J=29.0, 23.4 Hz, 2H), 2.43 (s, 3H), 2.18 (dd, J=8.1, 3.9 Hz, 2H). LC-MS: (ESI) m/z=328 (M+H)+

Step 2: Add zinc powder (9.93 g, 152.8 mmol) to a solution of A7 (5 g, 15.28 mmol) in acetic acid (250 ml). The mixture was stirred at 30-40 degrees Celsius for 0.5 hour. The reaction solution was poured into ethyl acetate (200 mL) and water (400 mL) and sodium bicarbonate was added to adjust the pH to 7. The organic phase was separated and dried with sodium sulfate. The mixture was filtered and the filtrate was concentrated in vacuo to obtain the product A8 (4.4 g, yield 88.0%) as a yellow oil, which was used directly in the next step. LC-MS: (ESI) m/z=298 (M+H)+

Step 3: The mixture of A8 (4.4 g, 14.8 mmol) and N,N-dimethylformamide dimethyl acetal (8.8 g, 74 mmol) in toluene (50 ml) solution was stirred at 100 degrees Celsius under nitrogen protection for 20 hours. The mixture was concentrated in vacuo to obtain a residue, which was purified with a silica gel column (dichloromethane/methanol=100:1) to obtain the product A9 (3.4 g, 63%) as a yellow oil. 1HNMR: (400 MHZ, DMSO) δ ppm: 7.58 (s, 1H), 7.17 (s, 1H), 6.47 (s, 1H), 4.20 (tt, J=10.1, 5.1 Hz, 1H), 3.88 (s, 3H), 3.08 (s, 6H), 2.90 (ddd, J=18.4, 11.8, 4.4 Hz, 1H), 2.69 (dt, J=30.2, 9.6 Hz, 2H), 2.46 (dd, J=15.2, 8.9 Hz, 1H), 2.39 (s, 3H), 2.08 (s, 2H). LC-MS: (ESI) m/z=353 (M+H)+.

1.4 Synthesis of Quinazoline Derivatives (I)

The synthetic route is as below:

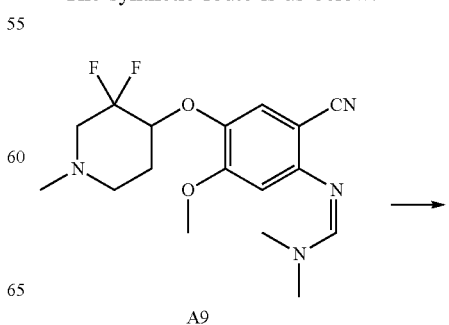

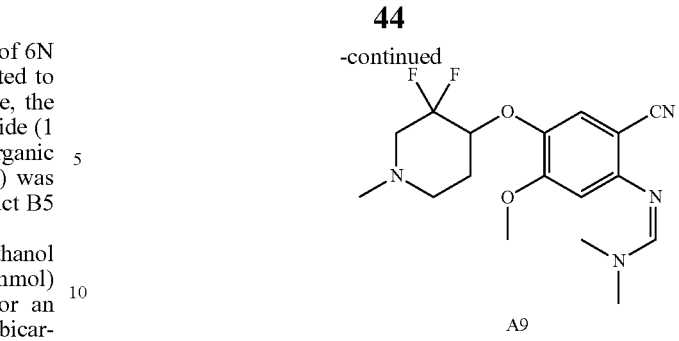

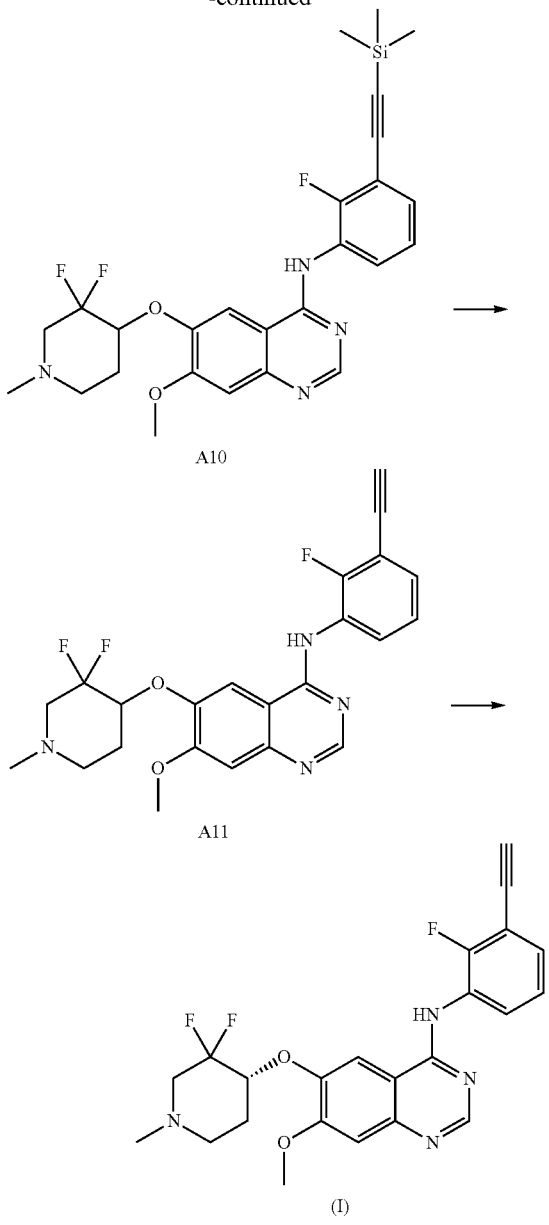

Step 1: A9 (3.4 g, 9.65 mmol) and 2-fluoro-3-((trimethylsilyl) ethynyl) aniline (4 g, 19.3 mmol) in acetic acid (90 ml) at 80° C. was stirred for 16 hours under nitrogen protection. After cooling, the solution was treated with saturated sodium bicarbonate solution to pH=8, and extracted with dichloromethane. The organic phase was dried over sodium sulfate and concentrated in vacuo to obtain a residue, which was purified with a silica gel column (dichloromethane/methanol=100:1) to obtain the product A10 as a white solid (2.4 g, yield 48%). LC-MS: (ESI) m/z=515 (M+H)+

Step 2: Add TBAF (IM tetrahydrofuran solution, 1.94 ml, 1.94 mmol) to a solution of A10 (1 g, 1.94 mmol) in tetrahydrofuran (10 ml), and stir at room temperature for 0.5 hours. The mixture was concentrated in vacuo and purified with silica gel column (dichloromethane/methanol=200:1 to 100:1) to obtain A11 as a yellow solid product (800 mg, yield 93%). 1HNMR: (400 MHZ, CDCl3-d6) δ ppm: 8.74 (s, 1H), 8.63 (td, J=8.0, 1.7 Hz, 1H), 7.42 (s, 1H), 7.35 (d, J=8.5 Hz, 2H), 7.28-7.18 (m, 2H), 4.50 (dd, J=9.5, 4.9 Hz, 1H), 4.05 (s, 3H), 3.38 (s, 1H), 3.07-2.91 (m, 1H), 2.88-2.69 (m, 2H), 2.56 (s, 1H), 2.45 (s, 3H), 2.30-2.13 (m, 2H). LC-MS: (ESI) m/z=443 (M+H)+

Step 3: The racemic mixture A11 (1.03 g) is passed through the high performance liquid phase chiral separation column OJ-H (4.6*100*5 um) using methanol (0.2% methanol ammonia) to obtain the enantiomeric purity (R)/(-) Free base compound (I) (480 mg, ee %>99%, LC-MS: (ESI) m/z=443 (M+H)+).

The above method is a hydrate, which is hygroscopic, and the crystal form changes during the heating process. Due to moisture absorption and thermal instability, it is difficult to make solid preparations under pharmaceutical processing conditions. Therefore, it is necessary to further prepare preferred salt forms and salt crystal forms of quinazoline derivatives with superior physicochemical properties, which can be advantageously used in pharmaceutical processing and pharmaceutical compositions.

Example 2. Preparation of the Hydrochloride Crystal Form a of the Quinazoline Derivative (I) of the Present Invention Weigh about 20 mg of the quinazoline derivative represented by formula (I) (ie, (R)-6-[(3,3-difluoro-1-methylpiperidin-4-yl)oxy]-Nitrogen-(3-ethynyl-2-fluorophenyl)-7-methoxyquinazolin-4-amine (I)) sample was placed in a 1.5 ml vial, 0.6 ml methanol and 46 μl hydrochloric acid (1 mol/L), after stirring for about two days at room temperature, centrifuge to separate the wet solid of the lower layer. According to XRPD detection, the solid is hydrochloride crystal form A.

Example 3. Preparation of the Hydrochloride Crystal Form B of the Quinazoline Derivative (I) of the Present Invention Weigh about 160 mg of a sample of the quinazoline derivative represented by formula (I), add 5 mL of tetrahydrofuran/water (19/1, v/v), and add 0.37 mL of hydrochloric acid (1 mol/L) to the suspension, stirred at room temperature for about two days, and centrifuged to separate the wet solid of the lower layer. Through XRPD detection, the solid is hydrochloride crystal form B.

Example 4. Preparation of the Hydrochloride Crystal Form H of the Quinazoline Derivative (I) of the Present Invention Weigh about 10 mg of the hydrochloride crystal form B sample into a 3 ml vial, add 2 ml of ethanol, filter, and evaporate quickly at room temperature. Through XRPD detection, the obtained solid is hydrochloride crystal form H.

Example 5. Preparation of the Hydrochloride Crystal Form I of the Quinazoline Derivative (I) of the Present Invention Weigh about 10 mg of hydrochloride crystal form H sample, use DSC Q2000 to heat it to 125° C. and then cool to room temperature to obtain hydrochloride crystal form I.

Example 6. Preparation of the Fumarate Crystal Form a of the Quinazoline Derivative (I) of the Present Invention Weigh about 160 mg of the quinazoline derivative represented by formula (I) and 45 mg of fumaric acid sample into a 20 ml glass bottle, add 5 ml of methanol, stir at room temperature for about two days, and collect the solid by centrifugation. Through XRPD detection, the solid is fumarate crystalline form A.

Example 7. Preparation of Succinate Crystal Form a of the Quinazoline Derivative (I) of the Present Invention Weigh about 160 mg of the quinazoline derivative represented by formula (I) and 43 mg of succinic acid sample into a 20 ml glass bottle, add 5 ml of acetone, stir at room temperature for about two days, and centrifuge to collect the solid. According to XRPD detection, the solid is succinate crystal form A.

Example 8. Preparation of Maleate Crystalline Form a of the Quinazoline Derivative (I) of the Present Invention Weigh about 10 mg of the quinazoline derivative represented by formula (I) and 2.6 mg of maleic acid sample into a 1.5 ml glass bottle, add 0.3 ml of acetone, stir at room temperature for about two days, and collect the solid by centrifugation. According to XRPD detection, the solid is maleate salt crystal form A.

Example 9. Preparation of the Glycolate Crystal Form a of the Quinazoline Derivative (I) of the Present Invention Weigh about 150 mg of the quinazoline derivative represented by formula (I) and 27 mg of glycolic acid sample into a 1.5 ml glass bottle, add 5 ml of ethyl acetate, stir at room temperature for about two days, and collect the solid by centrifugation. According to XRPD detection, the solid is glycolate crystal form A.

Example 10. Preparation of the Hydrochloride Crystal Form F of the Quinazoline Derivative (I) of the Present Invention Weigh about 5 mg of the hydrochloride sample into a 3 ml glass vial, and add 0.1 ml of methanol to dissolve it. The resulting clear solution was placed in a 20 ml glass bottle containing 5 ml of isopropyl acetate, and gas-liquid diffused at room temperature until a solid precipitated out. Through XRPD detection, the obtained solid is hydrochloride crystal form F.

Example 11. Preparation of the Hydrochloride Crystal Form C of the Quinazoline Derivative (I) of the Present Invention Weigh about 10 mg of a sample of the quinazoline derivative represented by formula (I), add 0.3 ml of acetonitrile, and added 46 microliters of hydrochloric acid (1 mol/L) to the suspension, stir at room temperature for about two days and then centrifuge to separate the lower wet solid. It was identified as dihydrochloride crystal form C by XRPD detection.

Example 12. Preparation of the Hydrochloride Crystal Form D of the Quinazoline Derivative (I) of the Present Invention Weigh about 2 mg of the hydrochloride crystal form C sample, use DSC Q2000 to heat it to 140 degrees and then cool it to room temperature to obtain the dihydrochloride crystal form D.

Example 13. Preparation of the Sulfate Crystal Form a of the Quinazoline Derivative (I) of the Present Invention Weigh about 10 mg of the quinazoline derivative represented by formula (I) into a 1.5 ml glass bottle, add 0.3 ml methanol and 23 μl sulfuric acid aqueous solution (1 mol/L), stir at room temperature for about two days, and collect by centrifugation solid. After XRPD detection, the solid is sulfate crystal form A.

Example 14. Preparation of the Oxalate Crystal Form a of the Quinazoline Derivative (I) of the Present Invention Weigh about 10 mg of the quinazoline derivative represented by formula (I) and 3.7 mg of adipic acid sample into a 1.5 ml glass bottle, add 0.3 ml methanol, stir at room temperature for about two days, and centrifuge to collect the solid. Through XRPD detection, the solid is adipate salt crystal form A (containing a small amount of unreacted adipic acid, and the characteristic peaks are: 21.6, 25.7).

Example 15. Preparation of the Malate Crystal Form a of the Quinazoline Derivative (I) of the Present Invention Weigh about 10 mg of the quinazoline derivative represented by formula (I) and 2.9 mg of malic acid sample into a 1.5 ml glass bottle, add 0.3 ml of methanol, stir at room temperature for about two days, and collect the solid by centrifugation. Through XRPD detection, the solid is malate crystal form A.

Example 16. Preparation of Benzenesulfonate Crystal Form a of the Quinazoline Derivative (I) of the Present Invention Weigh about 10 mg of the quinazoline derivative represented by formula (I) and 3.7 mg of benzenesulfonic acid sample into a 1.5 ml glass bottle, add 0.3 ml of methanol, stir at room temperature for about two days, and collect the solid by centrifugation. According to XRPD detection, the solid is benzenesulfonate crystal form A.

Example 17. Preparation of Benzenesulfonate Crystal Form B of Quinazoline Derivative (I) of the Present Invention Weigh about 10 mg of the quinazoline derivative represented by formula (I) and 3.5 mg of benzenesulfonic acid sample into a 1.5 ml glass bottle, add 0.3 mil of acetonitrile, stir at room temperature for about two days, and collect the solid by centrifugation. According to XRPD detection, the solid is benzenesulfonate crystal form B.

Example 18. Preparation of Benzenesulfonate Crystal Form C of Quinazoline Derivative (I) of the Present Invention Weigh about 10 mg of the quinazoline derivative of formula (I) and 3.9 mg of benzenesulfonic acid sample into a 1.5 ml glass bottle, add 0.3 ml of a mixed solvent of tetrahydrofuran and water (19:1, v/v), stir at room temperature for about two days, and collect the solid by centrifugation. According to XRPD detection, the solid is benzene sulfonate crystal form C.

Example 19. Preparation of Benzoate Crystal Form a of the Quinazoline Derivative (I) of the Present Invention Weigh about 10 mg of the quinazoline derivative represented by formula (I) and 3.0 mg of benzoic acid sample into a 1.5 ml glass bottle, add 0.3 ml of methanol, stir at room temperature for about two days, and collect the solid by centrifugation. According to XRPD detection, the solid is benzoate crystal form A.

Example 20 Preparation of Hippurate Crystal Form a of the Quinazoline Derivative (I) of the Present Invention Weigh about 10 mg of the quinazoline derivative of formula (I) and 4.2 mg of hippuric acid sample into a 1.5 ml glass bottle, add 0.3 ml of methanol, stir at room temperature for about two days, and collect the solid by centrifugation. According to XRPD detection, the solid is hippurate crystal form A.

Example 21. Preparation of Oxalate Crystal Form a of the Quinazoline Derivative (I) of the Present Invention Weigh about 10 mg of the quinazoline derivative represented by formula (I) and 2.0 mg of oxalic acid sample into a 1.5 ml glass bottle, add 0.3 ml of methanol, stir at room temperature for about two days, and collect the solid by centrifugation. Through XRPD detection, the solid is oxalate crystal form A.

Example 22. Characterize the Crystal Form of the Salt of the Quinazoline Derivative (I) of the Present Invention by XRPD Pattern The XRPD instrument information is as follows:

The XRPD spectrum was collected on Bruker's X-ray powder diffraction analyzer, and the XRPD parameters are shown in Table 1.

TABLE 1

| Parameter | D8 DISCOVER | D2 PHBSER |
|---|---|---|
| XRPD test parameters | | |
| X ray | Cu, kα, Kα1 (Å): 1.54060; Kα2 (Å): 1.54439 Kα2/Kα1 intensity ratio: 0.50 | Cu, kα, Kα1 (Å): 1.54060; Kα2 (Å): 1.54439 Kα2/Kα1 intensity ratio: 0.50 |
| X ray tube setting | 40 kV, 40 mA | 30 kV, 10 mA |
| Divergent slit | automatic | 0.6 mm |
| Monochromator | non | non |
| Scan mode | Step forward | continous |
| Scan range(2Theta) | 4°~45° | 3°~40° |
| Scan step length (2Theta) | 0.005° | 0.0201° |
| Scan time | 100 s | 3 min 30 s |

The XRPD (X-ray powder diffraction) pattern of the hydrochloride crystal form A of the quinazoline derivative (I) prepared according to the method described in this example is shown in FIG. 1, and the specific characteristics are shown in Table 2 below:

TABLE 2

| 2θ (°) | d interval (Å) | intensity % |
|---|---|---|
| 6.48 | 13.65 | 100.00 |
| 7.31 | 12.09 | 26.54 |
| 9.36 | 9.45 | 28.76 |
| 10.26 | 8.63 | 6.97 |
| 13.12 | 6.75 | 55.87 |
| 14.37 | 6.16 | 10.96 |
| 14.98 | 5.91 | 7.43 |
| 16.06 | 5.52 | 9.69 |
| 16.88 | 5.25 | 1.05 |
| 17.48 | 5.07 | 11.02 |
| 18.25 | 4.86 | 17.80 |
| 20.01 | 4.44 | 16.47 |
| 20.83 | 4.27 | 9.83 |
| 21.55 | 4.12 | 17.46 |
| 22.21 | 4.00 | 4.60 |
| 23.35 | 3.81 | 10.36 |
| 25.47 | 3.50 | 9.62 |
| 26.60 | 3.35 | 18.17 |
| 27.46 | 3.25 | 20.92 |
| 28.29 | 3.15 | 9.60 |
| 29.98 | 2.98 | 6.02 |
| 34.07 | 2.63 | 5.22 |
| 34.89 | 2.57 | 6.06 |
| 36.25 | 2.48 | 1.94 |
| 36.47 | 2.46 | 3.68 |
| 36.87 | 2.44 | 8.56 |
| 37.54 | 2.40 | 5.78 |

Figure 2:
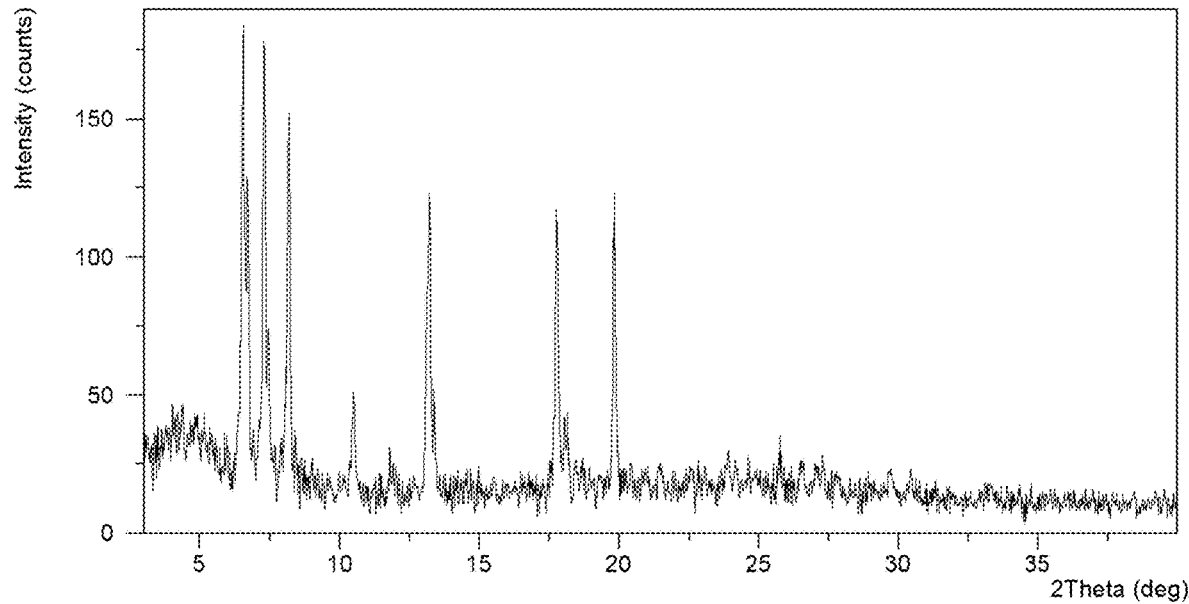
FIG. 2 is the XRPD pattern of the hydrochloride crystal form B of the quinazoline derivative of the present invention.

The XRPD (X-ray powder diffraction) pattern of the hydrochloride crystal form B of the quinazoline derivative (I) prepared according to the method described in the example is shown in FIG. 2 and the specific characteristics are shown in Table 3 below.

TABLE 3

| 2θ (°) | d interval (Å) | intensity % |
|---|---|---|
| 4.32 | 20.43 | 10.65 |
| 5.98 | 14.77 | 14.42 |
| 6.54 | 13.52 | 100.00 |
| 7.28 | 12.15 | 83.40 |
| 8.17 | 10.82 | 64.39 |
| 10.52 | 8.41 | 14.72 |
| 13.20 | 6.71 | 67.57 |
| 15.99 | 5.54 | 9.15 |
| 17.74 | 5.00 | 65.39 |
| 18.48 | 4.80 | 13.80 |
| 19.32 | 4.59 | 6.19 |
| 19.84 | 4.48 | 61.43 |
| 22.56 | 3.94 | 8.48 |
| 23.88 | 3.73 | 10.25 |
| 24.36 | 3.65 | 6.26 |
| 24.87 | 3.58 | 7.11 |
| 30.47 | 2.93 | 13.11 |
| 32.92 | 2.72 | 7.75 |
| 33.55 | 2.67 | 7.40 |
| 34.60 | 2.59 | 8.11 |
| 38.06 | 2.36 | 20.93 |
| 38.34 | 2.35 | 3.89 |

Figure 3:
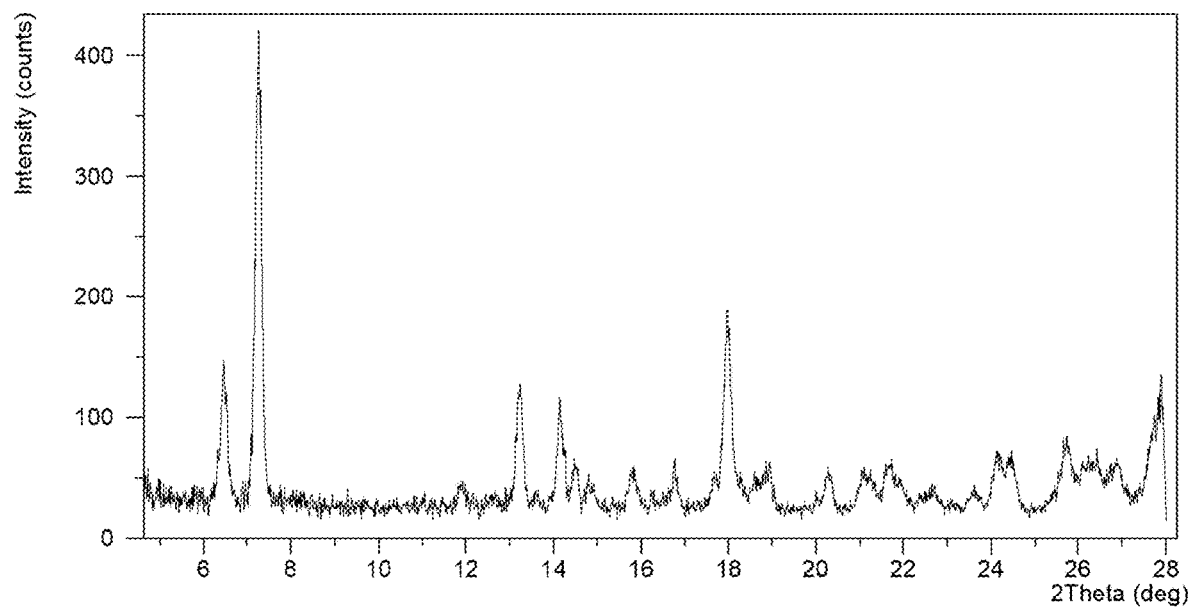
FIG. 3 is the XRPD pattern of the hydrochloride crystal form H of the quinazoline derivative of the present invention.

The XRPD (X-ray powder diffraction) pattern of the hydrochloride crystal form H of the quinazoline derivative (I) prepared according to the method described in this example is shown in FIG. 3, and the specific characteristics are shown in Table 4 below:

TABLE 4

| 2θ (°) | d interval (Å) | intensity % |
|---|---|---|
| 5.83 | 15.16 | 1.64 |
| 6.43 | 13.74 | 27.01 |

TABLE 4-continued

| 2θ (°) | d interval (Å) | intensity % |
|---|---|---|
| 7.26 | 12.18 | 100.00 |
| 8.10 | 10.92 | 2.45 |
| 10.24 | 8.64 | 3.29 |
| 11.93 | 7.42 | 7.64 |
| 13.22 | 6.70 | 28.87 |
| 14.11 | 6.28 | 17.61 |
| 14.45 | 6.13 | 11.91 |
| 14.88 | 5.95 | 5.96 |
| 15.78 | 5.62 | 9.59 |
| 16.80 | 5.28 | 6.82 |
| 17.95 | 4.94 | 37.20 |
| 18.96 | 4.68 | 11.84 |
| 20.25 | 4.38 | 12.29 |
| 21.07 | 4.22 | 9.25 |
| 21.65 | 4.10 | 10.40 |
| 24.16 | 3.68 | 13.72 |
| 24.53 | 3.63 | 10.78 |
| 25.67 | 3.47 | 13.28 |
| 26.37 | 3.38 | 11.20 |
| 27.03 | 3.30 | 9.20 |
| 27.61 | 3.23 | 16.18 |

Figure 4:
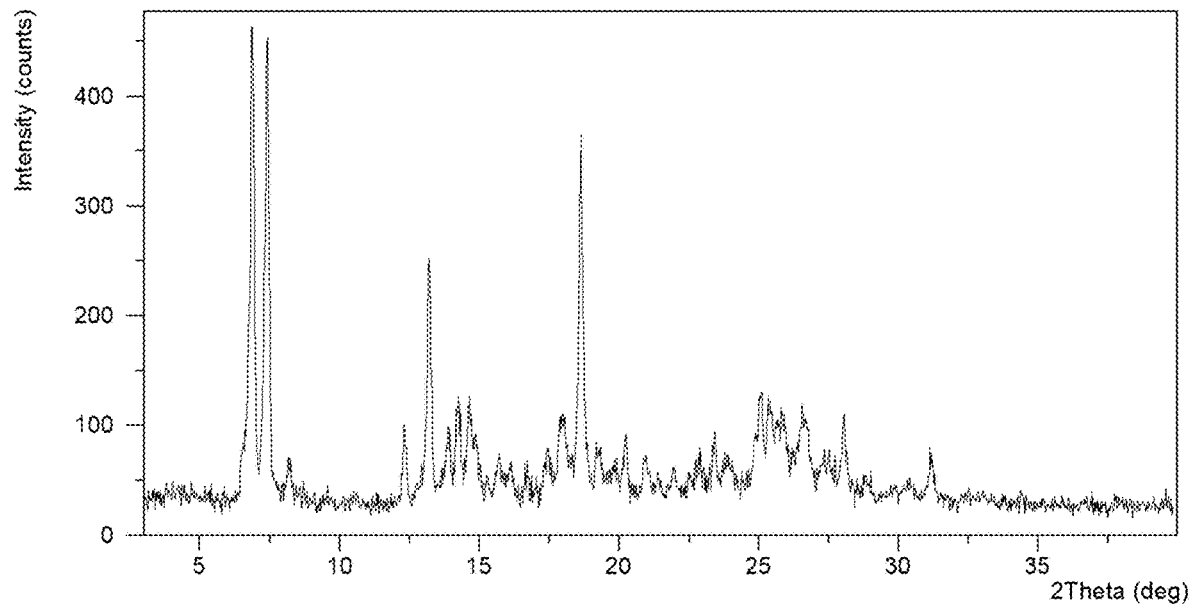
FIG. 4 is the XRPD pattern of the hydrochloride crystal form I of the quinazoline derivative of the present invention.

The XRPD (X-ray powder diffraction) pattern of the hydrochloride crystal form I of the quinazoline derivative (I) prepared according to the method described in this example is shown in FIG. 4, and the specific characteristics are shown in Table 5 below:

TABLE 5

| 2θ (°) | d interval (Å) | intensity % |
|---|---|---|
| 6.88 | 12.85 | 100.00 |
| 7.42 | 11.91 | 97.68 |
| 8.20 | 10.78 | 8.24 |
| 12.31 | 7.19 | 17.36 |
| 13.20 | 6.71 | 49.95 |
| 13.88 | 6.38 | 15.34 |
| 14.23 | 6.23 | 21.47 |
| 14.66 | 6.04 | 20.32 |
| 15.69 | 5.65 | 9.51 |
| 17.48 | 5.07 | 11.13 |
| 17.90 | 4.96 | 16.49 |
| 18.64 | 4.76 | 77.90 |
| 19.23 | 4.62 | 10.81 |
| 20.24 | 4.39 | 13.48 |
| 20.92 | 4.25 | 9.65 |
| 21.94 | 4.05 | 6.82 |
| 22.88 | 3.89 | 8.61 |
| 23.42 | 3.80 | 13.22 |
| 23.88 | 3.73 | 8.97 |
| 25.12 | 3.55 | 23.66 |
| 25.40 | 3.51 | 20.41 |
| 25.85 | 3.45 | 18.27 |
| 26.64 | 3.35 | 17.86 |
| 28.07 | 3.18 | 18.29 |
| 28.92 | 3.09 | 4.53 |
| 31.19 | 2.87 | 9.34 |
| 33.10 | 2.71 | 1.30 |

Figure 5:
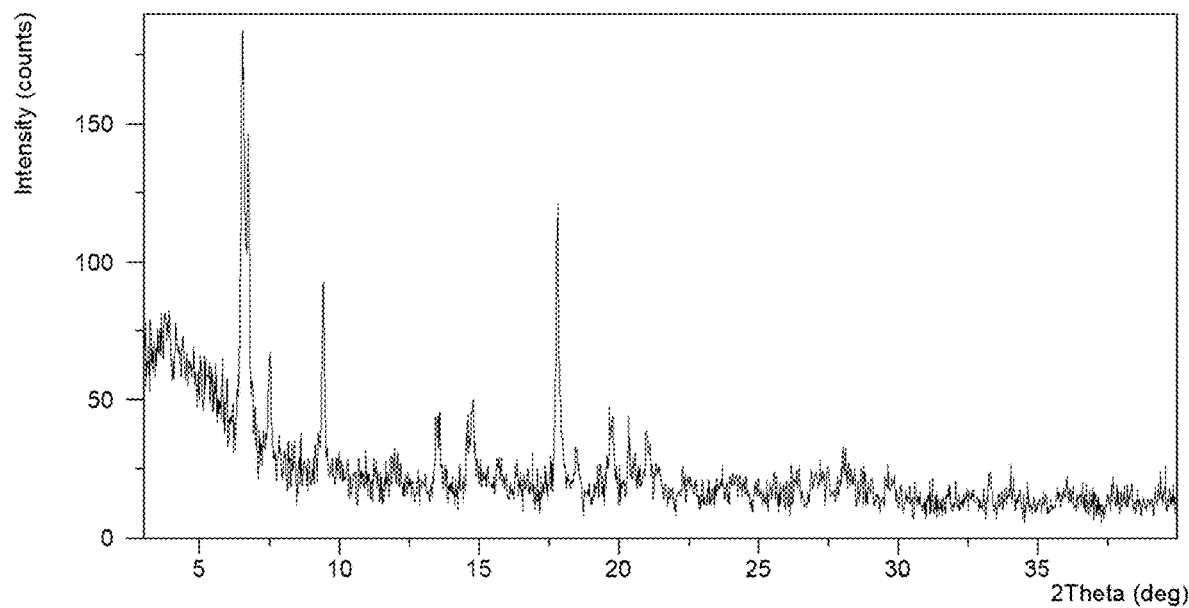
FIG. 5 is the XRPD pattern of the fumarate crystal form A of the quinazoline derivative of the present invention.

The XRPD (X-ray powder diffraction) pattern of the fumarate crystalline form A of the quinazoline derivative (I) prepared according to the method described in the example is shown in FIG. 5, and the specific characteristics are shown in Table 6 below:

TABLE 6

| 2θ (°) | d interval (Å) | intensity % |
|---|---|---|
| 6.51 | 13.57 | 100.00 |
| 6.74 | 13.12 | 71.99 |
| 7.47 | 11.84 | 27.67 |

TABLE 6-continued

| 2θ (°) | d interval (Å) | intensity % |
|---|---|---|
| 9.37 | 9.44 | 54.52 |
| 10.82 | 8.18 | 8.39 |
| 13.43 | 6.59 | 31.96 |
| 13.97 | 6.34 | 7.96 |
| 14.61 | 6.06 | 18.74 |
| 17.78 | 4.99 | 74.99 |
| 18.51 | 4.79 | 16.32 |
| 18.80 | 4.72 | 12.77 |
| 19.69 | 4.51 | 26.88 |
| 20.90 | 4.25 | 13.86 |
| 21.36 | 4.16 | 16.83 |
| 21.68 | 4.10 | 14.21 |
| 22.63 | 3.93 | 18.38 |
| 23.76 | 3.74 | 14.79 |
| 24.39 | 3.65 | 12.80 |
| 27.09 | 3.29 | 13.22 |
| 28.73 | 3.11 | 14.84 |
| 29.69 | 3.01 | 8.29 |
| 30.52 | 2.93 | 11.72 |
| 31.07 | 2.88 | 8.48 |
| 35.14 | 2.55 | 13.84 |
| 36.12 | 2.49 | 8.55 |
| 38.33 | 2.35 | 5.29 |

Figure 6:
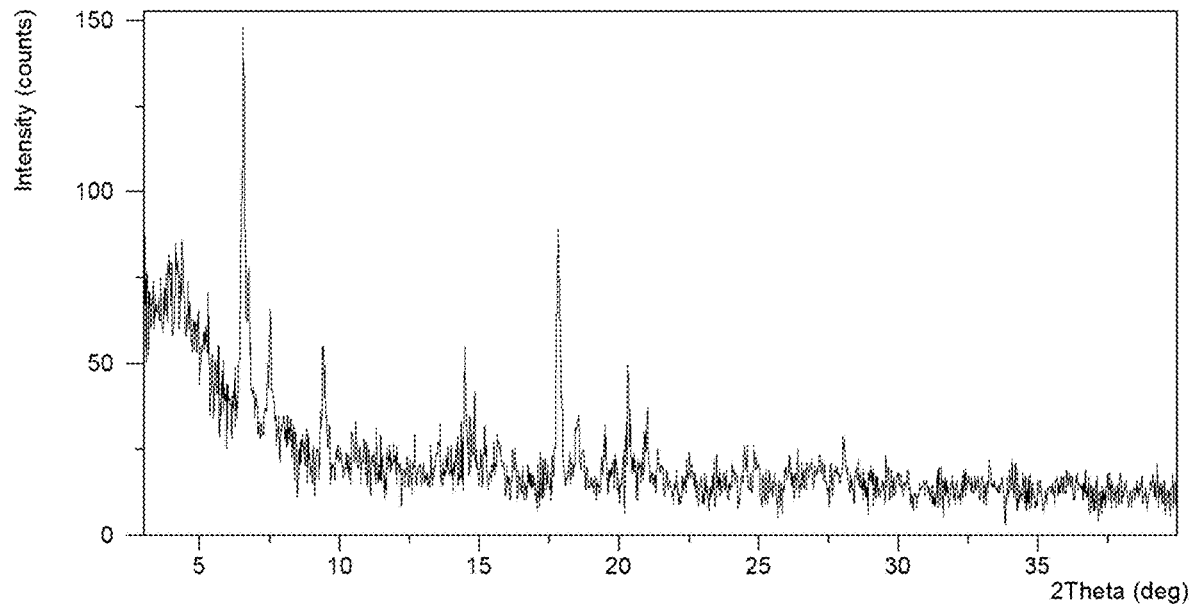
FIG. 6 is the XRPD pattern of the succinate crystal form A of the quinazoline derivative of the present invention.

The XRPD (X-ray powder diffraction) pattern of the succinate crystal form A of the quinazoline derivative (I) prepared according to the method described in the example is shown in FIG. 6, and the specific characteristics are shown in Table 7 as follows:

TABLE 7

| 2θ (°) | d interval (Å) | intensity % |
|---|---|---|
| 3.92 | 22.54 | 48.67 |
| 4.40 | 20.07 | 54.30 |
| 6.56 | 13.48 | 100.00 |
| 6.74 | 13.11 | 50.34 |
| 7.50 | 11.79 | 35.85 |
| 9.42 | 9.39 | 30.37 |
| 11.92 | 7.42 | 7.85 |
| 12.68 | 6.98 | 13.50 |
| 13.53 | 6.55 | 10.64 |
| 14.50 | 6.11 | 32.67 |
| 14.84 | 5.97 | 16.05 |
| 15.22 | 5.82 | 11.16 |
| 15.68 | 5.65 | 10.29 |
| 16.25 | 5.45 | 7.51 |
| 17.82 | 4.98 | 59.49 |
| 18.55 | 4.78 | 16.72 |
| 19.48 | 4.56 | 10.64 |
| 20.34 | 4.37 | 24.77 |
| 20.99 | 4.23 | 15.45 |
| 22.08 | 4.03 | 3.93 |
| 22.59 | 3.94 | 5.43 |
| 24.14 | 3.69 | 3.47 |
| 24.52 | 3.63 | 6.11 |
| 24.92 | 3.57 | 6.57 |
| 28.07 | 3.18 | 9.48 |
| 30.92 | 2.89 | 2.04 |
| 36.11 | 2.49 | 3.27 |

Figure 7:
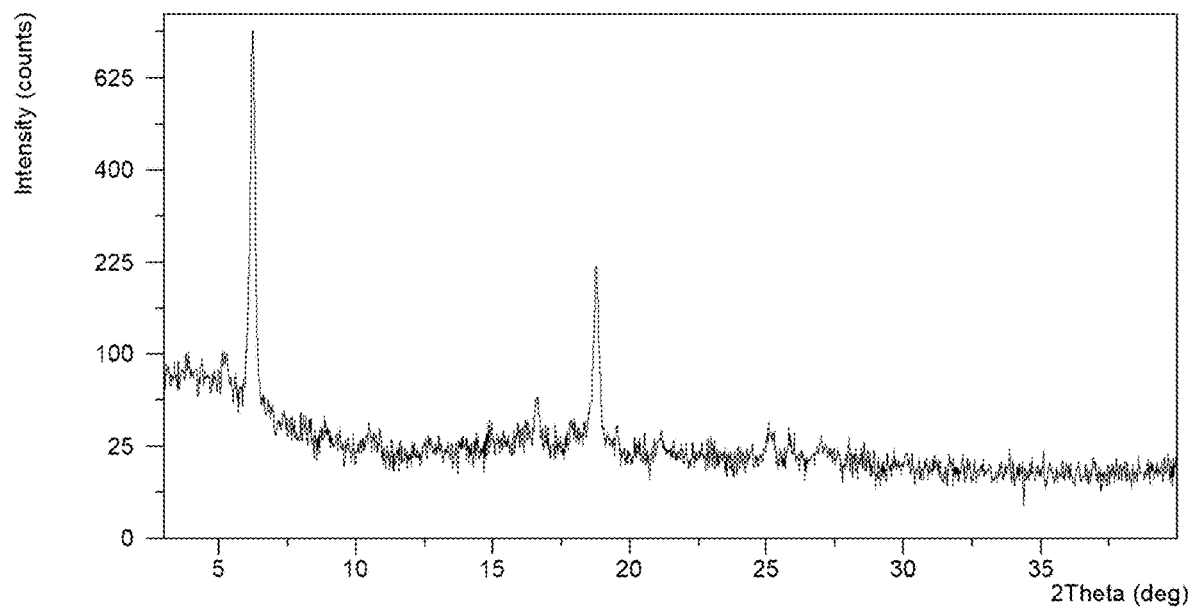
FIG. 7 is the XRPD pattern of the maleate crystal form A of the quinazoline derivative of the present invention.

The maleate crystalline form A of the quinazoline derivative (I) prepared according to the method described in the example, and its XRPD (X-ray powder diffraction) pattern is shown in FIG. 7, and the specific characteristics are shown in Table 8 below:

TABLE 8

| 2θ (°) | d interval (Å) | intensity % |
|---|---|---|
| 6.25 | 14.14 | 100 |
| 8.44 | 10.47 | 2.75 |

TABLE 8-continued

| 2θ (°) | d interval (Å) | intensity % |
|---|---|---|
| 8.68 | 10.19 | 2.32 |
| 9.42 | 9.39 | 1.76 |
| 10.41 | 8.49 | 1.63 |
| 14.42 | 6.14 | 5.46 |
| 14.88 | 5.95 | 2.71 |
| 16.65 | 5.32 | 4.81 |
| 17.93 | 4.95 | 4.18 |
| 18.78 | 4.72 | 30.04 |
| 20.58 | 4.32 | 1.8 |
| 21.17 | 4.20 | 4.98 |
| 22.63 | 3.93 | 2.27 |
| 25.16 | 3.54 | 2.06 |
| 31.15 | 2.87 | 2.03 |
| 32.40 | 2.76 | 2.29 |
| 33.66 | 2.66 | 1.16 |
| 34.34 | 2.61 | 6.93 |
| 34.52 | 2.60 | 0.3 |
| 35.82 | 2.51 | 3.8 |
| 36.06 | 2.49 | 3.44 |
| 36.35 | 2.47 | 1.59 |
| 36.91 | 2.44 | 3.14 |

Figure 8:
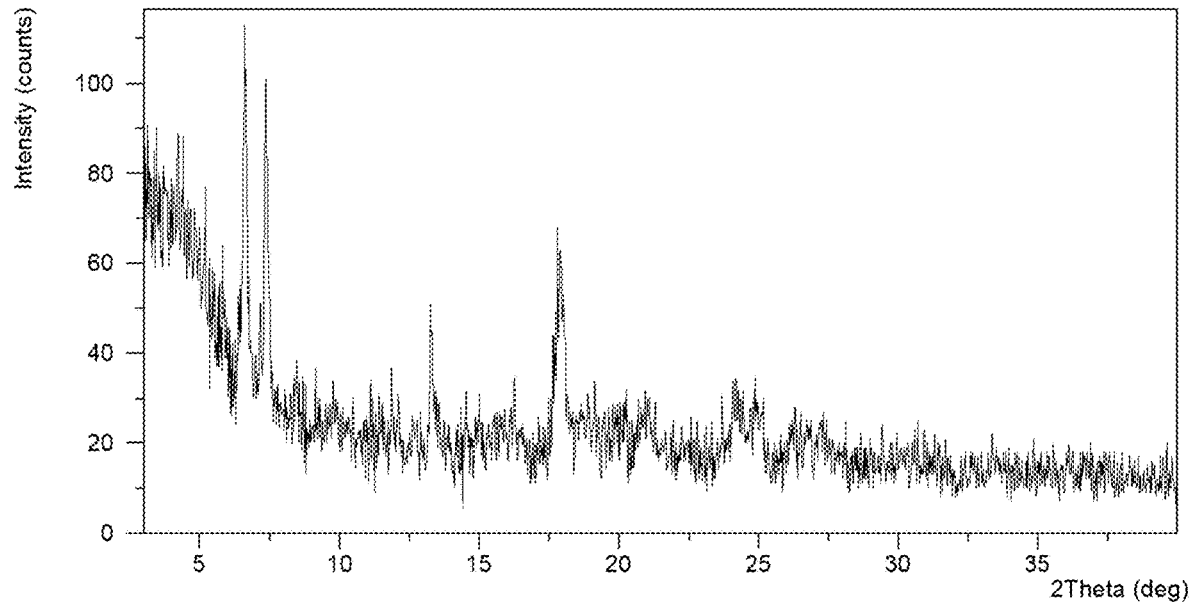
FIG. 8 is the XRPD pattern of the glycolate crystal form A of the quinazoline derivative of the present invention.

The XRPD (X-ray powder diffraction) pattern of the glycolate crystal form A of the quinazoline derivative (I) prepared according to the method described in the example is shown in FIG. 8, and the specific characteristics are shown in Table 9 below:

TABLE 9

| 2θ (°) | d interval (Å) | intensity % |
|---|---|---|
| 4.53 | 19.50 | 20.70 |
| 5.89 | 15.02 | 18.57 |
| 6.59 | 13.42 | 100.00 |
| 7.35 | 12.03 | 85.28 |
| 10.02 | 8.83 | 9.88 |
| 12.54 | 7.06 | 11.61 |
| 13.26 | 6.68 | 33.29 |
| 15.94 | 5.56 | 19.09 |
| 17.93 | 4.95 | 65.13 |
| 18.67 | 4.75 | 35.91 |
| 19.36 | 4.59 | 7.40 |
| 19.84 | 4.47 | 24.04 |
| 21.06 | 4.22 | 22.28 |
| 24.99 | 3.56 | 25.31 |
| 31.13 | 2.87 | 9.99 |
| 33.48 | 2.68 | 9.51 |
| 34.79 | 2.58 | 17.41 |
| 35.56 | 2.52 | 9.75 |
| 36.17 | 2.48 | 15.75 |

Figure 9:
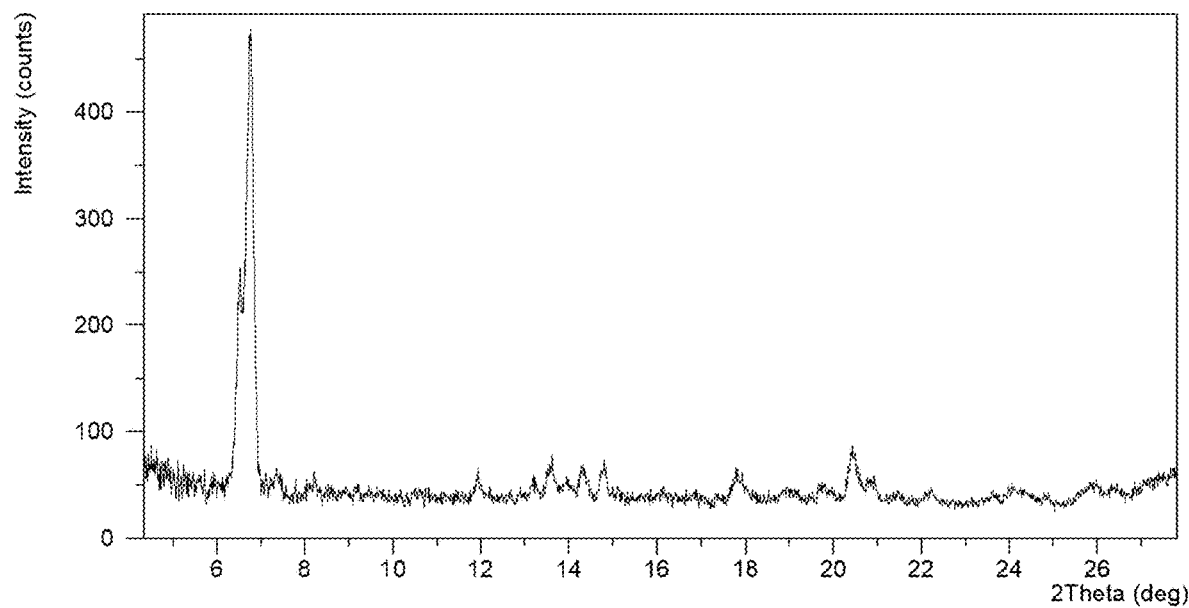
FIG. 9 is the XRPD pattern of the hydrochloride crystal form F of the quinazoline derivative of the present invention.

The XRPD (X-ray powder diffraction) pattern of the hydrochloride crystal form F of the quinazoline derivative (I) prepared according to the method described in the examples is shown in FIG. 9, and the specific characteristics are shown in Table 10 as follows:

TABLE 10

| 2θ (°) | d interval (Å) | intensity % |
|---|---|---|
| 4.91 | 17.98 | 9.02 |
| 5.67 | 15.57 | 7.81 |
| 6.51 | 13.59 | 50.42 |
| 6.77 | 13.06 | 100.00 |
| 7.44 | 11.87 | 5.20 |
| 8.58 | 10.31 | 5.22 |
| 9.20 | 9.61 | 6.12 |
| 9.73 | 9.09 | 4.79 |
| 10.40 | 8.51 | 4.49 |
| 10.85 | 8.16 | 4.26 |

TABLE 10-continued

| 2θ (°) | d interval (Å) | intensity % |
|---|---|---|
| 11.86 | 7.46 | 5.27 |
| 13.58 | 6.52 | 11.73 |
| 14.30 | 6.19 | 8.38 |
| 14.78 | 5.99 | 9.78 |
| 15.57 | 5.69 | 2.30 |
| 15.85 | 5.59 | 6.03 |
| 16.15 | 5.49 | 5.07 |
| 16.41 | 5.40 | 3.73 |
| 16.97 | 5.22 | 2.92 |
| 17.89 | 4.96 | 6.05 |
| 18.96 | 4.68 | 2.55 |
| 19.76 | 4.49 | 6.03 |
| 20.45 | 4.34 | 12.55 |
| 20.79 | 4.27 | 7.04 |
| 21.57 | 4.12 | 2.46 |
| 22.21 | 4.00 | 3.82 |
| 24.17 | 3.68 | 5.86 |

Figure 10:
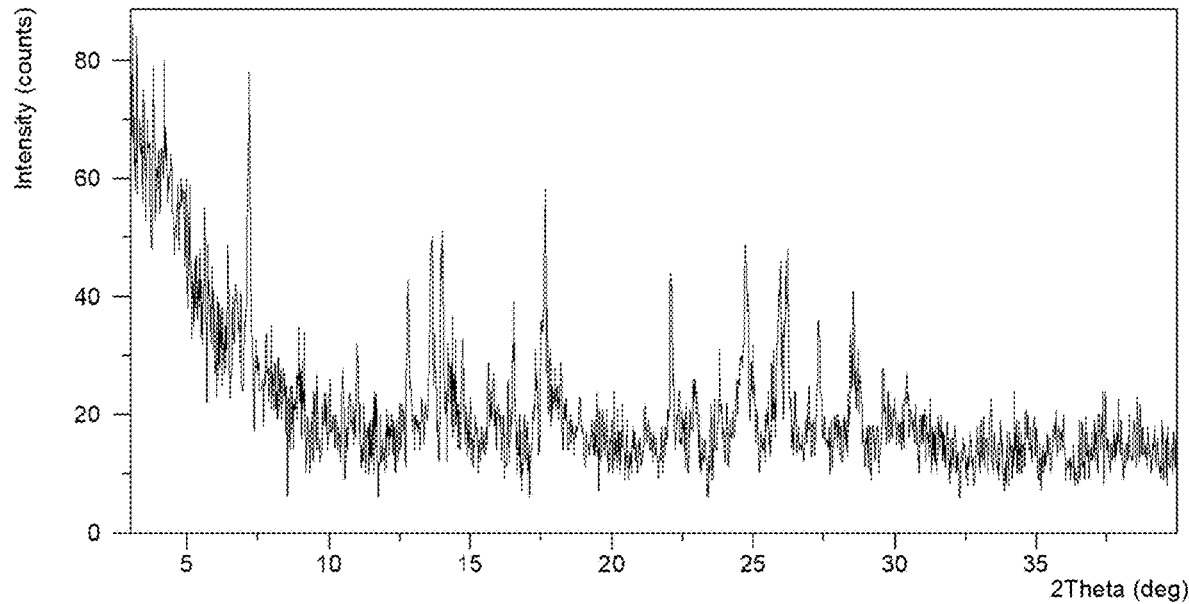
FIG. 10 is the XRPD pattern of the hydrochloride crystal form C of the quinazoline derivative of the present invention.

The XRPD (X-ray powder diffraction) pattern of the hydrochloride crystal form C of the quinazoline derivative (I) prepared according to the method described in the example is shown in FIG. 10, and the specific characteristics are shown in Table 11:

TABLE 11

| 2θ (°) | d interval (Å) | intensity % |
|---|---|---|
| 5.66 | 15.62 | 33.04 |
| 7.16 | 12.35 | 86.93 |
| 8.32 | 10.63 | 35.43 |
| 8.86 | 9.99 | 9.96 |
| 9.52 | 9.29 | 43.38 |
| 10.98 | 8.06 | 31.53 |
| 11.63 | 7.61 | 24.27 |
| 12.80 | 6.91 | 83.87 |
| 13.57 | 6.52 | 90.81 |
| 13.96 | 6.35 | 97.70 |
| 14.81 | 5.98 | 16.18 |
| 15.14 | 5.85 | 38.19 |
| 15.49 | 5.72 | 21.63 |
| 16.55 | 5.36 | 41.89 |
| 16.86 | 5.26 | 17.41 |
| 17.61 | 5.04 | 83.88 |
| 22.04 | 4.03 | 92.45 |
| 22.93 | 3.88 | 61.61 |
| 24.55 | 3.63 | 70.53 |
| 26.19 | 3.40 | 100.00 |
| 27.30 | 3.27 | 62.72 |
| 28.49 | 3.13 | 68.11 |
| 34.12 | 2.63 | 38.44 |
| 34.76 | 2.58 | 33.38 |
| 35.65 | 2.52 | 28.87 |
| 36.68 | 2.45 | 35.40 |
| 37.31 | 2.41 | 13.91 |
| 37.80 | 2.38 | 15.63 |
| 38.20 | 2.36 | 22.61 |
| 38.53 | 2.34 | 25.44 |

Figure 11:
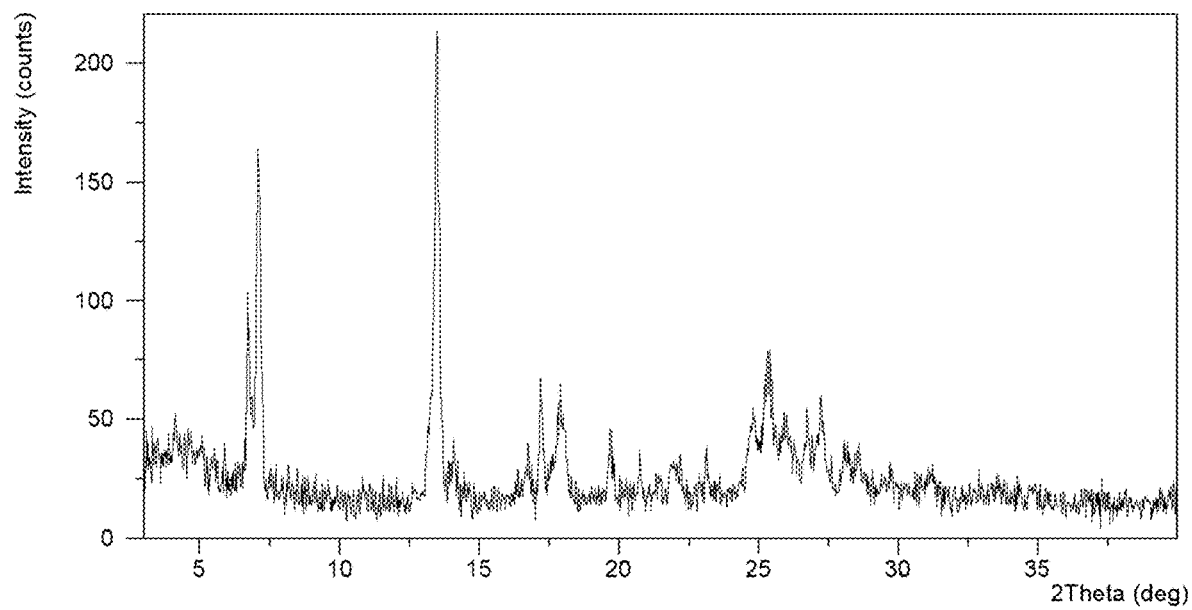
FIG. 11 is the XRPD pattern of the hydrochloride crystal form D of the quinazoline derivative of the present invention.

The XRPD (X-ray powder diffraction) pattern of the hydrochloride crystal form D of the quinazoline derivative (I) prepared according to the method described in the example is shown in FIG. 11, and the specific characteristics are shown in Table 12 below:

TABLE 12

| 2θ (°) | d interval (Å) | intensity % |
|---|---|---|
| 3.43 | 25.78 | 9.33 |
| 6.72 | 13.15 | 38.93 |
| 7.12 | 12.42 | 86.35 |
| 8.47 | 10.44 | 5.19 |

TABLE 12-continued

| 2θ (°) | d interval (Å) | intensity % |
|---|---|---|
| 9.32 | 9.49 | 3.98 |
| 12.25 | 7.23 | 7.24 |
| 13.44 | 6.59 | 100.00 |
| 14.07 | 6.29 | 20.81 |
| 15.69 | 5.65 | 6.22 |
| 16.87 | 5.26 | 17.79 |
| 17.22 | 5.15 | 24.68 |
| 17.97 | 4.94 | 20.14 |
| 19.77 | 4.49 | 12.84 |
| 20.73 | 4.28 | 10.55 |
| 22.25 | 3.99 | 14.23 |
| 22.82 | 3.90 | 10.95 |
| 23.64 | 3.76 | 11.90 |
| 24.77 | 3.59 | 30.77 |
| 25.40 | 3.51 | 31.28 |
| 27.28 | 3.27 | 25.13 |
| 28.13 | 3.17 | 20.61 |
| 29.69 | 3.01 | 11.39 |
| 31.01 | 2.88 | 16.75 |
| 33.48 | 2.68 | 7.57 |
| 34.87 | 2.57 | 11.22 |
| 35.42 | 2.53 | 6.02 |
| 38.08 | 2.36 | 8.64 |

Figure 12:
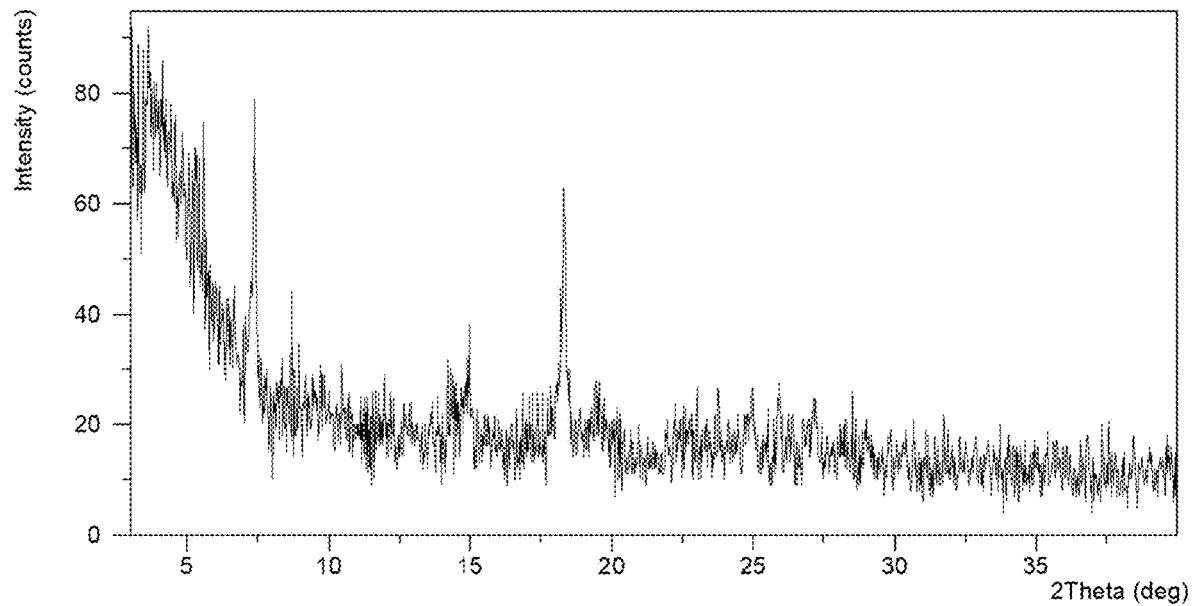
FIG. 12 is the XRPD pattern of the sulfate crystal form A of the quinazoline derivative of the present invention.

The XRPD (X-ray powder diffraction) pattern of the sulfate salt form A of the quinazoline derivative (1) prepared according to the method described in the examples is shown in FIG. 12, and the specific characteristics are shown in Table: 13 as follows:

TABLE 13

| 2θ (°) | d interval (Å) | intensity % |
|---|---|---|
| 7.27 | 12.16 | 55.90 |
| 8.41 | 10.52 | 28.51 |
| 11.88 | 7.45 | 21.62 |
| 14.96 | 5.92 | 30.80 |
| 18.23 | 4.87 | 100.00 |
| 19.68 | 4.51 | 27.10 |
| 20.64 | 4.30 | 27.34 |
| 24.83 | 3.59 | 19.09 |
| 25.82 | 3.45 | 27.70 |
| 27.10 | 3.29 | 28.16 |
| 28.16 | 3.17 | 31.15 |
| 29.79 | 3.00 | 23.79 |
| 30.71 | 2.91 | 18.14 |
| 32.35 | 2.77 | 29.11 |
| 34.12 | 2.63 | 20.99 |
| 35.56 | 2.52 | 18.44 |
| 37.56 | 2.39 | 30.83 |
| 38.37 | 2.35 | 27.20 |

Figure 13:
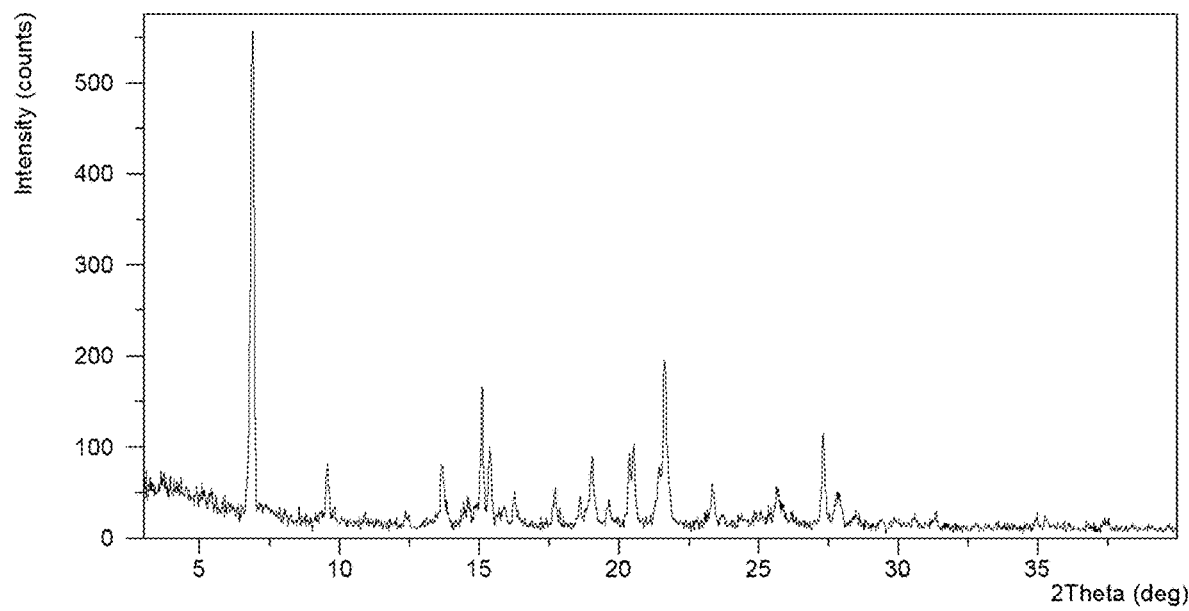
FIG. 13 is the XRPD pattern of the oxalate crystal form A of the quinazoline derivative of the present invention.

The XRPD (X-ray powder diffraction) pattern of the oxalate crystal form A of the quinazoline derivative (I) prepared according to the method described in the example is shown in FIG. 13, and the specific characteristics are shown in Table 14 below:

TABLE 14

| 2θ (°) | d interval (Å) | intensity % |
|---|---|---|
| 5.43 | 16.28 | 4.62 |
| 6.88 | 12.84 | 100.00 |
| 7.38 | 11.99 | 2.32 |
| 9.56 | 9.25 | 13.26 |
| 13.68 | 6.47 | 12.35 |
| 15.10 | 5.87 | 25.06 |
| 15.43 | 5.74 | 14.65 |
| 16.32 | 5.43 | 5.52 |
| 16.88 | 5.25 | 2.12 |
| 17.68 | 5.02 | 6.18 |

TABLE 14-continued

| 2θ (°) | d interval (Å) | intensity % |
|---|---|---|
| 18.60 | 4.77 | 5.49 |
| 19.02 | 4.67 | 11.86 |
| 20.58 | 4.32 | 10.78 |
| 21.62 | 4.11 | 30.00 |
| 22.33 | 3.98 | 1.87 |
| 22.70 | 3.92 | 3.06 |
| 23.35 | 3.81 | 8.15 |
| 25.68 | 3.47 | 9.46 |
| 27.29 | 3.27 | 16.42 |
| 27.88 | 3.20 | 8.65 |
| 28.53 | 3.13 | 2.63 |
| 29.37 | 3.04 | 4.32 |
| 31.35 | 2.85 | 3.57 |
| 34.89 | 2.57 | 2.24 |
| 37.11 | 2.42 | 2.18 |
| 37.78 | 2.38 | 1.11 |
| 38.17 | 2.36 | 5.10 |
| 38.36 | 2.35 | 3.11 |
| 39.65 | 2.27 | 2.74 |

Figure 14:
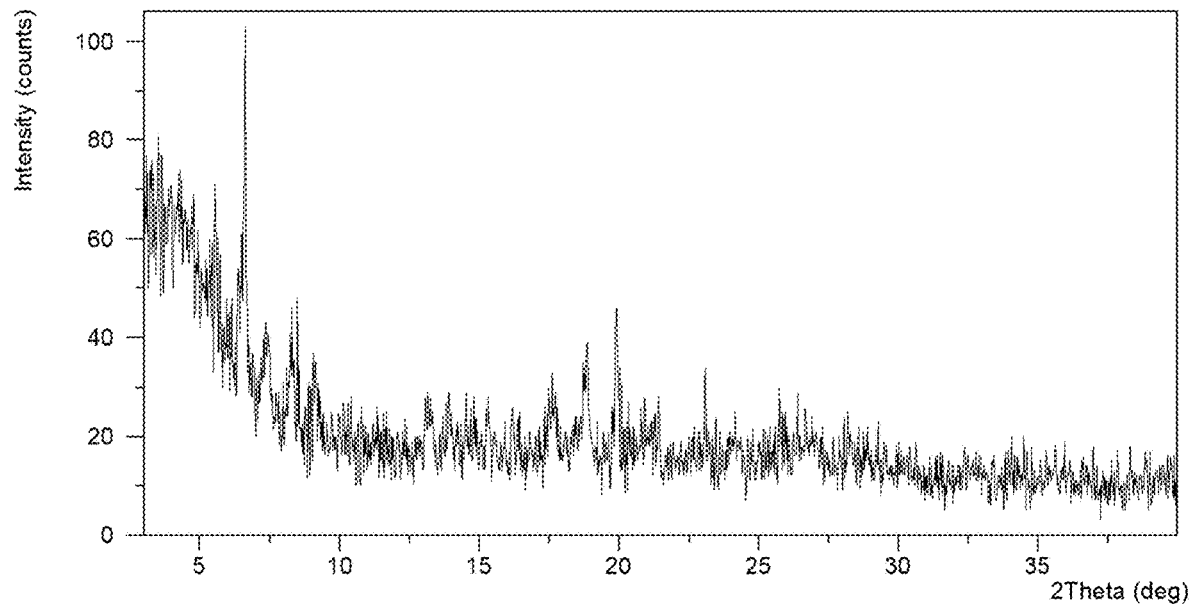
FIG. 14 is the XRPD pattern of the malate salt crystal form A of the quinazoline derivative of the present invention.

The XRPD (X-ray powder diffraction) pattern of the malate crystalline form A of the quinazoline derivative (I) prepared according to the method described in the examples is shown in FIG. 14, and the specific characteristics are shown in Table 15 below:

TABLE 15

| 2θ (°) | d interval (Å) | intensity % |
|---|---|---|
| 5.43 | 16.26 | 57.27 |
| 6.53 | 13.53 | 100.00 |
| 7.49 | 11.81 | 50.28 |
| 8.35 | 10.59 | 41.91 |
| 9.17 | 9.65 | 41.90 |
| 12.10 | 7.32 | 32.80 |
| 13.16 | 6.73 | 23.60 |
| 16.17 | 5.48 | 20.44 |
| 18.77 | 4.73 | 62.34 |
| 19.85 | 4.47 | 59.43 |
| 20.79 | 4.27 | 32.77 |
| 23.14 | 3.84 | 30.64 |
| 23.94 | 3.72 | 42.73 |
| 26.66 | 3.34 | 56.34 |
| 28.25 | 3.16 | 44.75 |
| 29.32 | 3.05 | 44.89 |
| 30.38 | 2.94 | 47.42 |
| 33.24 | 2.70 | 41.53 |
| 33.69 | 2.66 | 47.81 |
| 34.80 | 2.58 | 45.71 |
| 35.97 | 2.50 | 40.03 |
| 36.87 | 2.44 | 27.00 |
| 37.88 | 2.38 | 23.73 |

Figure 15:
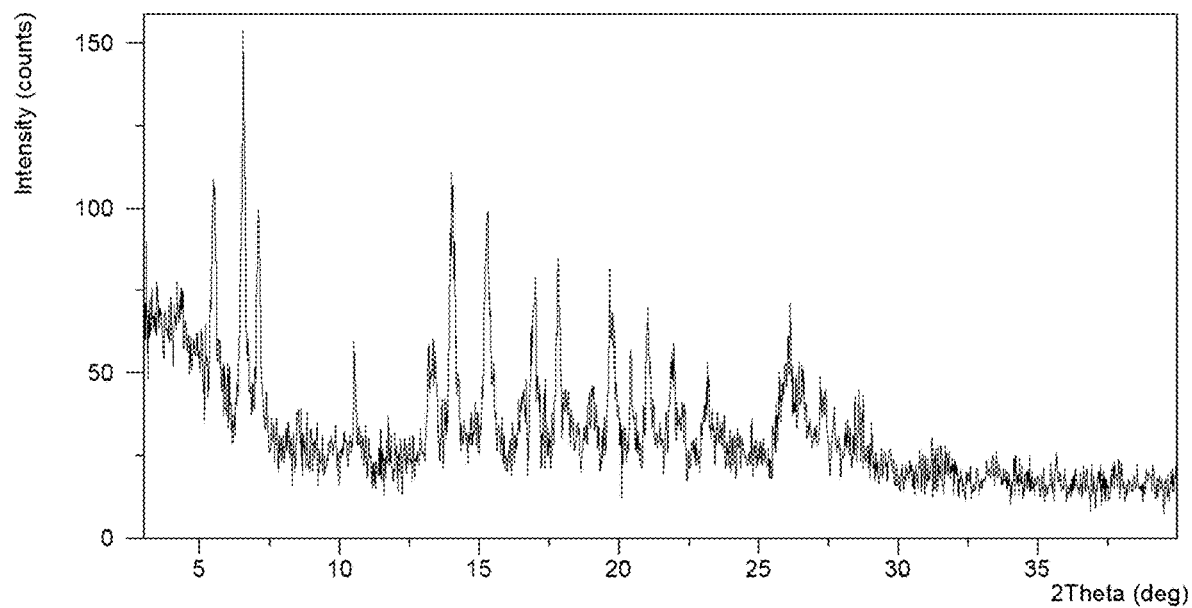
FIG. 15 is the XRPD pattern of the benzenesulfonate crystal form A of the quinazoline derivative of the present invention.

The XRPD (X-ray powder diffraction) pattern of the benzenesulfonate crystal form A of the quinazoline derivative (I) prepared according to the method described in the examples is shown in FIG. 15, and the specific characteristics are shown in Table 16 below.

TABLE 16

| 2θ (°) | d interval (Å) | intensity % |
|---|---|---|
| 5.48 | 16.12 | 57.97 |
| 6.56 | 13.47 | 100.00 |
| 7.08 | 12.49 | 58.05 |
| 7.65 | 11.56 | 8.79 |
| 8.14 | 10.86 | 10.62 |
| 8.48 | 10.42 | 11.86 |
| 9.71 | 9.11 | 8.71 |
| 10.55 | 8.39 | 16.18 |
| 11.14 | 7.94 | 4.47 |

TABLE 16-continued

| 2θ (°) | d interval (Å) | intensity % |
|---|---|---|
| 11.77 | 7.52 | 7.18 |
| 13.32 | 6.65 | 29.39 |
| 13.95 | 6.35 | 90.84 |
| 15.32 | 5.78 | 76.40 |
| 16.46 | 5.39 | 27.63 |
| 16.89 | 5.25 | 47.92 |
| 17.82 | 4.98 | 52.43 |
| 19.15 | 4.64 | 29.86 |
| 19.70 | 4.51 | 57.09 |
| 20.43 | 4.35 | 31.70 |
| 21.02 | 4.23 | 37.94 |
| 21.98 | 4.04 | 27.90 |
| 22.68 | 3.92 | 23.14 |
| 23.23 | 3.83 | 37.88 |
| 25.26 | 3.53 | 24.85 |
| 26.07 | 3.42 | 53.20 |
| 26.59 | 3.35 | 43.79 |
| 28.63 | 3.12 | 20.84 |
| 29.09 | 3.07 | 16.07 |
| 30.45 | 2.94 | 16.85 |
| 31.12 | 2.87 | 16.35 |
| 32.09 | 2.79 | 14.79 |
| 32.55 | 2.75 | 12.5 |
| 33.66 | 2.66 | 22.14 |
| 35.76 | 2.51 | 12.99 |
| 37.86 | 2.38 | 9.93 |
| 38.67 | 2.33 | 6.92 |
| 39.11 | 2.30 | 6.28 |

Figure 16:
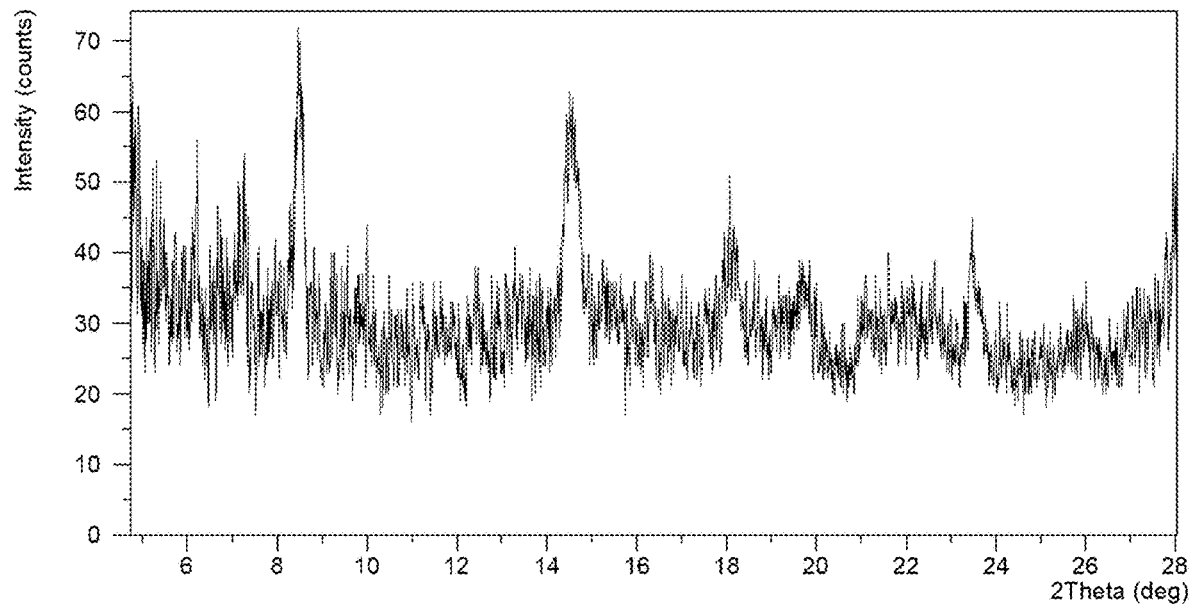
FIG. 16 is the XRPD pattern of the benzenesulfonate crystal form B of the quinazoline derivative of the present invention.

The XRPD (X-ray powder diffraction) pattern of the benzenesulfonate crystal form B of the quinazoline derivative (I) prepared according to the method described in the example is shown in FIG. 16, and the specific characteristics are shown in Table 17 below.

TABLE 17

| 2θ (°) | d interval (Å) | intensity % |
|---|---|---|
| 5.50 | 16.06 | 49.62 |
| 6.32 | 13.99 | 49.98 |
| 7.28 | 12.15 | 39.91 |
| 8.50 | 10.40 | 63.69 |
| 9.74 | 9.09 | 43.90 |
| 10.79 | 8.20 | 24.40 |
| 11.55 | 7.66 | 22.66 |
| 13.22 | 6.70 | 44.08 |
| 14.49 | 6.11 | 100.00 |
| 15.53 | 5.70 | 35.89 |
| 16.26 | 5.45 | 30.56 |
| 16.97 | 5.23 | 29.95 |
| 18.29 | 4.85 | 40.78 |
| 19.71 | 4.51 | 38.55 |
| 21.36 | 4.16 | 24.23 |
| 22.21 | 4.00 | 30.23 |
| 23.44 | 3.80 | 45.56 |
| 24.19 | 3.68 | 19.30 |
| 25.34 | 3.51 | 16.92 |
| 25.87 | 3.44 | 16.28 |
| 27.16 | 3.28 | 32.29 |

Figure 17:
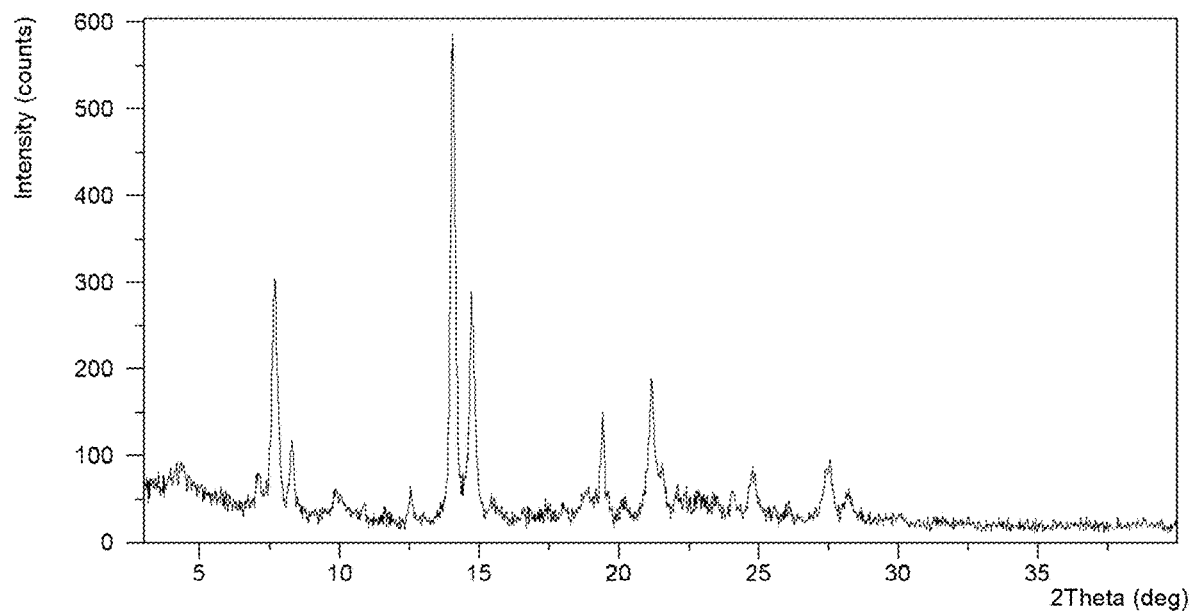
FIG. 17 is the XRPD pattern of the benzenesulfonate crystal form C of the quinazoline derivative of the present invention.

The XRPD (X-ray powder diffraction) pattern of the benzenesulfonate crystal form C of the quinazoline derivative (I) prepared according to the method described in the examples is shown in FIG. 17, and the specific characteristics are shown in Table 18:

TABLE 18

| 2θ (°) | d interval (Å) | intensity % |
|---|---|---|
| 4.24 | 20.84 | 10.69 |
| 7.07 | 12.50 | 8.87 |

TABLE 18-continued

| 2θ (°) | d interval (Å) | intensity % |
|---|---|---|
| 7.68 | 11.51 | 52.90 |
| 8.31 | 10.64 | 14.96 |
| 9.92 | 8.91 | 4.59 |
| 12.55 | 7.06 | 4.78 |
| 14.03 | 6.31 | 100.00 |
| 14.74 | 6.01 | 44.36 |
| 18.72 | 4.74 | 5.24 |
| 19.40 | 4.58 | 21.73 |
| 20.36 | 4.36 | 2.61 |
| 21.19 | 4.19 | 27.48 |
| 24.08 | 3.70 | 5.46 |
| 24.73 | 3.60 | 11.19 |
| 26.14 | 3.41 | 3.90 |
| 27.49 | 3.25 | 12.36 |
| 28.28 | 3.16 | 4.88 |
| 31.68 | 2.82 | 3.68 |
| 33.90 | 2.64 | 3.02 |
| 34.82 | 2.58 | 2.16 |
| 35.06 | 2.56 | 2.33 |
| 35.78 | 2.51 | 1.75 |
| 36.54 | 2.46 | 3.10 |
| 37.57 | 2.39 | 2.87 |
| 37.89 | 2.37 | 2.73 |
| 38.36 | 2.35 | 2.03 |
| 39.00 | 2.31 | 1.31 |

Figure 18:
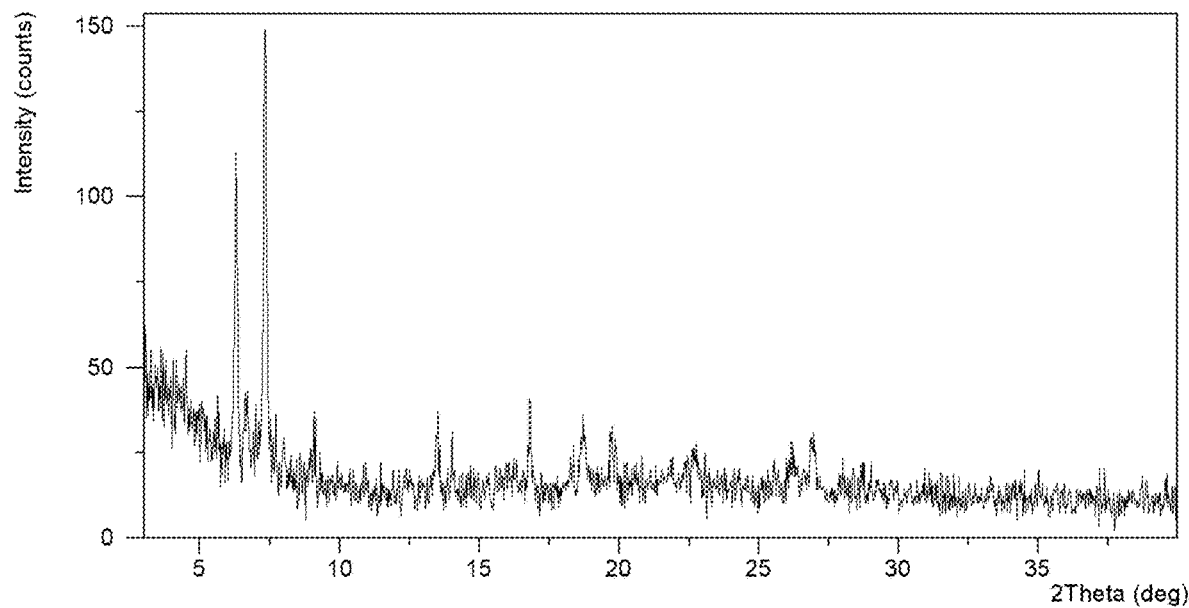
FIG. 18 is the XRPD pattern of the benzoate crystal form A of the quinazoline derivative of the present invention.

The XRPD (X-ray powder diffraction) pattern of the benzoate crystal form A of the quinazoline derivative (I) prepared according to the method described in the examples is shown in FIG. 18, and the specific characteristics are shown in Table 19 as follows:

TABLE 19

| 2θ (°) | d interval (Å) | intensity % |
|---|---|---|
| 4.45 | 19.85 | 15.08 |
| 6.31 | 14.01 | 67.89 |
| 6.65 | 13.29 | 23.85 |
| 7.33 | 12.07 | 100.00 |
| 7.69 | 11.50 | 5.08 |
| 8.01 | 11.04 | 12.47 |
| 11.85 | 7.47 | 13.66 |
| 13.53 | 6.55 | 26.15 |
| 16.02 | 5.53 | 6.27 |
| 16.77 | 5.29 | 17.92 |
| 18.75 | 4.73 | 18.13 |
| 19.95 | 4.45 | 17.28 |
| 21.06 | 4.22 | 12.38 |
| 21.76 | 4.08 | 13.46 |
| 22.56 | 3.94 | 10.02 |
| 23.41 | 3.80 | 32.14 |
| 26.94 | 3.31 | 11.08 |
| 27.44 | 3.25 | 9.45 |
| 27.61 | 3.23 | −4.66 |
| 27.98 | 3.19 | 17.13 |
| 28.55 | 3.12 | −2.78 |
| 29.05 | 3.07 | 14.42 |
| 31.92 | 2.80 | 15.05 |
| 32.29 | 2.77 | 6.49 |
| 32.93 | 2.72 | 13.92 |
| 33.72 | 2.66 | 8.69 |
| 34.61 | 2.59 | 11.39 |
| 35.35 | 2.54 | 13.57 |
| 35.95 | 2.50 | 15.56 |
| 37.08 | 2.42 | 9.03 |
| 38.13 | 2.36 | 8.06 |
| 39.62 | 2.27 | 14.14 |

Figure 19:
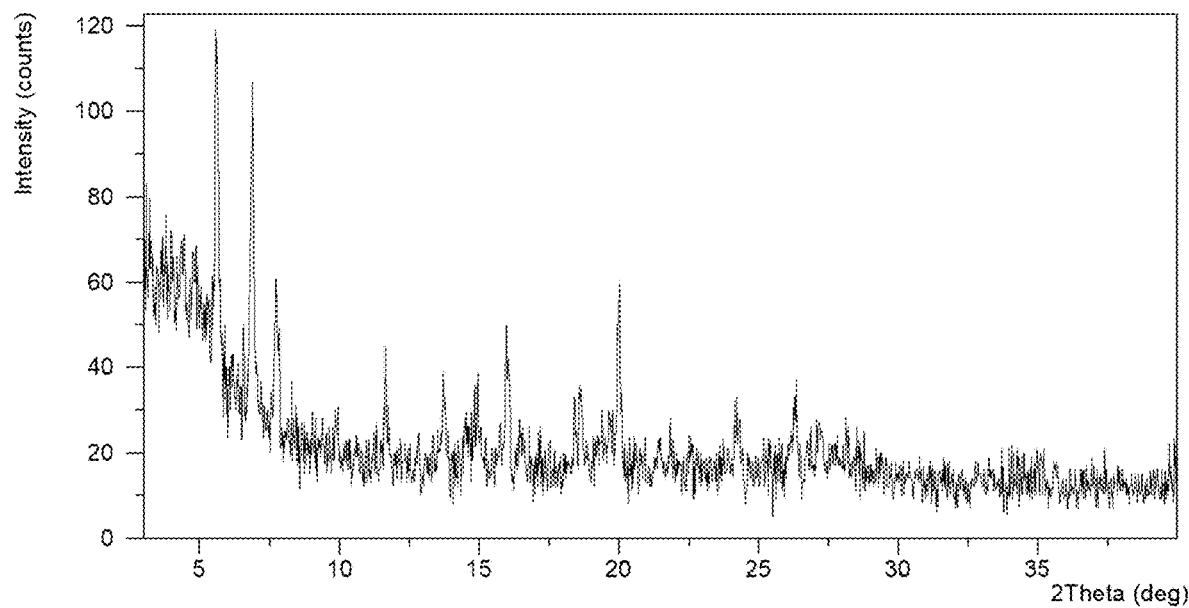
FIG. 19 is the XRPD pattern of hippurate crystal form A of the quinazoline derivative of the present invention.

The hippurate crystal form A of the quinazoline derivative (I) prepared according to the method described in the examples, its XRPD (X-ray powder diffraction) pattern is shown in FIG. 19, and the specific characteristics are shown in Table 20:

TABLE 20

| 2θ (°) | d interval (Å) | intensity % |
|---|---|---|
| 4.35 | 20.33 | 40.10 |
| 5.59 | 15.81 | 100.00 |
| 6.85 | 12.90 | 87.31 |
| 7.74 | 11.43 | 42.87 |
| 9.17 | 9.64 | 2.49 |
| 9.95 | 8.89 | 12.24 |
| 13.74 | 6.45 | 23.51 |
| 14.73 | 6.02 | 24.08 |
| 15.96 | 5.55 | 51.41 |
| 16.44 | 5.39 | 18.42 |
| 18.10 | 4.90 | 25.44 |
| 18.63 | 4.76 | 23.43 |
| 19.96 | 4.45 | 56.34 |
| 21.38 | 4.16 | 26.78 |
| 24.25 | 3.67 | 23.45 |
| 25.37 | 3.51 | 9.56 |
| 25.72 | 3.46 | 22.60 |
| 26.39 | 3.38 | 39.92 |
| 27.23 | 3.27 | 43.22 |
| 28.56 | 3.13 | 34.83 |
| 30.25 | 2.95 | 13.60 |
| 30.82 | 2.90 | 14.68 |
| 33.31 | 2.69 | 32.52 |
| 34.58 | 2.59 | 28.65 |
| 35.29 | 2.54 | 18.63 |
| 36.39 | 2.47 | 15.87 |
| 37.24 | 2.41 | 12.42 |
| 37.92 | 2.37 | 29.45 |

Figure 20:
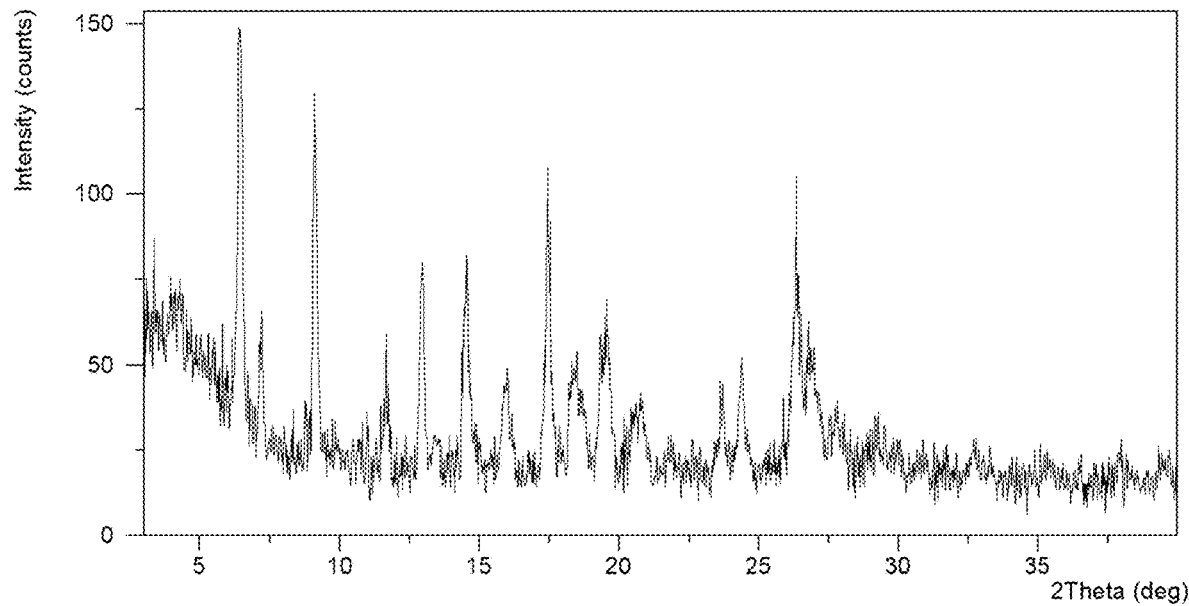
FIG. 20 is the XRPD pattern of the oxalate crystal form A of the quinazoline derivative of the present invention.

The XRPD (X-ray powder diffraction) pattern of the oxalate crystal form A of the quinazoline derivative (I) prepared according to the method described in the examples is shown in FIG. 20, and the specific characteristics are shown in Table 21 as follows:

TABLE 21

| 2θ (°) | d interval (Å) | intensity % |
|---|---|---|
| 4.11 | 21.50 | 42.22 |
| 6.44 | 13.72 | 100.00 |
| 7.15 | 12.36 | 28.22 |
| 8.75 | 10.11 | 14.31 |
| 9.06 | 9.76 | 78.08 |
| 9.88 | 8.95 | 14.16 |
| 11.26 | 7.86 | 9.82 |
| 11.58 | 7.64 | 16.84 |
| 12.92 | 6.85 | 49.20 |
| 14.52 | 6.10 | 45.34 |
| 15.87 | 5.58 | 20.53 |
| 17.47 | 5.08 | 55.56 |
| 18.29 | 4.85 | 21.96 |
| 19.43 | 4.57 | 22.90 |
| 20.14 | 4.41 | 10.67 |
| 20.49 | 4.33 | 9.30 |
| 23.70 | 3.75 | 18.85 |
| 24.34 | 3.66 | 18.44 |
| 26.36 | 3.38 | 48.67 |
| 26.92 | 3.31 | 28.22 |
| 29.75 | 3.00 | 10.41 |
| 31.72 | 2.82 | 7.18 |
| 32.67 | 2.74 | 12.99 |
| 32.99 | 2.72 | 13.80 |
| 34.21 | 2.62 | 9.18 |
| 34.52 | 2.60 | 7.03 |
| 34.86 | 2.57 | 11.22 |
| 36.36 | 2.47 | 12.64 |
| 36.91 | 2.44 | 8.86 |
| 37.91 | 2.37 | 13.59 |
| 39.03 | 2.31 | 8.52 | d is the distance between two adjacent crystal planes in the crystal lattice, in angstroms, and 16 is the intensity It can be seen from FIG. 1 that the XRPD pattern of the hydrochloride crystal form A of the quinazoline derivative (I) provided by the present invention is at 2θ=6.48, 7.31, 9.36, 10.26, 13.12, 14.37, 14.98, 16.06, 16.88, 17.48, 18.25, 20.01, 20.83, 21.55, 22.21, 23.35, 25.47, 26.60, 27.46, 28.29, 29.98, 34.07, 34.89, 36.25, 36.47, 36.87, 37.54, and the error range of the above 2θ value is ±0.2.

It can be seen from FIG. 2 that the XRPD pattern of the hydrochloride crystal form B of the quinazoline derivative (I) provided by the present invention is at 2θ=4.32, 5.98, 6.54, 7.28, 8.17, 10.52, 13.20, 15.99, 17.74, 18.48, 19.32, 19.84, 22.56, 23.88, 24.36, 24.87, 30.47, 32.92, 33.55, 34.60, 38.06, 38.34, and the error range of the above 2θ value is ±0.2.

It can be seen from FIG. 3 that the XRPD pattern of the hydrochloride crystal form H of the quinazoline derivative (I) provided by the present invention is at 2θ=5.83, 6.43, 7.26, 8.10, 10.24, 11.93, 13.22, 14.11, 14.45, 14.88, 15.78, 16.80, 17.95, 18.96, 20.25, 21.07, 21.65, 24.16, 24.53, 25.67, 26.37, 27.03, 27.61, and the error range of the above 2θ value is =0.2.

It can be seen from FIG. 4 that the XRPD pattern of the hydrochloride crystal form I of the quinazoline derivative (I) provided by the present invention is at 2θ=6.88, 7.42, 8.20, 12.31, 13.20, 13.88, 14.23, 14.66, 15.69, 17.48, 17.90, 18.64, 19.23, 20.24, 20.92, 21.94, 22.88, 23.42, 23.88, 25.12, 25.40, 25.85, 26.64, 28.07, 28.92, 31.19, 33.10, and the error range of the above 2θ value is =0.2.

It can be seen from FIG. 5 that the XRPD pattern of the fumarate crystal form A of the quinazoline derivative (I) provided by the present invention is at 2θ=6.51, 6.74, 7.47, 9.37, 10.82, 13.43, 13.97, 14.61, 17.78, 18.51, 18.80, 19.69, 20.90, 21.36, 21.68, 22.63, 23.76, 24.39, 27.09, 28.73, 29.69, 30.52, 31.07, 35.14, 36.12, 38.33 and the error range of the above 2θ value is ±0.2.

It can be seen from FIG. 6 that the XRPD pattern of the succinate crystal form A of the quinazoline derivative (I) provided by the present invention is at 2θ=3.92, 4.40, 6.56, 6.74, 7.50, 9.42, 11.92, 12.68, 13.53, 14.50, 14.84, 15.22, 15.68, 16.25, 17.82, 18.55, 19.48, 20.34, 20.99, 22.08, 22.59, 24.14, 24.52, 24.92, 28.07, 30.92, 36.11, and the error range of the above 2θ value is ±0.2.

It can be seen from FIG. 7 that the XRPD pattern of the maleate crystal form A of the quinazoline derivative provided by the present invention is at 2θ=6.25, 8.44, 8.68, 9.42, 10.41, 14.42, 14.88, 16.65, 17.93, 18.78, 20.58, 21.17, 22.63, 25.16, 31.15, 32.40, 33.66, 34.34, 34.52, 35.82, 36.06, 36.35, 36.91, and the error range of the above 2θ value is =0.2.

It can be seen from FIG. 8 that the XRPD pattern of the glycolate crystal form A of the quinazoline derivative provided by the present invention is at 2θ=4.53, 5.89, 6.59, 7.35, 10.02, 12.54, 13.26, 15.94, 17.93, 18.67, 19.36, 19.84, 21.06, 24.99, 31.13, 33.48, 34.79, 35.56, 36.17 and the error range of the above 2θ value is ±0.2.

It can be seen from FIG. 9 that the XRPD pattern of the hydrochloride crystal form F of the quinazoline derivative (I) provided by the present invention is at 2θ=4.91, 5.67, 6.51, 6.77, 7.44, 8.58, 9.20, 9.73, 10.40, 10.85, 11.86, 13.58, 14.30, 14.78, 15.57, 15.85, 16.15, 16.41, 16.97, 17.89, 18.96, 19.76, 20.45, 20.79, 21.57, 22.21, 24.17, and the error range of the above 2θ value is ±0.2.

It can be seen from FIG. 10 that the XRPD pattern of the hydrochloride crystal form C of the quinazoline derivative (I) provided by the present invention is at 2θ=5.66, 7.16, 8.32, 8.86, 9.52, 10.98, 11.63, 12.80, 13.57, 13.96, 14.81, 15.14, 15.49, 16.55, 16.86, 17.61, 22.04, 22.93, 24.55, 26.19, 27.30, 28.49, 34.12, 34.76, 35.65, 36.68, 37.31, 37.80, 38.20, 38.53, the error range of the above 2θ value It is +0.2.

It can be seen from FIG. 11 that the XRPD pattern of the hydrochloride crystal form D of the quinazoline derivative (I) provided by the present invention is at 2θ=3.43, 6.72, 7.12, 8.47, 9.32, 12.25, 13.44, 14.07, 15.69, 16.87, 17.22, 17.97, 19.77, 20.73, 22.25, 22.82, 23.64, 24.77, 25.40, 27.28, 28.13, 29.69, 31.01, 33.48, 34.87, 35.42, 38.08, and the error range of the above 28 value is ±0.2.

It can be seen from FIG. 12 that the XRPD pattern of the sulfuric acid crystal form A of the quinazoline derivative (I) provided by the present invention is at 2θ=7.27, 8.41, 11.88, 14.96, 18.23, 19.68, 20.64, 24.83, 25.82, 27.10, 28.16, 29.79, 30.71, 32.35, 34.12, 35.56, 37.56, and 38.37, and the error range of the above 2θ value is ±0.2.

It can be seen from FIG. 13 that the XRPD pattern of the oxalate crystal form A of the quinazoline derivative (I) provided by the present invention is at 2θ=5.43, 6.88, 7.38, 9.56, 13.68, 15.10, 15.43, 16.32, 16.88, 17.68, 18.60, 19.02, 20.58, 21.62, 22.33, 22.70, 23.35, 25.68, 27.29, 27.88, 28.53, 29.37, 31.35, 34.89, 37.11, 37.78, 38.17, 38.36, 39.65, the error range of the above 2θ value is ±0.2.

It can be seen from FIG. 14 that the XRPD pattern of the malate salt crystal form A of the quinazoline derivative (I) provided by the present invention is at 2θ=5.43, 6.53, 7.49, 8.35, 9.17, 12.10, 13.16, 16.17, 18.77, 19.85, 20.79, 23.14, 23.94, 26.66, 28.25, 29.32, 30.38, 33.24, 33.69, 34.80, 35.97, 36.87, 37.88, and the error range of the above 2θ value is ±0.2.

It can be seen from FIG. 15 that the XRPD pattern of the benzenesulfonate crystal form A of the quinazoline derivative provided by the present invention is at 2θ=5.48, 6.56, 7.08, 7.65, 8.14, 8.48, 9.71, 10.55, 11.14, 11.77, 13.32, 13.95, 15.32, 16.46, 16.89, 17.82, 19.15, 19.70, 20.43, 21.02, 21.98, 22.68, 23.23, 25.26, 26.07, 26.59, 28.63, 29.09, 30.45, 31.12, 32.09, 32.55, 33.66, 35.76, 37.86, 38.67, 39.11, and the error range of the above 2θ value is ±0.2.

It can be seen from FIG. 16 that the XRPD pattern of the benzenesulfonate crystal form B of the quinazoline derivative provided by the present invention is at 2θ=5.50, 6.32, 7.28, 8.50, 9.74, 10.79, 11.55, 13.22, 14.49, 15.53, 16.26, 16.97, 18.29, 19.71, 21.36, 22.21, 23.44, 24.19, 25.34, 25.87, 27.16, and the error range of the above 2θ value is ±0.2.

It can be seen from FIG. 17 that the XRPD pattern of the benzenesulfonate crystal form C of the quinazoline derivative (I) provided by the present invention is at 2θ=4.24, 7.07, 7.68, 8.31, 9.92, 12.55, 14.03, 14.74, 18.72, 19.40, 20.36, 21.19, 24.08, 24.73, 26.14, 27.49, 28.28, 31.68, 33.90, 34.82, 35.06, 35.78, 36.54, 37.57, 37.89, 38.36, 39.0, and the error range of the above 2θ value is ±0.2.

It can be seen from FIG. 18 that the XRPD pattern of the benzoate crystal form A of the quinazoline derivative (I) provided by the present invention is at 29-4.45, 6.31, 6.65, 7.33, 7.69, 8.01, 11.85, 13.53, 16.02, 16.77, 18.75, 19.95, 21.06, 21.76, 22.56, 23.41, 26.94, 27.44, 27.61, 27.98, 28.55, 29.05, 31.92, 32.29, 32.93, 33.72, 34.61, 35.35, 35.95, 37.08, 38.13, 39.62, and the error range of the 2θ value is ±0.2.

It can be seen from FIG. 19 that the XRPD pattern of hippurate crystal form A of the quinazoline derivative (I) provided by the present invention is at 2θ=4.35, 5.59, 6.85, 7.74, 9.17, 9.95, 13.74, 14.73, 15.96, 16.44, 18.10, 18.63, 19.96, 21.38, 24.25, 25.37, 25.72, 26.39, 27.23, 28.56, 30.25, 30.82, 33.31, 34.58, 35.29, 36.39, 37.24, 37.9, and the error range of the above 2θ value is ±0.2.

It can be seen from FIG. 20 that the XRPD pattern of the oxalate crystal form A of the quinazoline derivative (I) provided by the present invention is at 2θ=4.11, 6.44, 7.15, 8.75, 9.06, 9.88, 11.26, 11.58, 12.92, 14.52, 15.87, 17.47, 18.29, 19.43, 20.14, 20.49, 23.70, 24.34, 26.36, 26.92, 29.75, 31.72, 32.67, 32.99, 34.21, 34.52, 34.86, 36.36, 36.91, 37.91, 39.03. The error range is +0.2.

After testing, the error range of the 2θ value can also be ±0.2. Those skilled in the art should understand that these diffraction peaks do not represent the details of the diffraction peaks for the hydrochloride crystal forms A, B, C, D, F of the quinazoline derivative (I), H. I, Sulfate Form A. Maleate Form A, Succinate Form A, Adipate Form A, Glycolate Form A, Malate Form A, Fumarate salt crystal form A, besylate crystal form A, B. C, benzoate crystal form A, hippurate crystal form A and oxalate crystal form A. The 2θ value of the X-ray powder diffraction pattern can be slightly changed with changes in the machine, sample preparation and batch-to-batch changes, and the quoted value is not regarded as an absolute value. It should also be understood that the absolute intensity of the peak may also vary with the orientation effect. Therefore, the intensity shown in the present invention is exemplary and not used for absolute comparison.

Example 23. Biological Activity of the Quinazoline Derivative (I)

The cell viability test of tumor cells with EGFR activating mutation (exon 19 deletion Exon 19 Del) protein and glioma uses CellTiter-Glo (CTG) assay: about 5000 cells are grown in each blank 96-well plate After 16 hours, add the proportionally diluted compound. After 72 hours of drug addition, equilibrate at room temperature for 30 minutes. Add 100 microliters of CellTiter-Glo reagent to each well and mix on an orbital shaker for 2 minutes to induce cell lysis. The plate was incubated at room temperature for 10 minutes to stabilize the luminescence signal. The luminescence signal was recorded on the TECAN Infinite M1000 Pro instrument.

TABLE 22

Inhibition of growth of non-small cell lung cancer PC-9 tumor cells and glioma tumor cells (The unit of IC50 is nM))

|  | PC-9 tumor cell (EGFR Del 19 mutation) | Glioma PDX with EGFRVIII mutation |
|---|---|---|
| The quinazoline derivative (I) with R configuration | 8 nM | 10 nM |
| the S enantiomer of the quinazoline derivative (I) with R configuration | 4 nM | >1000 nM |
| EGFRinhibitors such as erlotinib, gefitinib for NSCLC | <20 nM | >200 nM |

Figure 21:
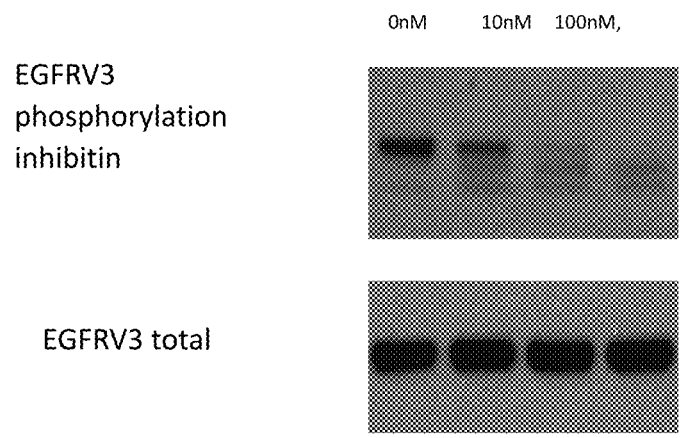
FIG. 21 is a schematic diagram of the inhibition of EGFRVIII phosphorylation by quinazoline derivatives of the present invention.

It can be seen from Table 22 that the quinazoline derivative (I) with the configuration of R according to the present invention has unexpected EGFRVIII mutation activity, which is >100 times higher activity than the enantiomer activity while has similar biological activity for EGFR Del 19 activating mutation. As shown in FIG. 21, in the western blot experiment, the phosphorylation of EGFRV3 was inhibited by the quinazoline derivative (I), which shows that the quinazoline derivative (I) has good biological activity and specifically targets cancer mediated by EGFRV3 phosphorylation.

Example 24. Blood-Brain Barrier Penetration Rate of the Quinazoline Derivative (I)

To determine whether the quinazoline derivative (I) can cross the blood-brain barrier (BBB), the test compound was administered to rats orally. Four hours after the administration, the rats were killed, blood and brain tissue were collected, and the concentration of the test compound was analyzed. Brain penetration is defined as the ratio of the concentration of the compound in brain tissue to the concentration in plasma. Crossing the blood-brain barrier is the ratio of the free concentration of the drug in the brain tissue to the free concentration of the drug in the plasma. P-glycoprotein is an efflux protein of the blood-brain barrier, which discharges the P-glycoprotein substrate into the skull. Breast cancer resistance protein is an efflux protein from the blood-brain barrier, which excretes breast cancer resistance protein into the brain.

TABLE 23

The ability of quinazoline derivatives (I) to cross the blood-brain barrier

| | quinazoline derivatives (I) |
|---|---|
| Blood brain barrier penetration rate | >50% |
| P-gp efflux substrate | no |
| BCRP efflux substrate | no |

In the detection of the rate of crossing the blood-brain barrier, the ratio of the free concentration of the compound (I) in the brain tissue to the free concentration in the plasma is higher than 50%, and it is not a P-glycoprotein or BCRP substrate. It can cross the blood-brain barrier, so it has the potential to achieve effective blood drug concentration in the brain, be used for the treatment of glioma or the treatment and prevention of cancer brain metastases, meningeal metastases, brain cancer and others Central nervous system disease, and reduce the risk of dose-limiting toxicity outside the skull.

Figure 22:
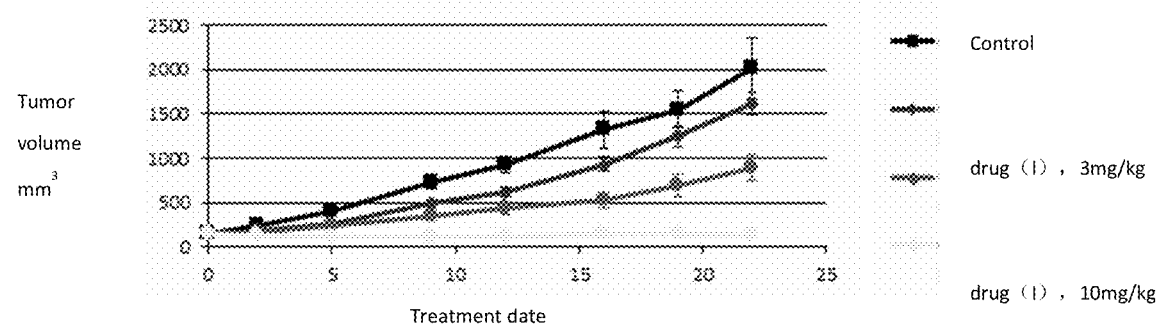
FIG. 22 is a schematic diagram of the pharmacodynamic study of the quinazoline derivative of the present invention in a humanized glioma mouse subcutaneous model.

Example 25. Pharmalogical Efficacy of Quinazoline Derivative (I) for Glioma with EGFRVIII Mutation on Subcue Pdx Mouse Model The patient's primary tumor tissue (brain tumor) was implanted under the skin of the mouse, and the tumor grew to about 150 cubic millimeters, and the medication was started for three weeks. In the pharmacodynamic experiment of a tumor subcutaneous transplantation animal mouse model of a patient primary brain tumor tissue with EGFRVIII mutation, the first group was the control group and did not contain any drugs. The second group of quinazoline derivatives (I) single agent, 3 mg/kg, orally, twice a day, the third group of quinazoline derivatives (I) single agent, 10 mg/kg, orally, two times a day, the fourth group of quinazoline derivatives (I) is a single agent, 20 mg/kg, orally, twice a day. As shown in FIG. 22, the medication group (the second, third, and fourth group) compared with the first group (control group) all showed good inhibition of tumor growth, with statistically significant efficacy, and showed a dose-dependent manner in the animal model. The fourth group caused tumor reduction, showing good pharmacological effects with a statistically significant difference in efficacy. RNA sequencing of tumors showed mutations of EGFRV3, showing that quinazoline derivatives (I) have good biological activity and efficacy against EGFRV3 mutations.

Example 26. Equilibrium Solubility of Quinazoline Derivative (I) and its Salt Crystal Forms Experimental method: Weigh about 10 mg of solid sample (free base and various salt forms and crystal forms), add 1.5 mL of water, and after equilibrate at room temperature for 24 hours, take out 0.3 mL of turbid solution, and centrifuge to separate the lower solid and supernatant. After the supernatant was filtered through a 0.45 μm (PTFE) filter, the concentration of free alkali was tested.

TABLE 23

| | |
|---|---|
| quinazoline derivative (I) free base solubility (ug/mL) | <5 ug/mL |
| Hydrochloride crystal form A, B, C, D, F, H, I, sulfate crystal form A, maleate crystal form A, succinate crystal form A, adipate crystal form A, glycolate crystal form A, malate crystal form A, fumarate crystal form A, besylate crystal form A, B, C, benzoate crystal form A, hippurate crystal form A and oxalate crystal form A of quinazoline derivative (I) | >50 ug/mL |

It can be seen from Table 23 that each salt crystal form of the quinazoline derivative (I) of the present invention has a good equilibrium solubility in water. Preferably, the hydrochloride crystal forms A, B, H, I and fumarate crystal form A of the quinazoline derivative (I) of the present invention has equilibrium solubility in water>500 ug/mL. This is very beneficial to the absorption of drugs.

Example 27. Stability Studies

Figure 23A:
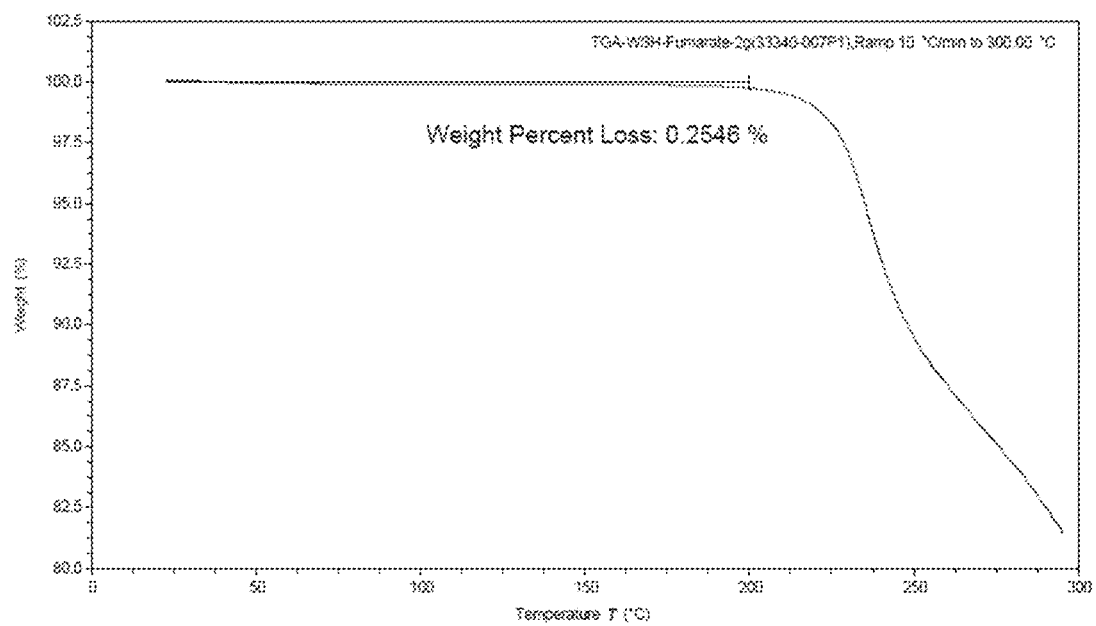
Figure 23B:
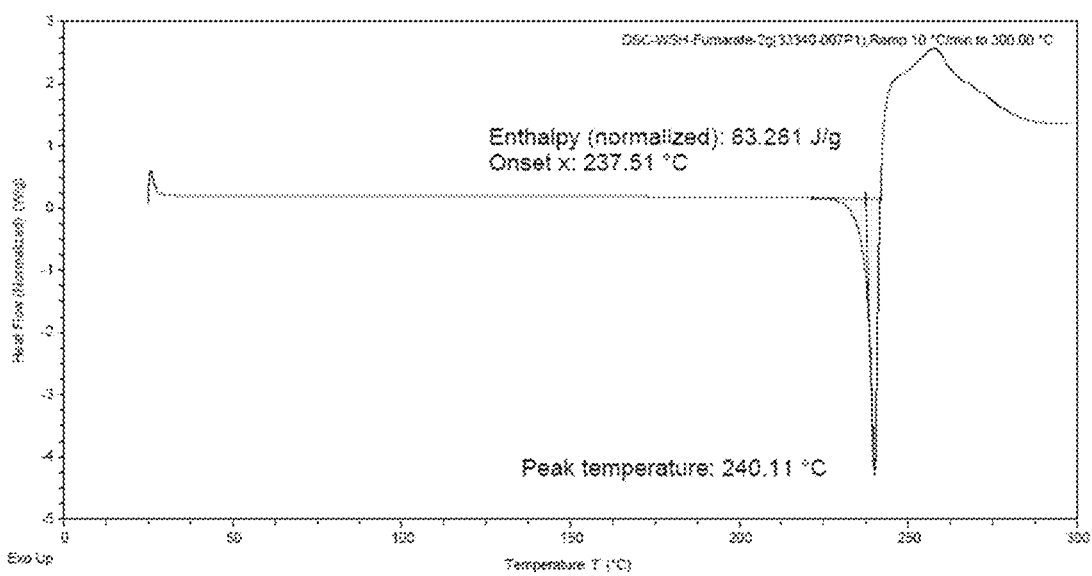

The one-week physical and chemical stability of the salt form and crystal form of the quinazoline derivative (I) of the present invention is stable in physical and chemical properties when stored at 25° C./60% RH and 40° C./75% RH for one week. During the heating process, the TGA chart showed that there was no significant change in the crystal forms in Examples 2-21. In particular, the DSC chart showed that the fumarate crystal form A showed good stability. As shown in FIG. 23A and FIG. 23B, the fumarate crystal form A has no significant weight loss during the heating process, and the melting point is about 240 degrees Celsius. Such properties are conducive to the preparation and processing of tablets.

Example 28. Good Bioavailability of the Quinazoline Derivative (I) of the Present Invention In the rat pharmacokinetic study, a group of rats (three rats) were injected intravenously with 1-2 mg/kg, and the second group of rats (three rats) were orally administered 2-40 mg/kg at 7 time points (0.25, 0.5, 1, 2, 4, 8, 16 hours) of the quinazoline derivative (I) of the present invention. Take blood to measure the concentration of the quinazoline derivative (I) of the present invention in the blood, and calculate the peak area and half-life. The calculation method of bioavailability is: (peak area of drug oral/oral dose)/(peak area of drug intravenous injection/intravenous dose)×100%. The salt forms and crystal forms of the quinazoline derivative (I) of the present invention have good bioavailability, all of which are greater than >35%.

Preferably: hydrochloride crystal form B, H, I (bioavailability>60%) and fumarate crystal form A (bioavailability 80%);

More preferably: Fumarate crystal form A (bioavailability 80%, half-life 7.4 hours).

Figure 24:
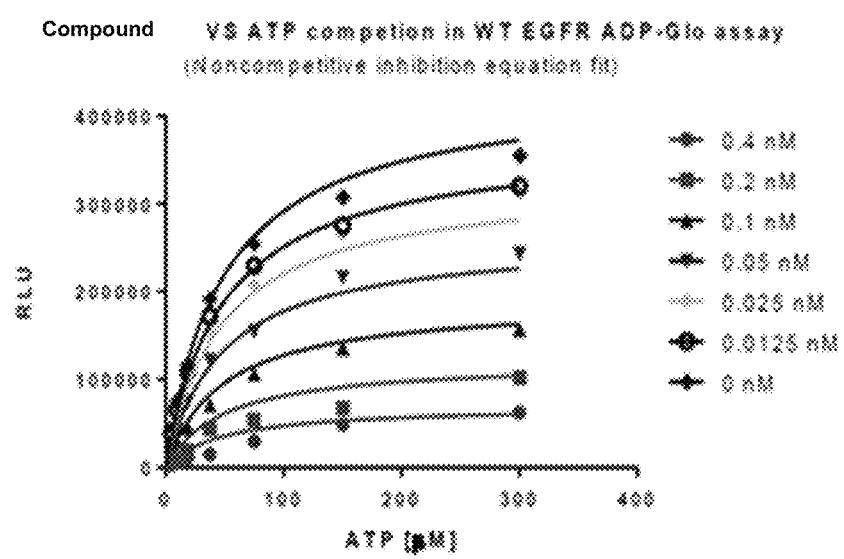
FIG. 24 is a schematic diagram of the inhibitory mechanism of quinazoline derivatives of the present invention and EGFR.

Example 29. Mechanism Action of the Quinazoline Derivative (I) of the Present Invention In the experiment of the quinazoline derivative (I) of the present invention on the mechanism of inhibiting EGFR, the EGFR enzyme was added to the 384-well plate from 6 concentrations diluted in equal proportions (2 times) of 0.4 nM to 0.0125 nM and 0 concentration in polyE4Y1 solution, incubate for 15 minutes, add 7 concentrations of ATP diluted from 600 uM in equal proportions (2 times) to react for 60 minutes, add ADP-Glo reagent and detection reagent for 40 minutes to measure RLU signal. As shown in FIG. 24, the quinazoline derivative (I) of the present invention shows an unexpected non-ATP competition mechanism. The benefits of this mechanism of action are obvious. The quinazoline derivative (I) of the present invention has this mechanism of action, showing high activity and high selectivity, and has the characteristics of small side effects and resistance to drug resistance.

In summary, the quinazoline derivative (I) of the present invention that has a 6-substituted (3,3-difluoro-1-methylpiperidin-4-yl) oxy group with a chirality of R, has high biological activity, high selectivity, high blood-brain barrier penetration rate, non-efflux substrate, and has the inhibitory properties of non-ATP competition mechanism. At the same time, it has significant pharmacological effects on non-small cell lung cancer and glioma with high bioavailability. It should be emphasized that the quinazoline derivative (I) of the present invention has unexpected effects on non-small cell lung cancer (mediated by a certain form of EGFR activation, particularly EGFR Del19 and/or EGFR L858R) caused activating mutations) and glioma (mediated by a certain form of EGFR activation, especially those caused by EGFRVIII activating mutations), high biological activity, high selectivity, and high blood-brain barrier crossing rate of non-ATP competitive inhibitors. In particular, the non-competitive inhibitory properties of the quinazoline derivative (I) with the chirality of R in the present invention bring high activity and high selectivity, and especially have high activity against glioma.

The hydrochloride crystal form A, B, C, D, F, H, I, sulfate crystal form A, maleate crystal form A, succinate crystal form A, adipate crystal form A, glycolate crystal form A, malate crystal form A, fumarate crystal form A, besylate crystal form A, B, C, benzoate crystal form A, hippurate crystal form A and oxalate crystal form A of the quinazoline derivative of the present invention in water has better solubility than that of the quinazoline derivative represented by formula (I), no crystal form conversion occurs during heating, and has good stability.

The hydrochloride crystal form A, B, C, D, F, H, I, sulfate crystal form A, maleate crystal form A, succinate crystal form A, adipate crystal form A, glycolate crystal form A, malate crystal form A, fumarate crystal form A, besylate crystal form A, B, C, benzoate crystal form A, hippurate crystal form A and oxalate crystal form A of the quinazoline derivative of the present invention have unexpectedly superior physicochemical properties, which are beneficial for use in pharmaceutical processing and pharmaceutical compositions. It can be applied to the treatment of non-small cell lung cancer brain metastasis, meningeal metastasis, head and neck squamous cell carcinoma, squamous cell carcinoma, brain stem tumor, primary brain cancer or glioma, etc., while providing qualitative and quantitative information for efficacy and safety is of great significance for further research on the efficacy and safety of such solid drugs.

The specific embodiments of the present invention have been described above. It should be understood that the present invention is not limited to the above specific embodiments, and those skilled in the art can make various deformations or modifications within the scope of the claims, which does not affect the essence of the present invention

What is claimed is:

1. A crystal form of a hydrochloride salt of a quinazoline derivative represented by formula (I), wherein the crystal form is a first crystal form, a second crystal form, a third crystal form, a fourth crystal form, a fifth crystal form, a sixth crystal form or a seventh crystal form;

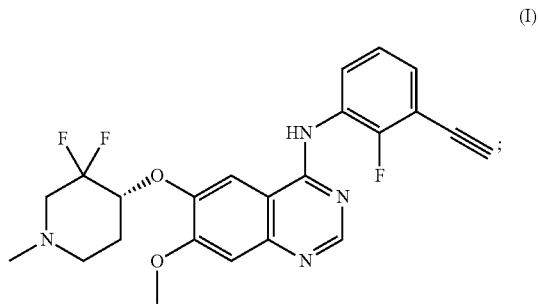

(I)

wherein, an XRPD pattern of the first crystal form has main characteristic peaks at the following 2θ: 6.5, 13.1, 9.4; has secondary characteristic peaks at the following 2θ: 7.3, 18.2, 20.0; and has characteristic peaks again at the following 2θ: 27.5, 26.6, 21.6;

an XRPD pattern of the second crystal form has main characteristic peaks at the following 2θ: 6.5, 17.7, 19.8; and has secondary characteristic peaks at the following 2θ: 7.3, 8.2, 10.5, 13.2;

an XRPD pattern of the third crystal form has main characteristic peaks at the following 2θ: 7.2, 17.6, 22.0; has secondary characteristic peaks at the following 2θ: 14.0, 13.6, 12.8; and has characteristic peaks again at the following 2θ: 24.6, 26.2, 27.3;

an XRPD pattern of the fourth crystal form has main characteristic peaks at the following 2θ: 13.4, 7.1, 25.4; has secondary characteristic peaks at the following 2θ: 6.7, 18.0, 19.8; and has characteristic peaks again at the following 2θ: 17.2, 27.3, 24.7;

an XRPD pattern of the fifth crystal form has main characteristic peaks at the following 2θ: 6.8, 20.5, 13.6; and has secondary characteristic peaks at the following 2θ: 14.8, 14.3, 17.9, 11.9;

an XRPD pattern of the sixth crystal form has main characteristic peaks at the following 2θ: 7.3, 18.0, 14.1; has secondary characteristic peaks at the following 2θ: 6.4, 13.2, 15.8; and has characteristic peaks again at the following 2θ: 16.8, 14.5, 20.3;

an XRPD pattern of the seventh crystal form has main characteristic peaks at the following 2θ: 18.6, 7.4, 6.9; has secondary characteristic peaks at the following 2θ:

13.2, 25.1, 12.3; and has characteristic peaks again at the following 2θ: 14.7, 28.1, 14.2;
an error range of a 2θ value is ±0.2.

2. A method for preparing the crystal form according to claim 1, wherein:
a preparation method of the first crystal form comprises the following steps: adding 0.8 to 1.2 equivalents of a first organic solvent and hydrochloric acid to the quinazoline derivative represented by the formula (I), stirring at 22-28 degrees Celsius, and centrifugating to separate a lower solid to obtain the first crystal form; wherein 10 to 200 mg of the quinazoline derivative represented by the formula (I) is added to each milliliter of the first organic solvent; the first organic solvent is methanol;
a preparation method of the second crystal form comprises the following steps: adding the quinazoline derivative represented by the formula (I) to a second organic solvent to obtain a suspension, and adding 0.8 to 1.2 equivalents of hydrochloric acid to the suspension, stirring at 22-28 degrees Celsius, and centrifugating to separate a lower layer of wet solid to obtain the second crystal form;
wherein 10 to 200 mg of the quinazoline derivative represented by the formula (I) is added to each milliliter of the second organic solvent; the second organic solvent is acetonitrile, ethyl acetate, or a tetrahydrofuran/water solution having a volume ratio of (15-20): 1,
a preparation method of the third crystal form comprises the following steps: adding the quinazoline derivative represented by the formula (I) to a third organic solvent and adding 2 to 2.5 equivalents of hydrochloric acid, stirring at 22-28 degrees Celsius, centrifugating to separate a lower layer of wet solid to obtain the third crystal form of dihydrochloride; wherein 10 to 200 mg of the quinazoline derivative represented by the formula (I) is added to each milliliter of the third organic solvent; the third organic solvent is acetone;
a preparation method of the fourth crystal form comprises the following steps: heating a sample of the quinazoline derivative represented by the formula (I) in the third crystal form of hydrochloride to 120-160 degrees Celsius and then cooling to 22-28 degrees Celsius to obtain the fourth crystal form of dihydrochloride salt;
a preparation method of the fifth crystal form comprises the following steps: adding the quinazoline derivative represented by the formula (I) in the second crystal form of hydrochloride to an alcoholic organic solvent and an ester organic solvent, and conducting a gas-liquid diffusion at 22-28 degrees Celsius until a solid precipitates to obtain the fifth crystal form; wherein 10 to 200 mg of the quinazoline derivative represented by the formula (I) in the second crystal form of hydrochloride is added to each milliliter of the alcoholic organic solvent and the ester organic solvent; the alcoholic organic solvent is methanol, and the ester organic solvent is isopropyl acetate;
a preparation method of the sixth crystal form comprises the following steps: adding a fourth organic solvent to the quinazoline derivative represented by the formula (I) in the second crystal form of hydrochloride, filtering and volatilizing at 22-28 degrees Celsius to obtain the sixth crystal form; wherein 10 to 200 mg of the quinazoline derivative represented by the formula (I) in the second crystal form of hydrochloride is added to each milliliter of the fourth organic solvent; the fourth organic solvent is ethanol;
a preparation method of the seventh crystal form comprises the following steps: heating a sample of the quinazoline derivative represented by the formula (I) in the sixth crystal form of hydrochloride to 120-130 degrees Celsius and then cooling to 22-28 degrees Celsius.

3. A crystal form of a fumarate of a quinazoline derivative represented by formula (I),

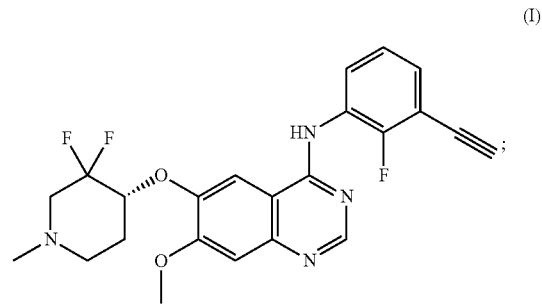 [SMILES: C#Cc1cccc(Nc2ncnc3cc(OC)c(O[C@@H]4CCN(C)CC4(F)F)cc23)c1F]

an XRPD pattern of the crystal form has main characteristic peaks at the following 2θ: 6.5, 17.8, 9.4; has secondary characteristic peaks at the following 2θ: 13.4, 7.5, 19.7; and has characteristic peaks again at the following 2θ: 14.6, 18.5; an error range of a 2θ value is ±0.2.

4. A method for preparing the crystal form according to claim 3, wherein the method comprises: adding the quinazoline derivative of the formula (I) and 0.4-0.6 equivalent of fumaric acid to an organic solvent, stirring at 22-28 degrees Celsius, centrifugating to collect a solid to obtain the crystal form; wherein 10 to 200 mg of the quinazoline derivative represented by the formula (I) is added to each milliliter of the organic solvent.

5. A crystal form of a succinate of an quinazoline derivative represented by formula (I),

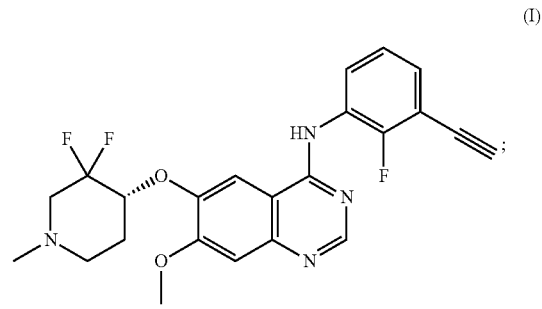 [SMILES: C#Cc1cccc(Nc2ncnc3cc(OC)c(O[C@@H]4CCN(C)CC4(F)F)cc23)c1F]

an XRPD pattern of the crystal form has main characteristic peaks at the following 2θ: 6.6, 17.8, 7.5; has secondary characteristic peaks at the following 2θ: 9.4, 20.3, 18.5; and has characteristic peaks again at the following 2θ: 21.0, 14.5, 19.5; an error range of a 2θ value is ±0.2.

6. A method for preparing the crystal form according to claim 5, wherein the method comprises: adding an organic solvent to the quinazoline derivative of the formula (I) and 0.8-1.2 equivalents of succinic acid, then stirring at 22-28 degrees Celsius, and centrifugating to collect a solid to obtain the crystal form; wherein 10 to 200 mg of the quinazoline derivative represented by the formula (I) is added to each milliliter of the organic solvent.

7. A crystal form of a maleate salt of a quinazoline derivative represented by formula (I),

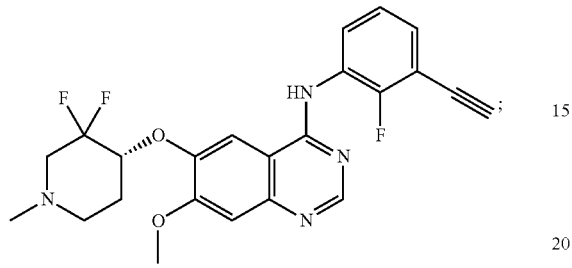
(I)

an XRPD pattern of the crystal form has main characteristic peaks at the following 2θ: 6.3, 18.8, 16.7; and has secondary characteristic peaks at the following 2θ: 25.2, 21.2; wherein an error range of a 2θ value is ±0.2.

8. A method for preparing the crystal form according to claim 7, wherein the method comprises: adding the quinazoline derivative of the formula (I) and 0.8-1.2 equivalents of maleic acid to an organic solvent, stirring at 22-28 degrees Celsius, and centrifugating to collect a solid to obtain the crystal form; wherein 10 to 200 mg of the quinazoline derivative represented by the formula (I) is added to each milliliter of the organic solvent.

9. A crystal form of a glycolate of a quinazoline derivative represented by formula (I),

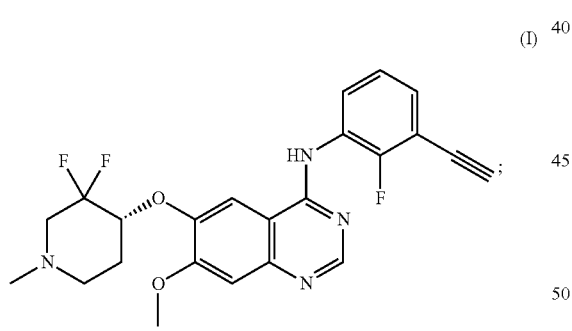
(I)

an XRPD pattern of the crystal form has main characteristic peaks at the following 2θ: 6.6, 7.4, 17.9; and has secondary characteristic peaks at the following 2θ: 13.3; wherein an error range of a 2θ value is ±0.2.

10. A method for preparing the crystal form according to claim 9, wherein the method comprises: after adding the quinazoline derivative represented by the formula (I) and 0.8-1.2 equivalents of glycolic acid to an organic solvent, stirring at 22-28 degrees Celsius, and centrifugating to collect a solid to obtain the crystal form; wherein 10 to 200 mg of the quinazoline derivative represented by the formula (I) is added to each milliliter of the organic solvent.

11. A crystal form of a sulfate salt of the quinazoline derivative represented by formula (I),

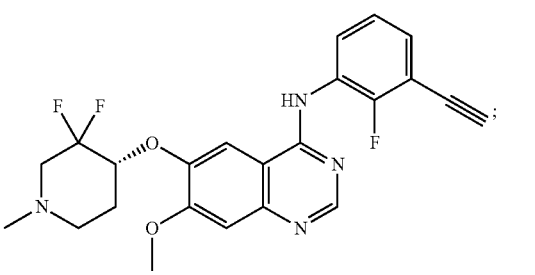
(I)

an XRPD pattern of the crystal form has main characteristic peaks at the following 2θ: 7.3, 18.2, 15.0; wherein an error range of a 2θ value is ±0.2.

12. A method for preparing the crystal form according to claim 11, wherein the method comprises: adding a sample of the quinazoline derivative represented by the formula (I) to an organic solvent and 0.8-1.2 equivalents of sulfuric acid aqueous solution, stirring at 22-28 degrees Celsius, and centrifugating to collect a solid to obtain the crystal form; wherein 10 to 200 mg of the quinazoline derivative represented by the formula (I) is added to each milliliter of the organic solvent.

13. A crystal form of a malate salt of a quinazoline derivative represented by formula (I),

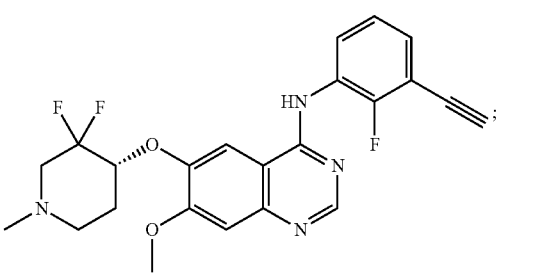
(I)

an XRPD pattern of the crystal form has main characteristic peaks at the following 2θ: 6.5, 18.8, 19.9; and has secondary characteristic peaks at the following 2θ: 7.5, 8.4, 9.2; wherein an error range of a 2θ value is ±0.2.

14. A method for preparing the crystal form according to claim 13, wherein the method comprises: adding a sample of the quinazoline derivative represented by the formula (I) to an organic solvent and 0.8-1.2 equivalents of malic acid, stirring at 22-28 degrees Celsius, and centrifugating to collect a solid to obtain the crystal form; wherein 10 to 200 mg of the quinazoline derivative represented by the formula (I) is added to each milliliter of the organic solvent.

15. A crystal form of a benzenesulfonate of a quinazoline derivative represented by formula (I), wherein the crystal form is a first crystal form, a second crystal form or a third crystal form;

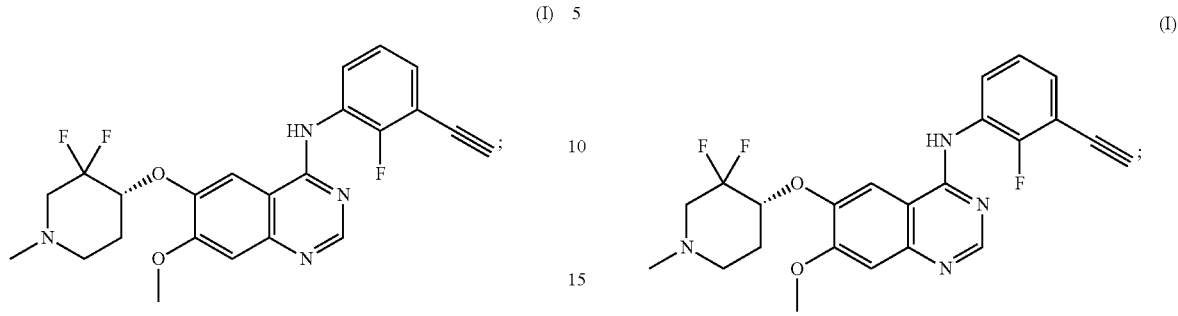

(I)

wherein, an XRPD pattern of the first crystal form has main characteristic peaks at the following 2θ: 6.6, 14.0, 15.3; has secondary characteristic peaks at the following 2θ: 7.1, 5.5, 19.7; and has characteristic peaks again at the following 2θ: 17.8, 16.9, 21.0;
an XRPD pattern of the second crystal form has main characteristic peaks at the following 2θ: 8.5, 14.5, 23.4; and has secondary characteristic peaks at the following 2θ: 18.3, 19.7;
an XRPD pattern of the third crystal form has main characteristic peaks at the following 2θ: 14.0, 14.7, 7.7; has secondary characteristic peaks at the following 2θ: 8.3, 21.2, 19.4; and has characteristic peaks again at the following 2θ: 27.5, 24.7;
an error range of a 2θ value is ±0.2.

16. A method for preparing the crystal form according to claim 15, wherein a preparation method of the first crystal form comprises: adding a sample of the quinazoline derivative represented by the formula (I) to a first organic solvent and 0.8-1.2 equivalents of benzenesulfonic acid, stirring at 22-28 degrees Celsius, and centrifugating to collect a solid to obtain the first crystal form; wherein 10 to 200 mg of the quinazoline derivative represented by the formula (I) is added to each milliliter of the first organic solvent; the first organic solvent is methanol;
a preparation method of the second crystal form comprises: adding a sample of the quinazoline derivative represented by the formula (I) to a second organic solvent and 0.8-1.2 equivalents of benzenesulfonic acid, stirring at 22-28 degrees Celsius, and centrifugating to collect a solid to obtain the second crystal form; wherein 10 to 200 mg of the quinazoline derivative represented by the formula (I) is added to each milliliter of the second organic solvent; the second organic solvent is acetonitrile;
a preparation method of the third crystal form comprises: adding a sample of the quinazoline derivative represented by the formula (I) to a third organic solvent and 0.8-1.2 equivalents of benzenesulfonic acid, stirring at 22-28 degrees Celsius, and centrifugating to collect a solid to obtain the third crystal form; wherein 10 to 200 mg of the quinazoline derivative of the formula (I) is added to each milliliter of the third organic solvent; the third organic solvent is a mixed solvent of tetrahydrofuran and water at a volume ratio of (15-20):1.

17. A crystal form of a benzoate of a quinazoline derivative represented by formula (I),

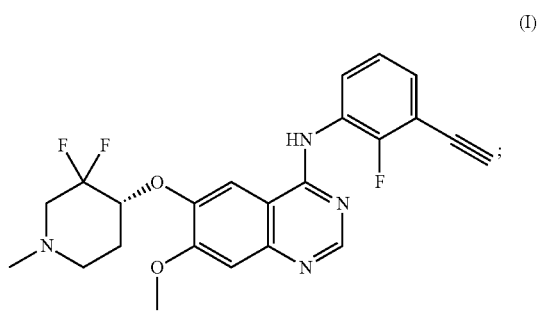 [SMILES: C#Cc1cccc(Nc2ncnc3cc(OC)c(O[C@@H]4CCN(C)CC4(F)F)cc23)c1F]

(I)

an XRPD pattern of the crystal form has main characteristic peaks at the following 2θ: 7.3, 6.3, 16.8; and has secondary characteristic peaks at the following 2θ: 13.5, 18.7, 27.0; wherein an error range of a 2θ value is ±0.2.

18. A method for preparing the crystal form according to claim 17, wherein the method comprises: adding a sample of the quinazoline derivative represented by the formula (I) to an organic solvent and 0.8-1.2 equivalents of benzoic acid, stirring at 22-28 degrees Celsius, and centrifugating to collect a solid to obtain the crystal form; wherein 10 to 200 mg of the quinazoline derivative represented by the formula (I) is added to each milliliter of the organic solvent.

19. A crystal form of a hippurate of a quinazoline derivative represented by formula (I), (I)

an XRPD pattern of the crystal form has main characteristic peaks at the following 2θ: 5.6, 6.9, 20.0; has secondary characteristic peaks at the following 2θ: 16.0, 7.7, 13.7; and has characteristic peaks again at the following 2θ: 24.3, 26.4; an error range of a 2θ value is ±0.2.

20. A method for preparing the crystal form according to claim 19, wherein the method comprises: adding a sample of the quinazoline derivative represented by the formula (I) to an organic solvent and 0.8-1.2 equivalents of hippuric acid, stirring at 22-28 degrees Celsius, and centrifugating to collect a solid to obtain the crystal form; wherein 10 to 200 mg of the quinazoline derivative represented by the formula (I) is added to each milliliter of the organic solvent.

21. A crystal form of an oxalate of a quinazoline derivative represented by formula (I),

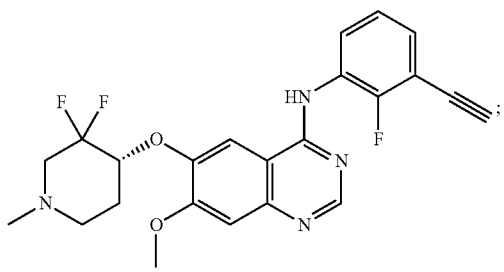

an XRPD pattern of the crystal form has main characteristic peaks at the following 2θ: 6.4, 9.1, 17.5; has secondary characteristic peaks at the following 2θ: 12.9, 14.5, 26.4; and has characteristic peaks again at the following 2θ: 19.4, 18.3, 15.9; an error range of a 2θ value is ±0.2.

22. A method for preparing the crystal form according to claim 21, wherein the method comprises: adding a sample of the quinazoline derivative represented by the formula (I) to an organic solvent and 0.8-1.2 equivalents of oxalic acid, stirring at 22-28 degrees Celsius, and centrifugating to collect a solid to obtain the crystal form; wherein 10 to 200 mg of the quinazoline derivative represented by the formula (I) is added to each milliliter of the organic solvent.

23. A pharmaceutical composition, wherein the pharmaceutical composition comprises the crystal form according to claim 1, and pharmaceutically acceptable excipients or auxiliary components.

24. A method for treating or preventing diseases mediated by an epidermal growth factor receptor (EGFR) protein, comprising the step of administering to a subject the crystal form according to claim 1 or a pharmaceutical composition, wherein the pharmaceutical composition comprises the crystal form according to claim 1 and pharmaceutically acceptable excipients or auxiliary components.

25. The method according to claim 24, wherein the diseases mediated by the epidermal growth factor receptor (EGFR) protein are caused by EGFRVIII activation mutations.

26. The method according to claim 24, wherein the diseases mediated by the epidermal growth factor receptor (EGFR) protein are caused by EGFR Del19 and/or EGFR L858R activating mutations.

27. The method according to claim 24, wherein the diseases mediated by an epidermal growth factor receptor (EGFR) protein are non-small cell lung cancer brain metastasis, meningeal metastasis, head and neck squamous cell carcinoma, squamous cell carcinoma, brain stem tumor, primary brain cancer or glioma.

* * * * *